(12) United States Patent
Benning et al.

(10) Patent No.: US 9,315,838 B2
(45) Date of Patent: Apr. 19, 2016

(54) METHOD TO INCREASE ALGAL BIOMASS AND ENHANCE ITS QUALITY FOR THE PRODUCTION OF FUEL

(71) Applicant: Board of Trustees of Michigan State University, East Lansing, MI (US)

(72) Inventors: Christoph Benning, East Lansing, MI (US); Xiaobo Li, East Lansing, MI (US); Bensheng Liu, Lansing, MI (US); Min-Hao Kuo, East Lansing, MI (US); Barbara Sears, Haslett, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 51 days.

(21) Appl. No.: 14/073,959

(22) Filed: Nov. 7, 2013

(65) Prior Publication Data

US 2014/0134685 A1    May 15, 2014

Related U.S. Application Data

(60) Provisional application No. 61/723,662, filed on Nov. 7, 2012.

(51) Int. Cl.
  *C12P 7/64* (2006.01)
  *C12N 15/82* (2006.01)

(52) U.S. Cl.
  CPC ............ *C12P 7/6463* (2013.01); *C12N 15/8247* (2013.01); *Y02E 50/13* (2013.01)

(58) Field of Classification Search
  None
  See application file for complete search history.

(56) References Cited

U.S. PATENT DOCUMENTS

2010/0154077 A1* 6/2010 Emmanuel et al. ........... 800/281
2012/0288930 A1  11/2012 Trimbur

FOREIGN PATENT DOCUMENTS

| CN | 101892159 A | 11/2010 |
|---|---|---|
| KR | 20090033691 A | 4/2009 |
| WO | WO-00/61740 A1 | 10/2000 |
| WO | WO-2008/150463 A2 | 12/2008 |

OTHER PUBLICATIONS

Hill et al (Functional analysis of conserved histidines in ADP-glucose pyrophosphorylase from *Escherichia coli*. Biochem. Biophys. Res. Comm. 244:573-577, 1998).*
Guo et al (Protein tolerance to random amino acid change, Proc. Natl. Acad. Sci. USA 101:9205-9210, 2004).*
Song et al (Construction of DNA-Shuffled and Incrementally Truncated Libraries by a Mutagenic and Unidirectional Reassembly Method: Changing from a Substrate Specificity of Phospholipase to That of Lipase. Applied and Environmental Microbiology, p. 6146-6151, Dec. 2002).*
Merchant et al (Database ID A8IWH9_CHLRE. The Chlamydomonas Genome. Reveals the Evolution of Key Animal and Plant Functions. Science 318:245-251, Dec. 2007).*
Radakovits et al (Genetic Engineering of Algae for Enhanced Biofuel Production. Eukaryotic Cell. p. 486-501, Apr. 2010), in view of Merchant et al (2007).*
Siaut et al (Oil accumulation in the model green alga Chlamydomonas reinhardtii: characterization, variability between common laboratory strains and relationship with starch reserves. BMC Biotechnology 2011, 11:7. p. 1-15. Published on Jan. 2011).*
Li et al (A Galactoglycerolipid Lipase is Required for Triacylglycerol Accumulation and Survival Following Nitrogen Deprivation in Chlamydomonas reinhardtii. The Plant Cell, vol. 24: 4670-4686, Nov. 2012).*
Beer, L. L., et al., "Engineering algae for biohydrogen and biofuel production", *Current Opinion in Biotechnology*, 20(3), (Jun. 2009), 264-271.
Li, X., et al., "A Galactoglycerolipid Lipase is Required for Triacylglycerol Accumulation and Survival Following Nitrogen Deprivation in Chlamydomonas reinhardtii", *The Plant Cell*, 24(11), (Nov. 2012), 4670-4686.

* cited by examiner

*Primary Examiner* — Medina A Ibrahim
*Assistant Examiner* — Wayne Zhong
(74) *Attorney, Agent, or Firm* — Schwegman Lundberg & Woessner, P.A.

(57) ABSTRACT

The invention provides a recombinant cell having a nucleotide sequence encoding a polypeptide which is a lipase having at least 40% amino acid sequence identity to a polypeptide having SEQ ID NO:1, and methods of using the recombinant cell to produce triacylglycerols or to increase oil production by the cell.

21 Claims, 20 Drawing Sheets

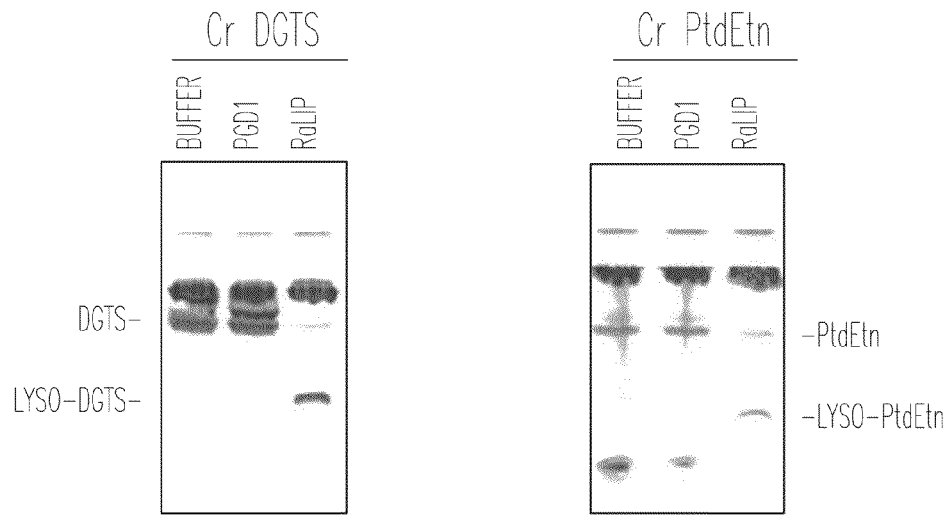
*Fig. 16A*  *Fig. 16B*
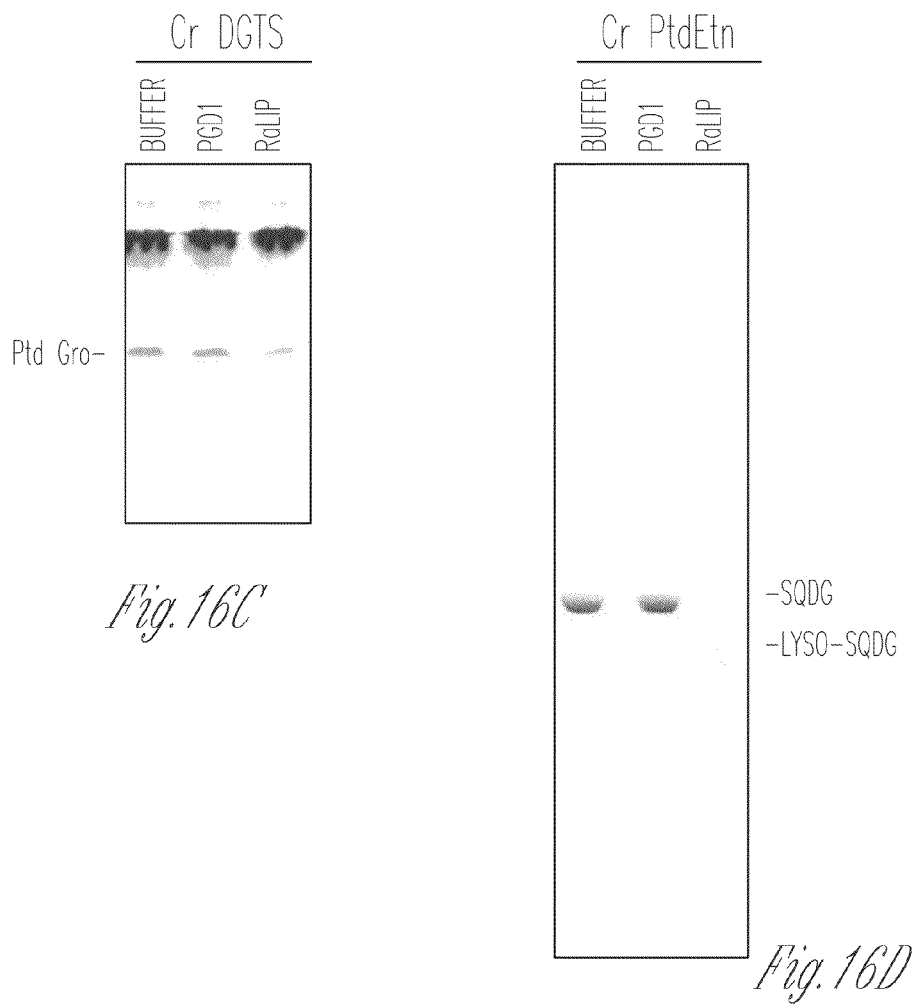
*Fig. 16C*  *Fig. 16D*

METHOD TO INCREASE ALGAL BIOMASS AND ENHANCE ITS QUALITY FOR THE PRODUCTION OF FUEL

CROSS-REFERENCE TO RELATED APPLICATIONS

The application claims the benefit of the filing date of application Ser. No. 61/723,662, filed on Nov. 7, 2012, the disclosure of which is incorporated by reference herein.

STATEMENT OF GOVERNMENT RIGHTS

This invention was made with government support under FA9550-11-1-0264 awarded by the U.S. Air Force Office of Scientific Research. The government has certain rights in the invention.

BACKGROUND

Triacylglycerol (TAG) is a universal storage lipid in plants, algae, fungi, and animals. TAG is composed of a glycerol backbone to which three fatty acyl chains are esterified. By transesterification with methanol, TAG can be converted into fatty acid methylesters (FAMEs) commonly referred to as biodiesel (Durrett et al. 2008). Microalgae have been considered as sustainable feedstock for the production of biofuels because they accumulate substantial amounts of TAG following nutrient deprivation. Theoretical calculations suggest that microalgae can surpass crop plants in their TAG yield per land area used (Weyer et al. 2010). Despite the recent interest in microalgae, this phylogenetically diverse group of photosynthetic organisms is not well understood at the molecular and biochemical levels, and the mechanistic basis of algal lipid metabolism and of TAG accumulation still needs to be explored in detail. Much of the current molecular understanding of photosynthetic lipid biosynthesis is based on work with *Arabidopsis thaliana* and other land plant models, providing paradigms that may not be directly transferable given their evolutionary divergence from microalgae. Indeed, current information on lipid metabolism in the green algal model *Chlamydomonas reinhardtii*, which is mostly based on genome annotation (Riekhof et al. 2005) or early labeling and lipid profiling experiments (Giroud et al. 1988, Giroud and Eichenberger 1989), suggests that lipid metabolism in this organism is distinct in crucial aspects from that of land plants. Most strikingly, *Chlamydomonas* lacks phosphatidylcholine (PtdCho), but instead contains the betaine lipid diacylglycerol-N,N,N,-trimethylhomoserine (DGTS).

Seed plants typically have two assembly pathways for glycerolipids (Roughan and Slack 1982). Fatty acids are synthesized de novo in the plastid while attached to acyl carrier proteins (ACPs) (Ohlrogge et al. 1979). Acyltransferases at the inner chloroplast envelope membrane transfer acyl groups from acyl-ACPs to glycerol 3-phosphate leading to the formation of phosphatidic acid (PtdOH), the precursor of glycerolipids of the thylakoid membrane. Alternatively, fatty acids are exported from the plastid for assembly of extraplastidic glycerolipids including TAGs at the endoplasmic reticulum (ER). Because the acyltransferases associated with the inner plastid envelope membrane and the ER have different acyl group preferences, glycerolipids assembled by the two pathways can be distinguished based on their acyl group composition (Heinz and Roughan 1983). In *Chlamydomonas*, the analysis of the acyl groups in the glyceryl backbone of the galactoglycerolipids, which are the predominant lipids in the thylakoid membranes, suggests that their assembly is completely dependent on the plastid pathway (Giroud et al. 1988). In contrast, in seed plants such as *Arabidopsis* the galactoglycerolipid molecular species are nearly equally derived from the ER and the plastid assembly pathway (Browse et al. 1986), thus requiring an elaborate system of lipid transfer between the ER and the plastid envelopes (Benning 2009).

In particular, the lack of phosphatidylcholine (PtdCho) in *Chlamydomonas* is expected to affect other aspects of glycerolipid metabolism. For example, isotope labeling of cytosolic lipids in pea leaves indicated that most of the acyl groups synthesized de novo in the plastid are first incorporated into PtdCho instead of PtdOH (Bates et al. 2007). Thus, it was proposed that acyl editing of PtdCho is an important aspect of fatty acid export from the plastid, cycling acyl groups through PtdCho before they enter the cytosolic acyl-CoA pool, which ultimately provides acyl groups for glycerolipid assembly at the ER. The lack of PtdCho in *Chlamydomonas* raises several questions, particularly whether an alternative mechanism of acyl editing, possibly involving DGTS or another lipid, or a mechanism completely independent of acyl editing exists, which is involved in the export of fatty acids from the plastid. Typically, lipid droplets are formed at the ER in all eukaryotic cells. However, recent reports on TAG accumulation in *Chlamydomonas* suggest that TAG-containing lipid droplets are present in plastids (Fan et al. 2011, Goodson et al. 2011), raising the possibility that TAG is either directly assembled in plastids, or imported into them.

Aside from the basic mechanisms of glycerolipid assembly in *Chlamydomonas*, the details of the regulation of TAG synthesis are unclear as well. Like other microalgae, *Chlamydomonas* produces lipid droplets filled with TAGs following nutrient deprivation (Moellering and Benning 2010, Wang et al. 2009), conditions that involve genome-wide transcriptional changes (Castruita et al. 2011, Miller et al. 2010). Intriguingly, among the genes up-regulated or down-regulated by N deprivation were a large number of genes annotated to encode lipases (Miller et al. 2010).

SUMMARY OF THE INVENTION

Following nitrogen (N) deprivation microalgae accumulate triacylglycerols. To gain mechanistic insights into this phenomenon, mutants were identified with reduced TAG content following N deprivation in the model alga *Chlamydomonas reinhardtii*. In one of the mutants, the disruption of a galactoglycerolipid lipase-encoding gene, tentatively designated Plastid Galactoglycerolipid Degradation 1 (PGD1), was responsible for the primary phenotype: reduced TAG content, altered TAG composition, and reduced galactoglycerolipid turnover. The recombinant PGD1 protein, which was purified from *E. coli* extracts, hydrolyzed monogalactosyldiacylglycerol into its lyso-lipid derivative. In vivo pulse-chase labeling identified galactoglycerolipid pools as a major source of fatty acids esterified in triacylglycerols following N deprivation. Moreover, the fatty acid flux from plastid lipids to triacylglycerol was decreased in the pgd1 mutant. Apparently, de novo synthesized fatty acids in *Chlamydomonas* are, at least partially, first incorporated into plastid lipids before they enter triacylglycerol synthesis. As a secondary effect, the pgd1 mutant exhibited a loss of viability following N deprivation, which could be avoided by blocking photosynthetic electron transport. Thus, the pgd1 mutant provides evidence for an important biological function of triacylglycerol synthesis following N deprivation, namely relieving a detrimental overreduction of the photosynthetic electron transport chain.

Expression of PGD1 gene in the mutant increased the production of oil and so over-expression of galactolipase PGD1, which catalyzes an acyl-editing cycle, in wild-type algae and heterologous expression in other algal species or plants will likely increase oil production, as the tested galactolipase PGD1 contributed to 50% of total oil made by *Chlamydomonas*. The presence of PGD1 also increased the percentage of 18:1 fatty acid or mono-unsaturated fatty acids in the oil, which is desired for high-quality biodiesel. Since the PDG1 gene is conserved in green algae and land plants, a wide range of genes encoding proteins that are structurally and functionally related to *Chlamydomonas* PGD 1 may be employed as isolated protein or provided in recombinant cells.

The invention provides an isolated algal cell having a mutation in a gene encoding a polypeptide which is a lipase such as a galactoglycerolipid lipase, e.g., one where the polypeptide has at least 40%, 50%, 60%, 65%, 70%, 80%, 85%, 90%, 95%, 97%, 99% or 100% amino acid sequence identity to a polypeptide having SEQ ID NO:1, 2 or 3. In one embodiment, the isolated algal cell is a recombinant algal cell, e.g., a recombinant red, green or brown alga such as one having a genome that is augmented with an expression cassette encoding a lipase.

Further provided is a recombinant alga or plant cell having a nucleotide sequence encoding a polypeptide which is a lipase galactoglycerolipid lipase, e.g., one where the polypeptide has at least 40%, 50%, 60%, 65%, 70%, 80%, 85%, 90%, 95%, 97%, 99% or 100% amino acid sequence identity to a polypeptide having SEQ ID NO:1, 2 or 3, or a fragment thereof, so that the cell has increased TAG production or oil production relative to a corresponding non-recombinant cell. In one embodiment, the recombinant cell is an algal cell, e.g., *Archaeplastida, Rhizaria, Excavata* or, *Chromista, Alveolata* or *Chlamydomonas*, or *Nannochloropsis*, Phaeophyceae or *Phytophthora infestans*. In one embodiment, the algal cell is a Chlorophyta (green algae), Rhodophyta (red algae), or Phaeophyceae (brown algae) cell. In one embodiment, the recombinant cell is a bacterial cell, e.g., a *Streptococcus, Pseudomonas, Staphylococcus* or *E. coli*. In one embodiment, the recombinant cell is a plant cell, e.g., a plant cell from a plant that produces oil such as a corn, cannola, palm, soybean, peanut, or walnut plant.

The invention thus provides for production of oil from algae with high energy density, or plants, or other cells, which in turn provides for feedstock for biodiesel production. Moreover, algae can be grown on marginal lands and so do not compete for space with food producing organisms that reside in or on land.

BRIEF DESCRIPTION OF THE FIGURES

FIG. 16. Activity of the recombinant PGD1 protein on DGTS, PtdEtn, PtdGro and SQDG. Thin-layer chromatograms of polar lipids from the PGD1 assay mixtures to which *Chlamydomonas*-derived membrane lipids were added as substrates. Lipid abbreviations are as described in FIG. 4. Exposure to iodine vapor was used to visualize lipids for reactions on DGTS, PtdEtn and PtdGro. SQDG and lyso- SQDG were stained by α-naphtol reagent. Substrates treated with *Rhizopus* lipase was used to generate the lyso-lipid standards. A representative result is shown for each panel.

DETAILED DESCRIPTION

Definitions

Figure 1:
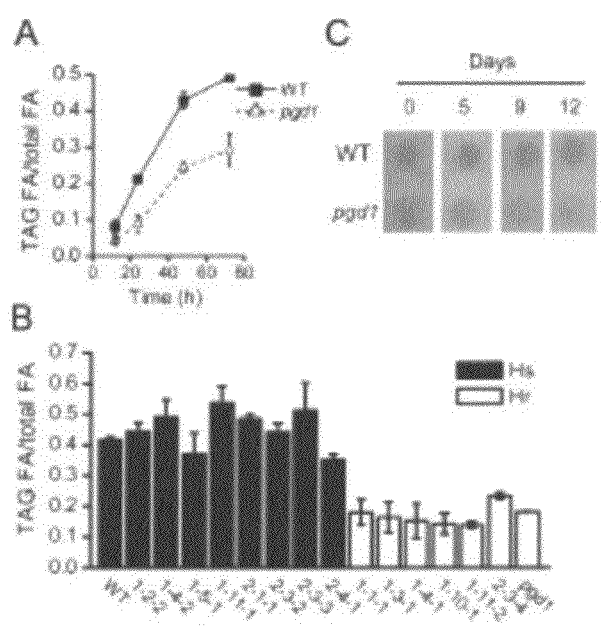
FIG. 1. Phenotypes of the pgd1 mutant compared to the wild-type parental strain (WT). (A) Time course of triacylglycerol (TAG) accumulation following N deprivation and (B) phenotypic analysis of progenies from a cross between pgd1 and CC-198. Hs and Hr indicate Hygromycin B sensitive and resistant lines respectively. (A, B) The ratio of fatty acids (FA) in TAGs over total fatty acids in the lipid extracts is shown. Averages of three independent measurements are provided. Error bars indicate standard deviation. (C) Appearance of the same patches of N-deprived cells placed on agar-solidified TAP-N medium, 0-12 days after plating.

As used herein, the term "isolated" refers to in vitro preparation and/or isolation of a nucleic acid molecule, e.g., vector or plasmid, or peptide or polypeptide (protein), or cell, so that it is not associated with in vivo substances, or is substantially purified from in vitro substances. Thus, for example, an "isolated oligonucleotide", "isolated polynucleotide", "isolated protein", or "isolated polypeptide" refers to a nucleic acid or amino acid sequence that is identified and separated from at least one contaminant with which it is ordinarily associated in its source. For example, an isolated nucleic acid or isolated polypeptide may be present in a form or setting that is different from that in which it is found in nature. In contrast, non-isolated nucleic acids (e.g., DNA and RNA) or non-isolated polypeptides (e.g., proteins and enzymes) are found in the state they exist in nature. For example, a given DNA sequence (e.g., a gene) is found on the host cell chromosome in proximity to neighboring genes; RNA sequences (e.g., a specific mRNA sequence encoding a specific protein), are found in the cell as a mixture with numerous other mRNAs that encode a multitude of proteins. However, isolated nucleic acid includes, by way of example, such nucleic acid in cells ordinarily expressing that nucleic acid where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide contains at a minimum, the sense or coding strand (i.e., a single-stranded nucleic acid), but may contain both the sense and anti-sense strands (i.e., a double-stranded nucleic acid).

The term "nucleic acid molecule," "polynucleotide" or "nucleic acid sequence" as used herein, refers to nucleic acid, DNA or RNA that comprises coding sequences necessary for the production of a polypeptide or protein precursor. The encoded polypeptide may be a full-length polypeptide, a fragment thereof (less than full-length), or a fusion of either the full-length polypeptide or fragment thereof with another polypeptide, yielding a fusion polypeptide.

By "peptide," "protein" and "polypeptide" is meant any chain of amino acids, regardless of length or post-translational modification (e.g., glycosylation or phosphorylation). The nucleic acid molecules of the invention encode a variant of a naturally-occurring protein or polypeptide fragment thereof, which has an amino acid sequence that is at least 60%, e.g., at least 65%, 70%, 75%, 80%, 85%, 90%, 95%, 96%, 97%, 98%, or 99%, but less than 100%, amino acid sequence identity to the amino acid sequence of the naturally-occurring (native or wild-type) protein from which it is derived. The polypeptides of the invention thus include those with conservation substitutions, e.g., relative to the polypeptide having SEQ ID NO:1 and/or a polypeptide with at least 60%, e.g., at least 65%, 70%, 75%, 80%, 85%, 90%, 95%, 96%, 97%, 98%, or 99%, but less than 100%, amino acid sequence identity to a polypeptide having SEQ ID NO:1. Amino acid residues may be those in the L-configuration, the D-configuration or nonnaturally occurring amino acids such as norleucine, L-ethionine, β-2-thienylalanine, 5-methyltryptophan, norvaline, L-canavanine, p-fluorophenylalanine, p-(4-hydroxybenzoyl)phenylalanine, 2-keto-4-(methylthio) butyric acid, beta-hydroxy leucine, gamma-chloronorvaline, gamma-methyl D-leucine, beta-D-L hydroxyleucine, 2-amino-3-chlorobutyric acid, N-methyl-D-valine, 3,4-difluoro-L-phenylalanine, 5,5,5-trifluoroleucine, 4,4,4,-trifluoro-L-valine, 5-fluoro-L-tryptophan, 4-azido-L-phenylalanine, 4-benzyl-L-phenylalanine, thiaproline, 5,5,5-trifluoroleucine, 5,5,5,5',5',5'-hexafluoroleucine, 2-amino-4-methyl-4-pentenoic acid, 2-amino-3,3,3-trifluoromethylpentanoic acid, 2-amino-3-methyl-5,5,5-trifluoropentanoic acid, 2-amino-3-methyl-4-pentenoic acid, trifluorovaline, hexafluorovaline, homocysteine, hydroxylysine, ornithine, and those with peptide linkages optionally replaced by a linkage such as, —CH$_2$NH—, —CH$_2$S—, —CH$_2$—CH$_2$—, —CH=CH— (cis and trans), —COCH$_2$—, —CH(OH)CH$_2$—, and —CH$_2$SO—, by methods known in the art. In keeping with standard polypeptide nomenclature, abbreviations for naturally occurring amino acid residues are as shown in the following Table of Correspondence.

TABLE OF CORRESPONDENCE

| 1-Letter | 3-Letter | AMINO ACID |
| --- | --- | --- |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

The term "fusion polypeptide" or "fusion protein" refers to a chimeric protein containing a reference protein (e.g., luciferase) joined at the N- and/or C-terminus to one or more heterologous sequences (e.g., a non-luciferase polypeptide).

Protein primary structure (primary sequence, peptide sequence, protein sequence) is the sequence of amino acids. It is generally reported starting from the amino-terminal (N) end to the carboxyl-terminal (C) end. Protein secondary structure can be described as the local conformation of the peptide chain, independent of the rest of the protein. There are 'regular' secondary structure elements (e.g., helices, sheets or strands) that are generally stabilized by hydrogen bond interactions between the backbone atoms of the participating residues, and 'irregular' secondary structure elements (e.g., turns, bends, loops, coils, disordered or unstructured segments). Protein secondary structure can be predicted with different methods/programs, e.g., PSIPRED, PORTER, or DSC, see http://www.expasy.org/tools/#secondary for a list. Protein tertiary structure is the global three-dimensional (3D) structure of the peptide chain. It is described by atomic positions in three-dimensional space, and it may involve interactions between groups that are distant in primary structure. Protein tertiary structures are classified into folds, which are specific three-dimensional arrangements of secondary structure elements. Sometimes there is no discernable sequence similarity between proteins that have the same fold.

As used herein, "substantially purified" means the object species is the predominant species, e.g., on a molar basis it is more abundant than any other individual species in a composition, and preferably is at least about 80% of the species present, and optionally 90% or greater, e.g., 95%, 98%, 99% or more, of the species present in the composition.

The term "homology" refers to a degree of complementarity between two or more sequences. There may be partial homology or complete homology (i.e., identity). Homology is often measured using sequence analysis software (e.g., "GCG" and "Seqweb" Sequence Analysis Software Package formerly sold by the Genetics Computer Group, University of Wisconsin Biotechnology Center. 1710 University Avenue, Madison, Wis. 53705). Such software matches similar sequences by assigning degrees of homology to various substitutions, deletions, insertions, and other modifications.

Sources of Cells for Recombinant Expression and Methods of Preparation and Use

One of a set of down-regulated genes in response to N deprivation in *Chlamydomonas* was shown to encode a lipase involved in TAG turnover in *Chlamydomonas* (Li et al. 2012). As a complement to transcript profiling in revealing genes involved in TAG metabolism or its regulation, a genetic screen was developed for mutants with abnormal TAG levels following N deprivation. A low-TAG mutant was identified with a lesion in a galactoglycerolipid lipase-encoding gene. This gene was among the up-regulated lipase-encoding genes following N deprivation (Miller et al. 2010), consistent with a role for acyl editing or turnover of galactoglycerolipids during TAG formation in *Chlamydomonas*. The availability of a low TAG mutant of *Chlamydomonas* also allowed the examination of the physiological role of TAG accumulation following nutrient stress.

Triacylglycerol (TAG) is composed of a glycerol backbone to which three fatty acyl chains are esterified. By transesterification with methanol, TAG can be converted into fatty acid methyl esters (FAMEs) commonly referred to as biodiesel. Microalgae have been considered as sustainable feedstock for the production of biofuels because they accumulate substantial amounts of TAG following nutrient deprivation. A genetic screen was developed for mutants with abnormal TAG levels following N deprivation. In one of the mutants, the disruption of a galactoglycerolipid lipase-encoding gene, tentatively designated PGDI, was responsible for the primary phenotype: reduced TAG content, altered TAG composition. Mechanistic studies show that PGD1 protein catalyzes an acylediting cycle to export fatty acids (mainly monounsaturated fatty acids) from the plastid for TAG biosynthesis. The mutant of *Chlamydomonas reinhardtii* with impaired oil accumulation was shown to be deficient in a lipase with specificity for newly assembled monogalactolipids, and the data indicated that passage of fatty acids synthesized in the chloroplast is through a transient chloroplast membrane lipid pool into triacylglycerols. The results also indicate a role of oil biosynthesis for survival following nutrient deprivation.

The invention provides preparations of microbial cells, such as bacteria, yeast, alga and fungi, as well as plant cells and plants and other eukaryotes. Algal cells useful in the invention include but are not limited to Chlorophyta (green algae), Rhodophyta (red algae), Glaucophyta, Chlorarachniophytes, Euglenids, Bacillariophyceae (Diatoms), Axodine, Bolidomonas, Eustigmatophyceae, Phaeophyceae (brown algae), Chrysophyceae (golden algae), Raphidophyceae, Synurophyceae, Xanthophyceae (yellow-green algae), Cryptophyta, Dinoflagellates or Haptophyta. Plant cells useful in the invention include but are not limited to those from Plants transformed in accordance with the present invention may be monocots or dicots and include, but are not limited to, maize, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugar beet, sunflower, rapeseed, clover, tobacco, carrot, cotton, alfalfa, rice, potato, eggplant, cucumber, *Arabidopsis*, and woody plants such as coniferous and deciduous trees. Yeast cells useful in the invention are those from phylum Ascomycota, subphylum Saccharomycotina, class Saccharomycetes, order Saccharomycetales or Schizosaccharomycetales, family Saccharomycetaceae, genus *Saccharomyces* or *Pichia* (*Hansenula*), e.g., species: *P. anomola, P. guilliermondiii, P. norvegenesis, P. ohmeri*, and *P. pastoris*.

Cells employed in the invention may be native (non-recombinant) cells or recombinant cells, e.g., those which are transformed with exogenous (recombinant) DNA having one or more expression cassettes each with a polynucleotide having a promoter and an open reading frame encoding one or more enzymes useful for oil production. The enzyme(s) encoded by the exogenous DNA is referred to as "recombinant," and that enzyme may be from the same species or heterologous (from a different species). For example, a recombinant red algal cell may recombinantly express a green algal enzyme or a plant, or other microbial, e.g., *Aspergillus* or *Saccharomyces* enzyme, or a recombinant monocot plant cell may recombinantly express an algal enzyme or another plant, or other microbial enzyme.

In one embodiment, the microbial cell employed in the methods of the invention is transformed with recombinant DNA, e.g., in a vector. Vectors, plasmids, cosmids, YACs (yeast artificial chromosomes) BACs (bacterial artificial chromosomes) and DNA segments for use in transforming cells will generally comprise DNA encoding an enzyme, as well as other DNA that one desires to introduce into the cells. These DNA constructs can further include elements such as promoters, enhancers, polylinkers, marker or selectable genes, or even regulatory genes, as desired. For instance, one of the DNA segments or genes chosen for cellular introduction will often encode a protein that will be expressed in the resultant transformed (recombinant) cells, such as to result in a screenable or selectable trait and/or that will impart an improved phenotype to the transformed cell. However, this may not always be the case, and the present invention also encompasses transformed cells incorporating non-expressed transgenes.

DNA useful for introduction into cells includes that which has been derived or isolated from any source, that may be subsequently characterized as to structure, size and/or function, chemically altered, and later introduced into cells. An example of DNA "derived" from a source, would be a DNA sequence that is identified as a useful fragment within a given organism, and that is then chemically synthesized in essentially pure form. An example of such DNA "isolated" from a source would be a useful DNA sequence that is excised or removed from said source by biochemical means, e.g., enzymatically, such as by the use of restriction endonucleases, so that it can be further manipulated, e.g., amplified, for use in the invention, by the methodology of genetic engineering. Such DNA is commonly also referred to as "recombinant DNA."

Therefore, useful DNA includes completely synthetic DNA, semi-synthetic DNA, DNA isolated from biological sources, and DNA derived from introduced RNA. The introduced DNA may be or may not be a DNA originally resident in the host cell genotype that is the recipient of the DNA (native or heterologous). It is within the scope of the invention to isolate a gene from a given genotype, and to subsequently introduce multiple copies of the gene into the same genotype, e.g., to enhance production of a given gene product.

The introduced DNA includes, but is not limited to, DNA from genes such as those from bacteria, yeasts, fungi, plants or vertebrates, e.g., mammals. The introduced DNA can include modified or synthetic genes, e.g., "evolved" genes, portions of genes, or chimeric genes, including genes from the same or different genotype. The term "chimeric gene" or "chimeric DNA" is defined as a gene or DNA sequence or segment comprising at least two DNA sequences or segments from species that do not combine DNA under natural conditions, or which DNA sequences or segments are positioned or linked in a manner that does not normally occur in the native genome of the untransformed cell.

The introduced DNA used for transformation herein may be circular or linear, double-stranded or single-stranded. Generally, the DNA is in the form of chimeric DNA, such as plasmid DNA, which can also contain coding regions flanked by regulatory sequences that promote the expression of the recombinant DNA present in the transformed cell. For example, the DNA may include a promoter that is active in a cell that is derived from a source other than that cell, or may utilize a promoter already present in the cell that is the transformation target.

Generally, the introduced DNA will be relatively small, i.e., less than about 30 kb to minimize any susceptibility to physical, chemical, or enzymatic degradation that is known to increase as the size of the DNA increases. The number of proteins, RNA transcripts or mixtures thereof that is introduced into the cell is preferably preselected and defined, e.g., from one to about 5-10 such products of the introduced DNA may be formed.

The selection of an appropriate expression vector will depend upon the host cells. An expression vector can contain, for example, (1) prokaryotic DNA elements coding for a bacterial origin of replication and an antibiotic resistance gene to provide for the amplification and selection of the expression vector in a bacterial host; (2) DNA elements that control initiation of transcription such as a promoter; (3) DNA elements that control the processing of transcripts such as introns, transcription termination/polyadenylation sequence; and (4) a gene of interest that is operatively linked to the DNA elements to control transcription initiation. The expression vector used may be one capable of autonomously replicating in the host cell or capable of integrating into the chromosome, originally containing a promoter at a site enabling transcription of the linked gene.

The invention will be described by the following non-limiting example.

Example 1

Materials and Methods

Strains and growth conditions. The cell wall-less dw15-1 (cw15, nit1, mt$^+$) strain of *Chlamydomonas reinhardtii* was obtained from A. Grossman and is referred to as the wild-type (with regard to PGD1) parental strain throughout. This strain was crossed to CC-198 (er-u-37, str-u-2-60, mt$^-$; *Chlamydomonas* Resource Center; http://www.chlamycollection.org) for genetic analysis. Cells were grown in Tris-acetate-phosphate (TAP) medium (20 mM Tris, 0.1 g/L MgSO$_4$ 7H$_2$O (0.4 mM), 0.05 g/L CaCl$_2$ 2H$_2$O (0.34 mM), 10 mL/L glacial acetic acid, 10 mM NH$_4$Cl, 1 mM phosphate and trace elements (Harris 1989)) under continuous light (70-80 µmol m-2 s-1) at 22° C. or ambient room temperature (about 22° C.) for solid media, which contained 1.5% agar. Ammonium chloride was omitted from N-depleted (TAP-N) medium. To induce TAG biosynthesis, cells were collected by centrifugation (3000×g, 4° C., 3 minutes), washed twice with TAP-N and finally resuspended in TAP-N of the same volume. For spotting on TAP-N agar, approximately 10$^6$ cells from a log-phase culture were concentrated in 5 µL.

Primary Mutant Screen.

Plasmid disruption was used to generate mutants of the wild-type parental strain dw15-1. Transformation using glass beads was performed as previously described (Kindle 1990) using the pHyg3 plasmid conferring resistance to Hygromycin B (Berthold et al. 2002). The plasmid was linearized with NdeI (all the restriction endonucleases were purchased from New England Biolabs, http://www.neb.com). After 8 hours of recovery, cells were spread onto agar-solidified TAP medium containing 10 µg/mL Hygromycin B. Colonies were picked into 96-well plates with 1.1 mL TAP medium and grown for three days. For N deprivation and induction of TAG biosynthesis, small culture droplets (about 3 µL) were transferred with a 48-pin replicator to inoculate a new 96-well plate containing TAP medium containing 0.5 mM ammonium chloride and grown for 6-7 days under continuous light (70-80 µmol m-2 s-1) at ambient room temperature (about 22° C.). For normalization within a 96-well plate, chlorophyll fluorescence was used. For this purpose 100 µL of N-deprived cells were transferred to a black 96-well plate (Black Flat Bottom Polystyrene NBS™ Microplate 3991, Corning, http://www.corning.com) and read at 455 nm excitation with an emission filter cut off >685 nm using a FLUOstar Optima 96-well plate reader (BMG Labtech, http://www.bmglabtech.com). In the same plate to visualize neutral lipids, 100 µL Nile-Red (Sigma-Aldrich; http://www.sigmaaldrich.com) stock solution (5 µg/mL in 10% methanol containing 0.04% Triton X-100) was added. The wavelength settings for Nile-Red fluorescence were 455 nm for excitation and 550-560 nm for emission. A background reading for this filter set was obtained prior to the addition of Nile-Red (cells only) and subtracted. The neutral lipid-specific signal was calculated as [(Nile-Red fluorescence—background fluorescence)/chlorophyll fluorescence]. To identify outliers in individual 96 plate sets, the Median Absolute Deviation (MAD) was determined as [1.482× median×|individual value-median|] according to (Rousseeuw and Croux 1993) and the z-score was calculated as [(individual value-median)/MAD] as previously described for another mutant screen (Lu et al. 2008). The threshold for the z-score was set at +/−3.

Genetic Analysis.

In preparation for crossing, the pgd1 mutant in the dw15-1 background and CC-198 were separately grown for five days on TAP with 4 g/L yeast extract, transferred with a sterile loop to TAP agar with 10% the normal concentration of N for two days, and then suspended at high density in test tubes with sterile water and placed on a shaker overnight. On the following day, the two cell types were combined using 0.5 mL aliquots, removed after 2-3 hours of mating and plated onto TAP medium completely lacking N and solidified with 4% agar. After one day in the light, the zygote plates were moved to the dark. Five days after mating, zygospores were sampled as described by Harris (Harris 1989). On the day following transfer of the zygospores to normal TAP solidified with 2% agar, meiotic progeny were identified under a dissecting microscope and separated with a glass needle. After 7 days, the colonies were sufficiently large to transfer to nonselective media for subsequent replica-plating.

DNA and RNA Techniques.

Genomic DNA of *Chlamydomonas* was prepared according to (Newman et al. 1990). For Southern blotting, genomic DNA was digested with BamHI and resolved by agarose gel electrophoresis (10 μg DNA per lane). DNA was transferred to a nylon membrane (Amersham Hybond N+, GE Healthcare, http://www.gelifesciences.com) and fixed under ultraviolet light. Digoxigenin (DIG) labeling of the probe, DNA transfer, and signal detection were performed using a kit from Roche (http://www.roche.com) following the manufacturer's instructions. The probe was generated through PCR amplification of a 234 bp region within the hygromycin B resistance cassette with primers SF and SR (all primer sequences can be found in Table 1).

For genotyping and "SiteFinding" PCR (Tan, G. H. et al. 2005), Taq polymerase (Invitrogen, http://www.invitrogen.com) was used. For genotyping, the PCR conditions were according to the protocol provided by Invitrogen with primers F1, S2-1, and R. SiteFinding PCR was conducted according to (Tan, G. H. et al. 2005) with minor modifications and with primers optimized for the pHyg3 plasmid. The primers used for finding the insertion in PGD1 were: SiteFinder6 in combination with S1-1 and S1-2, SiteFinder8 in combination with S2-1 and S2-2. In addition, nested primers SFP1 and SFP2 were used for both combinations.

RNA was isolated using the RNeasy Plant Mini Kit (Qiagen, http://www.qiagen.com) according to the manufacturer's instructions. To obtain cDNA as the template for RTPCR, RNA was subjected to reverse transcription with Superscript II reverse transcriptase (Invitrogen). For real-time PCR, the commonly used reference gene RACK1 was employed for normalization using previously reported primers (Chang et al. 2005). Primers used for PGD1 were qF and qR. Data were analyzed with the 2(-ΔΔC(T)) method (Livak and Schmittgen 2001).

TABLE 1

Oligonucleotide primers used in this study.
All primer sequences are written in
5' to 3' direction.

| Name | Sequence |
|---|---|
| SF | ACCAACATCTTCGTGGACCT (SEQ ID NO: 4) |
| SR | CTCCTCGAACACCTCGAAGT (SEQ ID NO: 5) |
| SiteFinder6 | CACGACACGCTACTCAACACACCACCTCGCACAGCGTCCT CAAGCGGCCGCNNNNNNGCAT (SEQ ID NO: 6) |
| SiteFinder8 | CACGACACGCTACTCAACACACCACCTCGCACAGCGTCC TCAAGCGGCCGCNNNNNNGCAG (SEQ ID NO: 7) |
| SFP1 | CACGACACGCTACTCAACAC (SEQ ID NO: 8) |
| SFP2 | ACTCAACACACCACCTCGCACAGC (SEQ ID NO: 9) |
| S1-1 | ACTGCTCGCCTTCACCTTCC (SEQ ID NO: 10) |
| S1-2 | CTGGATCTCTCCGGCTTCAC (SEQ ID NO: 11) |

TABLE 1-continued

Oligonucleotide primers used in this study.
All primer sequences are written in
5' to 3' direction.

| Name | Sequence |
|---|---|
| S2-1 | ATAGGGGTTCCGCGCACAT (SEQ ID NO: 12) |
| S2-2 | CCGAAAAGTGCCACCTGAC (SEQ ID NO: 13) |
| S3 | GTCATCCCATGGAAGCTTGG (SEQ ID NO: 14) |
| F1 | ACATCGTGAATGGCAAAACA (SEQ ID NO: 15) |
| R | ATTGCGCGGGTTTAGAACTT (SEQ ID NO: 16) |
| qF | AGCCAGCTATTGTCGCACTT (SEQ ID NO: 17) |
| qR | CAAGAAATCCGCTGACATCC (SEQ ID NO: 18) |
| CF1 | TATCCATATGACGTTCCAGATTACGCTGCTCAGTGCGGCC GCATGAGCCAGCTATTGTCG (SEQ ID NO: 19) |
| CR1 | GAATTTCGACGGTATCGGGGGGATCCACTAGTTCTAG CTAGATCACCGGCAGGCGTGTGG (SEQ ID NO: 20) |
| CF2 | GGATCCGATGAGCCAGCTATTGTCG (SEQ ID NO: 21) |
| CR2 | GTCGACCCGGCAGGCGTGTGGGTC (SEQ ID NO: 22) |
| CF3 | AAAGAGGCGCGTCATGAGCCAGCTATTGTCG (SEQ ID NO: 23) |
| CR3 | CGGAAGGCGCGTCACCGGCAGGCGTGTGG (SEQ ID NO: 24) |

N indicates a random nucleotide.

For expression of PGD1 in *E. coli*, cDNA was originally amplified with primers CF1 and CR1 using the Failsafe PCR Kit from Epicentre (http://www.epibio.com). The PCR product was then integrated into the NotI-linearized yeast vector pMK595 (Luo et al. 2010) by homologous recombination in *Saccharomyces cerevisiae* (Ma et al. 1987). The fusion plasmid was recovered by transforming *E. coli* with yeast DNA extract and designated pXL1238. This plasmid was then used as a template for PCR using primers CF2 and CR2 and Phusion polymerase (New England Biolabs) to generate a fragment with BamHI and SalI sites. The PCR product was ligated into pCR-Blunt (Invitrogen) and cut out with BamHI and SalI. This fragment was ligated into pLWO1-DsRed (Lu and Benning 2009) to generate plasmid pXL1256. pXL1256 was sequenced and mutations were found. The mutated region was removed by restriction digestion and the remaining backbone was ligated with digested RT-PCR product of that region to obtain plasmid pXL1262. Another PCR was performed to amplify PGD1 cDNA from pXL1262 using primers CF3 and CR3. PCR product and an expression vector pMK1006 (provided by M.-H. Kuo) were combined using a ligation independent cloning procedure (Aslanidis and de Jong 1990) and sequenced for confirmation. In this plasmid, PGD1 expression was under the control of a T7 promoter and the resulting fusion protein was N-terminally tagged with poly-histidine.

Mutant Complementation.

A co-transformation protocol was used to introduce wild-type sequences into the pgd1 mutant in the dw15-1 (nit-) background. Plasmid pMN24 (Fernandez et al. 1989) containing the *Chlamydomonas* nitrate reductase gene NIT1 as selection marker was digested with BamHI and used for glass bead transformation of the pgd1 mutant. A bacterial artificial chromosome (BAC) 5E6 containing wild-type genomic DNA was obtained from the Clemson University Genomics Institute (http://www.genome.clemson.edu), and was digested with KpnI and AseI to excise a 9.5 kb fragment containing the PGD1 genomic DNA. In each transformation, 0.25 µg linearized pMN24 and 0.3 µg gel purified BAC fragment were used. TAP plates containing 0.5 mM nitrate instead of 10 mM ammonium were used for selection. The nitrate served initially as the nitrogen source and the low concentration led eventually to conditions of N deprivation and chlorosis of the pgd1 mutant but not complemented lines or the wild-type parental control. After transformation of pgd1 with pMN24, colonies from non-complemented lines formed and bleached within approximately three weeks when grown under continuous light (70-80 µmol m-2 s-1) at ambient room temperature (about 22° C.). Complemented lines forming green colonies were re-streaked and maintained on agar-solidified TAP medium with 10 mM nitrate as the sole N source to avoid growth of potentially contaminating non-transformed cells.

Lipid Analysis and Pulse-Chase Labeling.

Lipid extraction, thin-layer chromatography (TLC) of neutral lipids, transesterification and gas-liquid chromatography were done according to (Moellering and Benning 2010). Briefly, lipids were extracted from cell pellets with methanol, chloroform, 88% formic acid (2:1:0.1 by volume). To the extract 0.5 volume of 1M KCl, 0.2 M H3PO4 was added, mixed and phases were separated by low speed centrifugation. For TAG quantification, lipids were resolved by TLC on Silica G60 plates (EMD chemicals, #5721-7, http://www.emdchemicals.com) developed in petroleum ether-diethyl ether-acetic acid (80:20:1 by volume). Polar lipids were separated on the same plate using chloroform-methanol-acetic acid-$H_2O$ (75:13:9:3 by volume) as solvent. To analyze lyso-glycolipids during for the PGD1 assay, acetone-toluene-$H_2O$ (91:30:7.5 by volume) was used, instead. Brief exposure to iodine vapor was employed for visualization of lipids. Transesterification of each lipid and separation of fatty acid methyl esters by GLC were as previously described (Rossak et al. 1997). Transesterification was conducted on pellets with a known number of cells to determine the cellular total fatty acid content. Staining with α-naphtol (Benning et al. 1995) was used for the PGD1 assay to detect galactoglycerolipids.

For pulse-chase labeling experiments, cells were grown to log phase in TAP medium and either used directly (FIG. 12), or transferred to TAP-N medium and grown for 12 hours to induce N deprivation. Cells were harvested and resuspended at a concentration of $3-8×10^8$ per mL either in modified TAP (FIG. 12) or TAP-N medium (FIG. 6 and FIG. 13) containing 6 mM acetate (normal TAP contains 17.5 mM). To these cultures [$^{14}$C-U]-acetate (specific activity 45-60 mCi/mmol; Perkin Elmer, http://www.perkinelmer.com) was added to provide 1 µCi/mL. In a typical experiment after 1-4 hours of incubation in the light 20-40% of the labeled acetate was incorporated as determined by liquid scintillation counting. At the end of the pulse labeling phase, cells were centrifuged and washed to remove the labeled acetate, and cells were resuspended in TAP-N containing the normal amount of acetate to initiate the chase phase. Lipid extracts were prepared as described above, split in half, and analyzed for polar lipids DGTS, PtdEtn, MGDG, DGDG, PtdGro, and a mixture of SQDG and PtdIns, which could not be individually analyzed due to their low total amount in this experiment. Material at the origin of the TLC was also analyzed and included. The other half of the sample was analyzed for non-polar lipids DAG and TAG. Lipids were isolated from the TLC plates and incorporation of label into each lipid was quantified by scintillation counting. These lipid fractions were summed up and percentages for each lipid fraction were calculated.

Recombinant Protein Production and PGD 1 Assay.

BL21 (codon+) E. coli strains harboring the empty pMK1006 vector or the pMK1006-PGD1 construct were grown to log phase at 37° C. Isopropyl-β-D-thiogalactopyranoside was added to the final concentration of 0.5 mM to induce protein production. Cells were harvested after 3 hours of induction. To extract proteins, cells were resuspended in lysis buffer (20 mM Tris-HCl, pH 7.9, 10% glycerol, 150 mM NaCl, 1 mM dithiothreitol). The mixture was then frozen in liquid nitrogen and thawed at room temperature for three cycles and sonicated to lyse cells. Lysates were centrifuged at 21,000×g for 15 minutes to obtain inclusion bodies. Inclusion bodies were washed with 5 mL/g wash buffer (4 M urea, 0.5 M NaCl, 1 mM EDTA, 1 mg/ml sodium deoxycholate, 50 mM Tris-Cl pH 8.0) twice and denatured with solubilization buffer (8 M urea, 50 mM Tris-Cl pH 8.0, 10 mM dithiothreitol) by incubation at 50° C. for 20 min. Supernatant was collected after centrifugation at 21,000×g for 30 minutes and subjected to Ni-NTA affinity purification as described before (Lu and Benning 2009). His-tagged PGD1 protein was eluted with solubilization buffer containing 200 mM imidazole. Aliquots of purified proteins were diluted in 15 different buffers of the QuickFold Kit (AthenaES http://www.athenaes.com/), assayed for lipase activity, and 40× dilution into protein refolding buffer (50 mM Tris-Cl pH 8.5, 9.6 mM NaCl, 0.4 mM KCl, 1 mM EDTA, 0.5 M arginine, 0.75 M Guanidine-HCl, 0.05% polyethylene glycol 3350, 1 mM dithiothreitol) was found to be optimal for PGD1. After 1 hour incubation at 4° C., proteins were aliquoted and kept frozen at −80° C. Protein concentration was determined with Bio-Rad Protein Assay Dye Reagent Concentrate (http://www.bio-rad.com) according to the manufacturer's instructions.

To prepare lipid substrates from Chlamydomonas or E. coli cells, lipids were extracted from 48 hours N-deprived Chlamydomonas cells or IPTG induced E. coli cells expressing cucumber MGDG synthase (Shimojima et al. 1997) and resolved by polar TLC. Corresponding bands were isolated and lipids were recovered from silica gel by extraction with chloroform-methanol (1:1 by volume). For each PGD1 reaction, 75 nmol lipid substrates extracted from Chlamydomonas, or E. coli cells expressing the cucumber MGDG synthase were used. The organic solvent was removed under an N2 stream and the lipids were resuspended in 350 µL 0.1M phosphate saline buffer (PBS; pH 7.4) with 4.28 mM Triton X-100 and dispersed by sonication (Sonicator 3000 with microprobe, Misonix, http://www.misonix.com) for 6×10 s (power setting 1.5) on ice. Then 100 µL additional PBS was added. Per assay 10 µg refolded PGD1 protein (quantified as stated above) in 50 µL protein refolding buffer was added. As a negative control, 50 µL protein refolding buffer only was added. The PGD1 refolding buffer inhibited Rhizopus lipase (Sigma-Aldrich). Therefore, 10 µg lipase dissolved in 50 µL PBS instead of protein refolding buffer was used unless otherwise noticed. Dithiothreitol was added to a final concentration of 1 mM from a freshly prepared stock solution. The mixture was sonicated again for 5 seconds and incubated at ambient temperature (~22° C.). After 6 hours incubation (3 hours for Rhizopus lipase to prevent potential loss of lyso-lipid standards), reactions were stopped by the addition of 1 mL solvent used for lipid extraction, and lipid extracts were analyzed by TLC described above. For gas chromatograms on free fatty acids and lyso-MGDG generated by PGD1, 9 hours was used to obtain more prominent signals. To measure the velocity of MGDG hydrolysis, reactions were quenched after 3 hours of incubation.

Positional Analysis of TAG.

Positional analysis of TAG was performed with *Rhizopus* lipase using a similar procedure as described above. Briefly, lipids were extracted from 48 hours N-deprived *Chlamydomonas* cells and resolved by neutral TLC. TAG was extracted from silica gel with chloroform-methanol (1:1 by volume) as above. Approximately 10 μg was dried under an N2 stream and resuspended in PBS containing Triton X-100 as above. *Rhizopus* lipase was dissolved in PBS and 20 μg was added to the emulsified TAG preparation. Lipids were extracted from the reaction mixtures and resolved by neutral lipid TLC (described above). Free fatty acids and monoacylglycerol spots were scraped for transesterification as above. Background levels of fatty acids carried over with *Rhizopus* lipase were estimated in a control reaction without substrate lipid supplied, and subtracted from the free fatty acids data obtained with substrate.

Chlorophyll, Viability and TBARS Analyses.

Chlorophylls were extracted from fresh cell pellets with 80% acetone and concentrations were calculated from the absorbance values at 647 nm and 664 nm according to (Zieger and Egle 1965). To assess cell viability, cells were grown in liquid cultures of TAP or TAP-N. On days 0, 2, 4, and 7 a set volume of culture was diluted and spread onto agar-solidified TAP medium supplemented with 0.4% yeast extract. Colony forming units were counted one week later. Cells from a second aliquot were fixed in 3.7% formaldehyde (in water) and counted using a hemocytometer under a microscope. Viability percentages (colonies formed per total cells counted each day) were normalized to the values on day 0. TBARS were prepared by extraction with thiobarbituric acid/trichloroacetic acid solution (0.3% and 3.9% respectively) and determined by measuring absorbance at 532 nm as previously described (Baroli et al. 2003). The extinction coefficient used was 155 mM$^{-1}$ cm$^{-1}$.

Results

Isolation of TAG Mutants.

To generate *Chlamydomonas* mutants with altered TAG content, random, insertional gene-disruption was conducted by introducing a linearized pHyg3 plasmid (Berthold et al. 2002) into the cell wall-less *Chlamydomonas* strain dw15-1, which is referred to as the parental wild-type strain (because it is wild-type with regard to its lipid content and synthesis). Hygromycin B-resistant transgenic lines were picked into a 96-well plate and induced for TAG accumulation by transfer to low-N medium. During the primary screen, Nile-Red fluorescence-staining of neutral lipids (Chen et al. 2011, Kimura et al. 2004) was used to monitor neutral lipids in a high-throughput mode using a 96-well plate reader. Putative mutants differing in Nile-Red fluorescence from the wild-type parental strain based on statistical criteria as defined under Materials and Methods were reanalyzed by extracting lipids, separating them by thin-layer chromatography (TLC), followed by quantification of TAG-derived fatty acid methylesters by gas liquid chromatography (GLC). Of 34,000 independent transgenic lines generated, 80 were initially found to exhibit an altered Nile-Red fluorescence intensity, of which six mutants with robust and reproducible changes in TAG levels were eventually isolated. The focus here is on the characterization of one of the low-TAG mutants, initially designated line E12. After in-depth analysis it was renamed plastid galactoglycerolipid degradation 1 (pgd1), the designation used from here on.

the Pgd1 Mutant has Reduced TAG and Becomes Chlorotic Following N Deprivation.

Over the course of three days following N deprivation the pgd1 mutant showed an approximately 50% reduction in the ratio of fatty acids in TAG over total fatty acids in the lipid extract, a parameter that allows a robust comparison of relative TAG content between different lines, in this case pgd1 and the wild-type parental strain dw15-1 (FIG. 1A). Because non-homologous integration of linearized plasmids into the *Chlamydomonas* genome can potentially occur multiple times in a single line, genetic linkage of the Hygromycin B resistance and the lipid phenotype were examined to confirm insertional tagging of the gene responsible for the lipid phenotype, a prerequisite for subsequent gene identification. Towards this end, the pgd1 mutant was crossed with CC-198, a cell-walled strain (mating type-) and close relative of dw15-1, which is mating type+ and the wild-type parental strain of pgd1. Strains CC-198 and dw15-1 were compared for their lipid composition, but did not show major differences in TAG content. The ratio of fatty acids in TAG over total fatty acids in extracts was 0.46±0.04 for dw15-1 and 0.51±0.04 for CC-198. A total of 83 meiotic progeny lines were analyzed, of which 40 were resistant and 43 sensitive to Hygromycin B. The observed ratio approached the hypothetical 2:2 segregation ratio suggesting a single plasmid insertion in the genome, although the statistical limitations of the experiment would allow for multiple, but very tightly linked, plasmid insertions. Lipid analysis was performed on 14 progeny lines (FIG. 1B) and the results were compared to the wild-type parental strain and pgd1. The TAG fatty acid over total fatty acid ratio of the eight Hygromycin B sensitive lines was similar to that of the parental strain, while the six resistant lines showed a ratio similar to that of the original pgd1 mutant. Thus, the Hygromycin B resistance marker appeared to be closely linked to the mutation causing the lipid phenotype.

Figure 10:
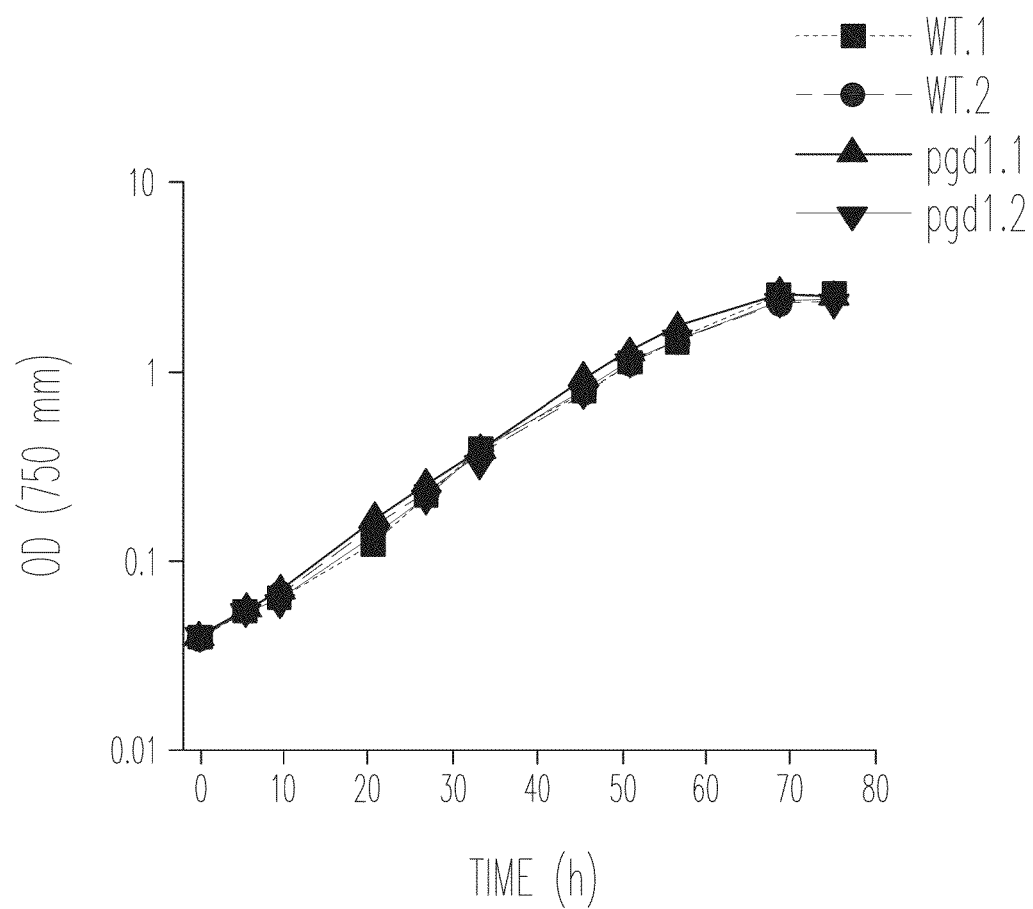
FIG. 10. Growth curves of wild-type parental strain (WT) and pgd1 mutant in regular TAP medium. Cells were grown to stationary phase and inoculated into fresh TAP medium to an optical density (at 750 nm) of 0.04. This experiment was repeated more than three times with two biological replicates each time. A representative result is shown here. Each data point is the average from three technical replicates with relative standard deviations smaller than 3%.

In addition to TAG deficiency, pgd1 cells gradually developed chlorosis and fully bleached over the course of 12 days following N depletion (FIG. 1C), which was accompanied by reduced cell viability (see below). However, in N-replete medium there was no discernible difference in growth between the wild-type parental strain and pgd1 (FIG. 10). Thus, the ability to produce or maintain TAG seems to be required for the long-term viability of the cells following N deprivation, which provides a clue towards a physiological role of TAG accumulation under nutrient stress that will be further explored below.

The Pgd1 Lipid Phenotype is Caused by Disruption of a Putative Lipase Gene.

Figure 2:
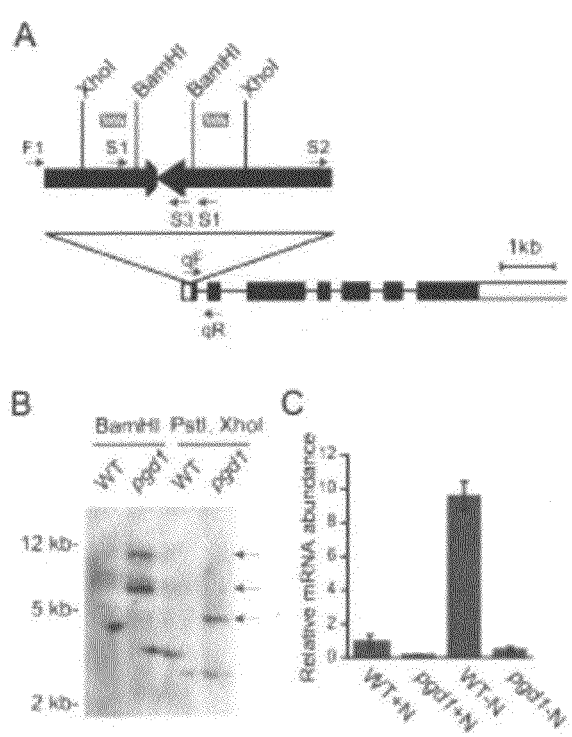
FIG. 2. Molecular characterization the pgd1 mutant. (A) A schematic representation of the pHyg3 insertion into the genome of the pgd1 mutant. The triangle represents the insert. Thick arrows indicate the orientation of the positive strand of the aph7" gene conferring resistance to Hygromycin B. The PGD1 gene model is shown in a 5' to 3' direction from left to right, with exons and introns represented by black boxes and connecting lines, respectively. 5' and 3' untranslated regions are shown as white boxes. Crosshatched boxes indicate the position of the Southern probe used in (B). PCR primer sites are indicated by arrows, which are not drawn to scale. The binding sites for the "SiteFinding" primers and nested primers for the two ends of the insertion are shown as single arrows S1 and S2, respectively. Sequences for all primers can be found in Table 1. (B) Southern blot of the pHyg3 insertion and surrounding genomic DNA. Genomic DNA was digested with BamHI or PstI and XhoI and probed with the fragment (cross-hatched box) as shown in (A). PstI cuts outside the insert and sites are not shown in (A). (C) Reverse transcription-quantitative PCR of the PGD1 transcript in the wild-type parental strain (WT) and the pgd1 mutant grown for 48 h in TAP (+N) or TAP-N(—N) medium. The abundance of PGD1 mRNA was normalized to RACK1. Data are presented as average±SD (n=3).

To identify the plasmid insertion site, "SiteFinding" PCR (polymerase chain reaction) (Tan et al. 2005) was employed. Random primers combined with primers annealing to the positive strand of the Hygromycin B resistance gene (aph7") on the pHyg3 plasmid (FIG. 2A, primer S1) generated two partial pHyg3 plasmid sequences present in opposite orientations as depicted in FIG. 2A, but no bona fide genomic flanking DNA. Probing a Southern blot of BamHI-digested pgd1 genomic DNA with a pHyg3 fragment as indicated in FIG. 2A, two signals were observed (FIG. 2B), while only one would be expected for a single insertion due to the presence of a single BamHI site in pHyg3. However, probing pgd1 genomic DNA double-digested with PstI (no site in pHyg3) and XhoI (single site in pHyg3) with the same probe, a single band was present (FIG. 2B). Together, these data suggested that two pHyg3 fragments were present in opposite orientations at the pgd1 locus. No true signal was obtained from genomic DNA of the wild-type parental strain (FIG. 2B).

Through "SiteFinding" PCR with plasmid-specific, nested primers S2-1 and S2-2 complementary to the other end of pHyg3 (FIG. 2A, S2), a flanking genomic DNA (to the right side of the insertion as shown in FIG. 2A) was amplified. Sequencing indicated that one end of the insertion bordered sequences within the predicted untranslated region of a gene previously annotated as CGLD15 (Conserved in Green Lineage and Diatoms 15; *Chlamydomonas* v5.3 genome in the Phytozome database, http://www.phytozome.net/) on chromosome 3 (position 6320421-6327099; gene locus Cre03.g193500) (Merchant et al. 2007), which we designated PGD1 based on functional analysis presented below. A conserved catalytic triad of Ser-Asp-His was predicted for the translated protein sequence of this gene, which is a typical motif for hydrolases such as lipases (acyl hydrolases). The flanking genomic sequence on the left side of the insertion (refer to FIG. 2A) was obtained by PCR with primers F1 and S3 (FIG. 2A). Sequence analysis of this fragment showed that the insertion was accompanied by the deletion of 14 bp of genomic sequence that is unlikely to affect the neighboring gene 5' to PGD1. Based on these analyses, PGD1 was considered the most likely affected gene in the pgd1 mutant responsible for the observed lipid phenotype.

Insertions into the promoter or untranslated region of PGD1 were expected to affect gene expression. Quantifying PGD1 transcript levels by real-time PCR (FIG. 2C) showed greatly reduced expression of this gene in the pgd1 mutant. The real time PCR results also confirmed the increased expression of the PGD1 gene in the wild-type parental strain following N deprivation previously observed during global transcript analysis (Miller et al. 2010). The up-regulation of PGD1 expression following N deprivation in parallel with TAG accumulation suggested that the gene product might play a role in TAG biosynthesis.

Figure 3:
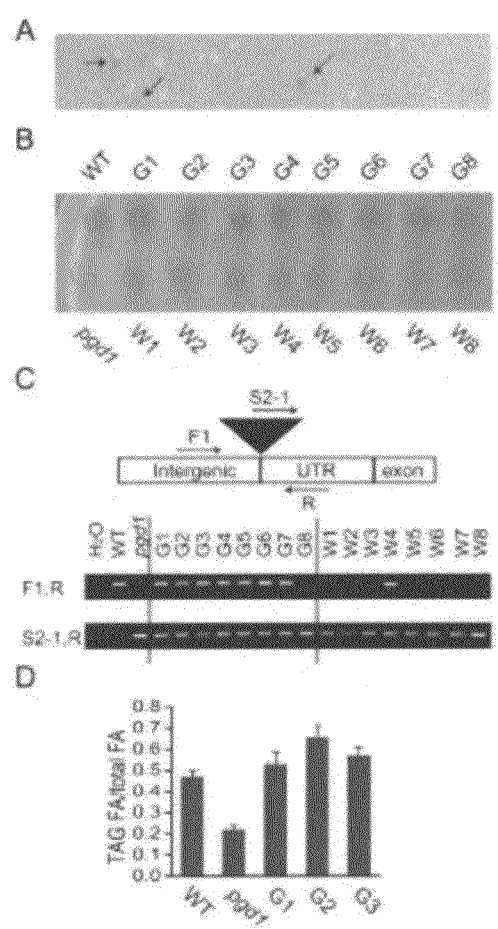
FIG. 3. Genetic complementation of pgd1 phenotypes with wild-type genomic DNA. (A) Section of an agar plate with pgd1 mutant colonies 20 days after transformation with a wild-type PGD1 containing fragment. Green colonies (arrows) are presumed to be complemented lines; white colonies show the chlorosis phenotype characteristic of pgd1. (B) Confirmation of the phenotypes of lines which form green (G1-8) and bleached colonies (W1-8) following re-streaking and 10 d of growth on TAP-N. The pgd1 mutant and the wild-type parental strain (WT) are included. (C) Genotyping of the different lines. A scheme depicting the insertion site shows the primer locations with arrows; sections of DNA gels with PCR products obtained with PCR primers as indicated are shown below. Primer sizes are not to scale. (D) Quantitative analysis of TAG of three lines rescued with PGD1 genomic DNA after 48 h of growth in TAP-N medium. The ratio of fatty acids (FA) in TAGs over total fatty acids in the lipid extracts is shown. Averages of three independent measurements are provided. Error bars indicate standard deviation.

To independently confirm that the phenotypes of the pgd1 mutant were indeed caused by the insertion into PGD1 described above, complementation analysis with a PGD1-containing fragment from the bacterial artificial chromosome (BAC) clone, 5E6 (Grossman et al. 2003), was conducted. The fragment used for transformation contained 2 kb 5' and 1 kb 3' of the predicted PGD1 gene and was devoid of other predicted open reading frames. The pMN24 plasmid (Fernandez et al. 1989) containing the NIT1 gene encoding nitrate reductase was used in a co-transformation experiment for selection on agar plates with nitrate as the N source. (Note, the parental wild-type strain dw15-1 as well as pgd1 carry a mutation in the genomic NIT1 gene). To screen for DNA fragments rescuing the observed chlorosis phenotype of pgd1 on N-limited medium, we developed a "Single Step N Deprivation-Colony Color Screen" method. Agar plates containing 0.5 mM instead of 10 mM nitrate were used for selection allowing colonies to form, which then became N-deprived as nitrate was depleted. Under these conditions, pgd1 mutant colonies turned from green to white within three weeks while colonies of the wild-type parental strain or pgd1 colonies harboring an introduced wild-type copy of the PGD1 gene were expected to remain green (FIG. 3A). When the PGD1 genomic fragment was co-transformed with the NIT1 marker, approximately 5-10% colonies remained green. This frequency is at the lower end of the range for previously reported co-transformation efficiencies (Kindle 1990). Eight colonies scored as green and another eight colonies scored as white were chosen and the phenotype was confirmed by spotting cells onto —N agar plates (FIG. 3B). Genotyping was performed on the junction of the plasmid insertion to confirm the presence of the gene disruption typical for the pgd1 mutant (FIG. 3C). Primers F1 and R were expected to give a signal specific for PGD1 either in the genome or introduced through the fragment, while primers S2-1 and R were expected to give a signal specific for pgd1. According to this reasoning, seven of the eight green lines (G1-G7) and one of the white lines (W4) contained the wild-type PGD1 gene (FIG. 3C). The presence of a signal from a combination of S2-1 and R indicative of the presence of the pgd1 background ruled out contamination by the parental strain. It seems likely that in outlier G8 a secondary mutation caused the observed suppressor phenotype and in outlier line W4 the introduced PGD1 gene was either mutated, not adequately expressed, or silenced. Quantitative lipid analysis of three green colony-forming lines (G1-3) showed that they regained their ability to accumulate TAGs to similar levels as the parental strain (FIG. 3D).

Extraplastidic Lipids of Pgd1 are Affected in a Consistent Way.

Figure 4:
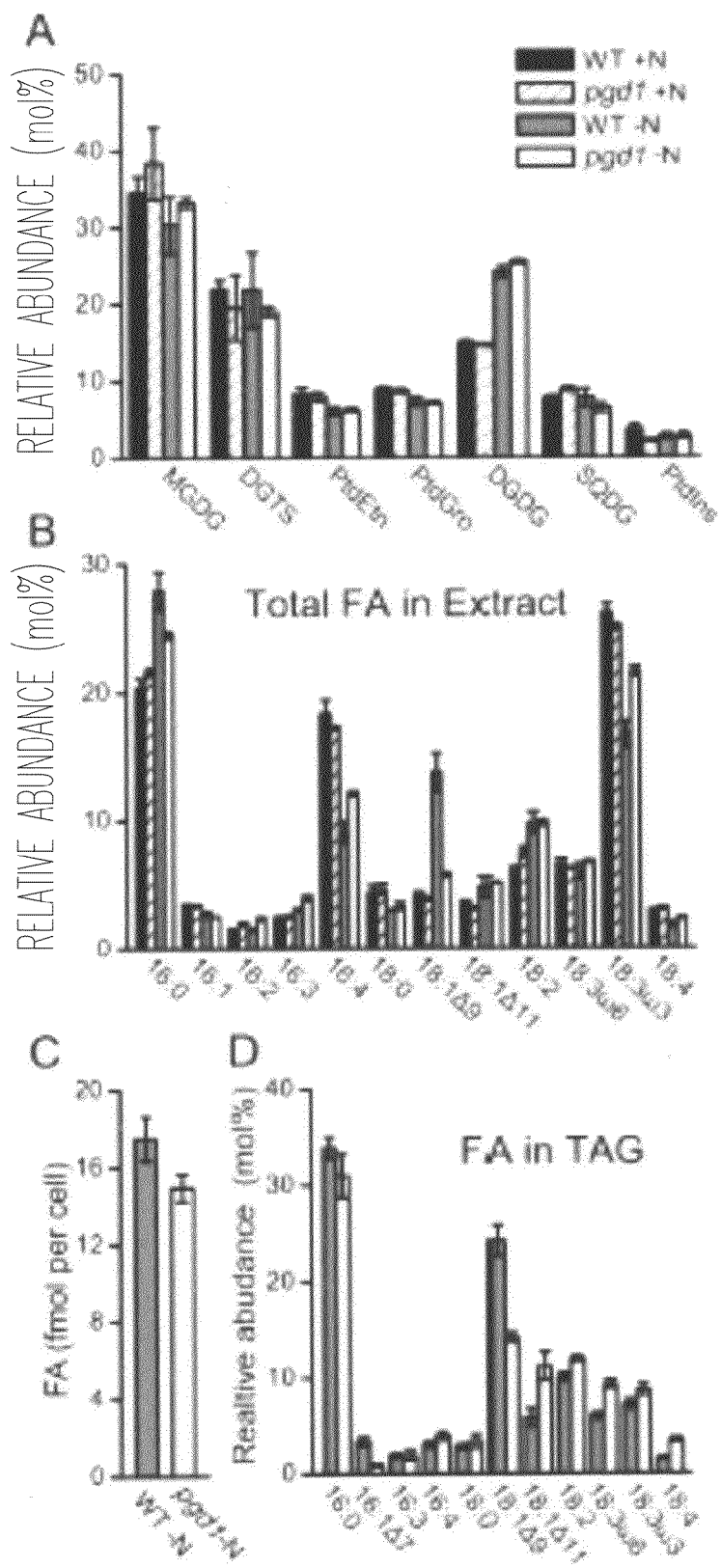
FIG. 4. Detailed lipid analysis of the wild-type parental strain (WT) and pgd1 mutant in N-replete medium (+N) and 48 h after transfer to N-depleted medium (—N). (A) Relative abundance of major polar lipid classes. (B) Relative fatty acid (FA) composition and (C) cellular contents of total cellular fatty acids. (D) Composition of fatty acids esterified to TAG. Averages of three replicates are shown with error bars indicating SD. Lipid abbreviations: DGTS, diacylglycerol-N,N, N-trimethylhomoserine; DGDG, digalactosyldiacylglycerol; MGDG, monogalactosyldiacylglycerol; PtdEtn, phosphatidylethanolamine; PtdGro, phosphatidylglycerol; PtdIns, phosphatidylinositol; SQDG, sulfoquinovosyldiacylglycerol. Fatty acids are designated as chain length: number of double bonds. Positions of double bonds are indicated with Δ (counting from carboxyl group) or ω (counting from the methyl group). In (B) 16:2 is a mixture of 16:2 Δ7,10 and 16:2 Δ10,13.

The fact that disrupting PGD1 led to lower TAG content argues against its gene product's role as a TAG lipase, because decreased TAG lipase activity in the mutant would be expected to increase TAG content. An alternative hypothesis was that PGD1 releases acyl groups from membrane lipids. The activation of the released fatty acids by formation of acyl-CoAs would then make them available for TAG synthesis. To identify the lipid substrates for such a presumed lipase, the abundant membrane lipids DGTS, phosphatidylethanolamine (PtdEtn), monogalactosyldiacylglycerol (MGDG), digalactosyldiacylglycerol (DGDG), phosphatidylglycerol (PtdGro), sulfoquinovosyldiacylglycerol (SQDG), and phosphatidylinositol (PtdIns) were analyzed in the wild-type parental strain and pgd1 grown on N-replete and N-depleted medium for 48 hours (FIG. 4A). The relative fraction of DGDG increased following N deprivation as recently reported (Fan et al. 2011). However, no statistically significant difference between the relative amounts of the respective membrane lipid classes for the wild-type parental strain and the pgd1 mutant was observed.

Figure 11A:
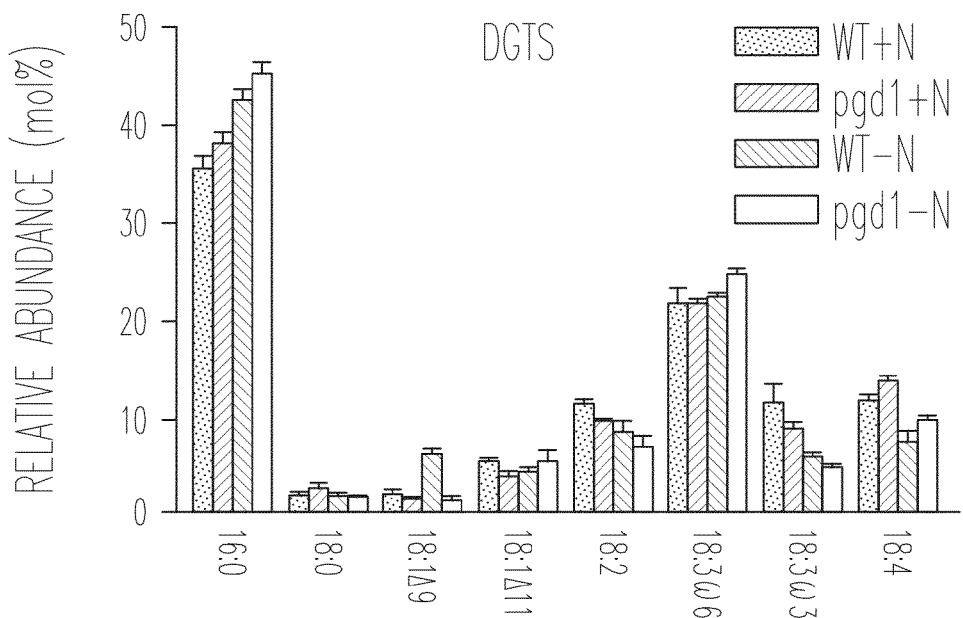
FIG. 11. Fatty acid compositions of DGTS, PtdEtn, MGDG, DGDG, PtdGro of the wild-type parental strain (WT) and pgd1 mutant in N-replete medium (+N) and 48 h after transfer to N-depleted medium (—N). Lipid abbreviations are as defined for FIG. 4. Averages of three replicates are shown with error bars indicating SD. Fatty acids are designated as chain length: number of double bonds. Positions of double bonds are indicated with Δ (counting from carboxyl group) or ω (counting from the methyl group).
Figure 11B:
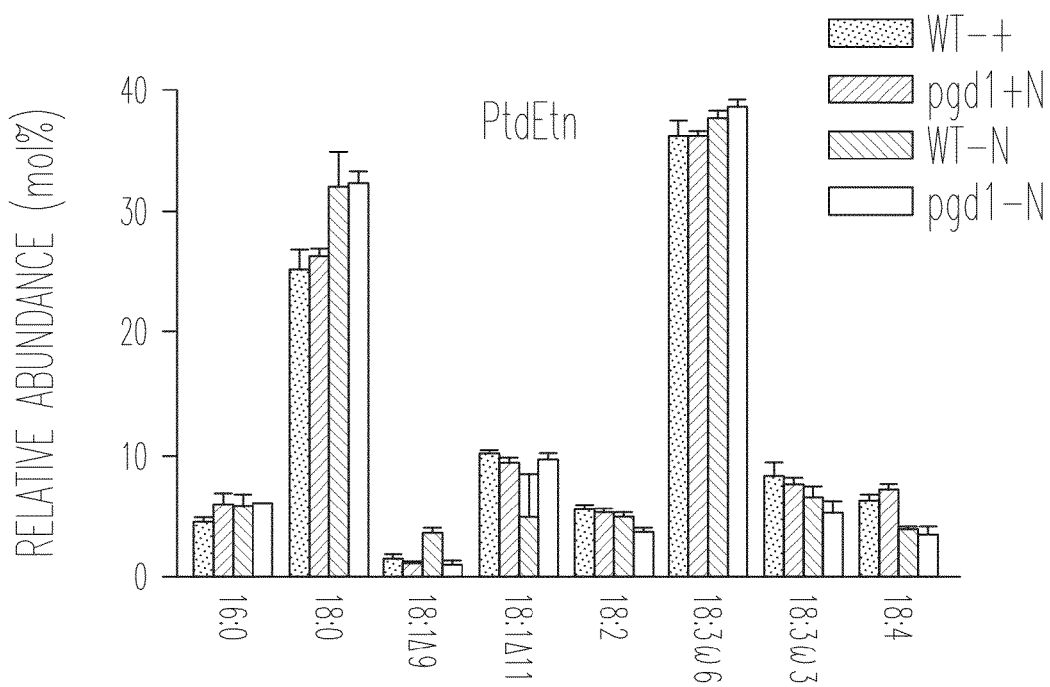

Although relative amounts of membrane lipid classes were not altered under the growth conditions used, it seemed possible that specific molecular species within each lipid class represented by differences in the respective acyl group substituents were altered in the mutant. For example, changes in fatty acid profiles of glycerolipids have been diagnostic in determining whether the ER or plastid pathways of lipid assembly were affected in the respective mutants of *Arabidopsis* (Kunst et al. 1988, Xu et al. 2003). Overall the decreased TAG content in pgd1 was reflected by a reduced total amount of fatty acids per cell (FIG. 4C), raising the question of whether specific TAG molecular species were missing in pgd1 consistent with the disruption of one of several hypothetical TAG assembly pathways. Indeed, the total fatty acid profile of pdg1 was altered. Most prominently the relative fraction of oleate (18:1$^{\Delta 9}$; number of carbons: number of double bonds and position of double bonds from the carboxyl end) was reduced (FIG. 4B). Following N deprivation the wild-type parental strain showed an increase in the relative amount of oleate that was not observed for pgd1, while the acyl composition of pgd1 was indistinguishable from that of the parental strain under N-replete growth conditions (FIG. 4B). When the fatty acyl group profile of individual lipids following N deprivation was examined, a decrease in oleate was observed for pgd1 not only in TAG (FIG. 4D), but also in DGTS (FIG. 11A) and PtdEtn (FIG. 11B). The latter two are presumed to be extraplastidic membrane lipids (Giroud et al. 1988, Giroud and Eichenberger 1989), while the exclusive location of TAG in cytosolic lipid droplets has recently been questioned (Fan et al. 2011, Goodson et al. 2011). Oleate accounts for approximately 25% of the acyl groups in TAG, but only up to 10% in DGTS or PtdEtn explaining why a loss of a specific molecular species containing this fatty acid has more drastic effects on overall TAG content than on that of DGTS and PtdEtn. The plastid lipids MGDG (FIG. 11C), DGDG (FIG. 11D), and PtdGro (FIG. 11E), were not altered in their acyl composition. As apparently only extraplastidic lipids are affected in the pgd1 mutant, it seems possible that PGD 1 activity affects the export of acyl groups from the plastid or the assembly of extraplastidic lipids, assuming that the fraction of TAG missing in pgd1 is extraplastidic.

Oleate is Decreased in the sn-1 and sn-3 Position of TAGs in pgd1.

Figure 5:
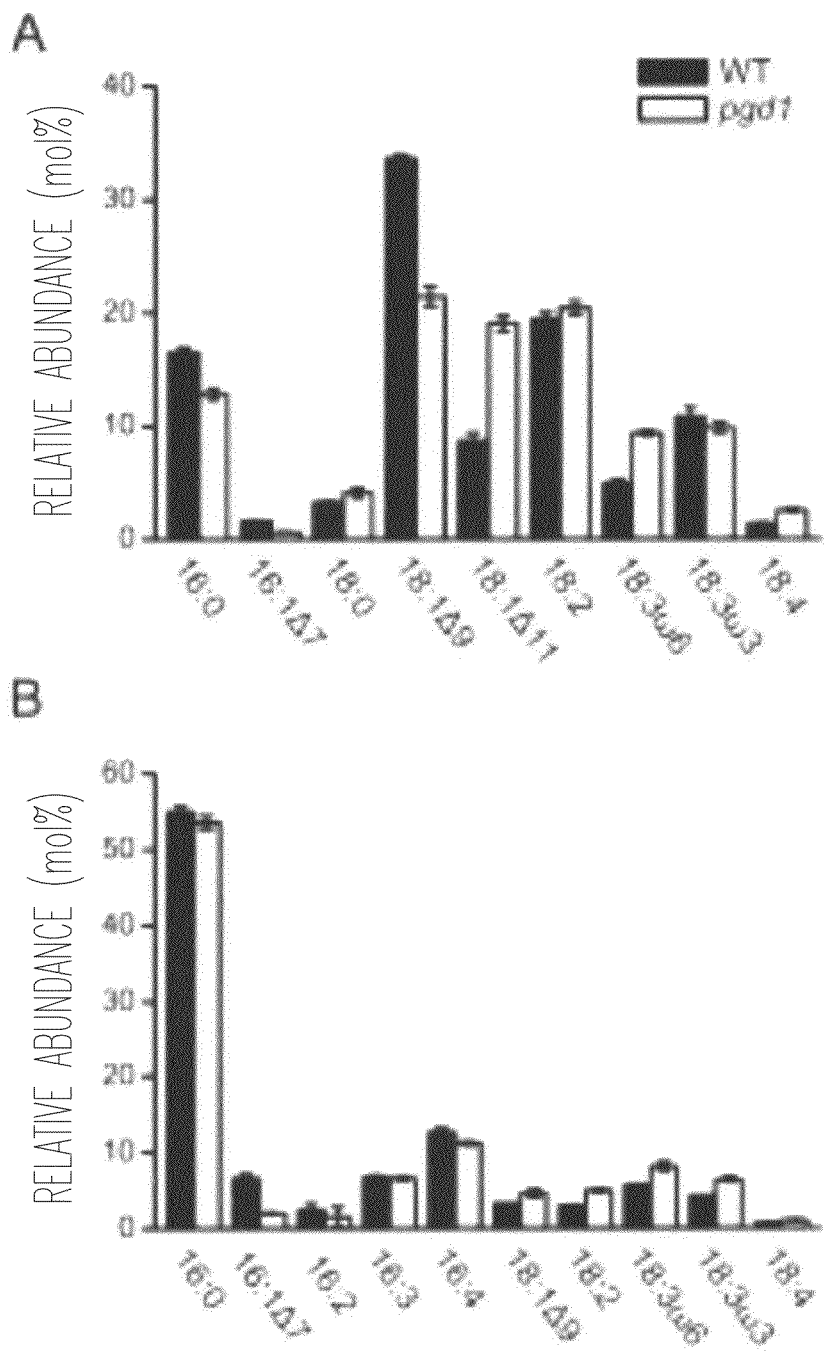
FIG. 5. Positional analysis of TAG acyl groups of the wild-type parental strain (WT) and pgd1 mutant 48 h after transfer to N-depleted medium (—N). Purified TAG from *Chlamydomonas* cells were hydrolyzed by *Rhizopus* lipase. (A) Free fatty acids were presumed to be derived from sn-1/sn-3 position of the glyceryl back bone of TAG. (B) The residual monoacylglycerol contains the sn-2 position acyl groups. The values represent the average of three replicates with error bars indicating standard deviation.

To gain more information on the origin of the diacylglycerol moiety for TAG biosynthesis and possible role of oleate (18:1$^{\Delta 9}$) in limiting TAG biosynthesis in pgd1, positional analysis of TAG acyl groups was conducted with *Rhizopus arrhizus* lipase. *Rhizopus* lipase specifically hydrolyzes the sn-1 position of membrane glycerolipids or the sn-1/sn-3 positions of TAG and is frequently used for the positional analysis of acyl groups in glycerolipids (Fischer et al. 1973, Siebertz and Heinz 1977). Consistent with previous observations (Fan et al. 2011), the sn-2 position of TAG is mostly composed of C16 acyl groups while sn-1/sn-3 positions contain both C16 and C18 acyl groups (FIG. 5). While a decrease in oleate in the sn-1 or sn-3 position was obvious, the method did not allow us to distinguish between the two positions. For sn-1/sn-3, the relative contents of 18:4, 18:3$^{\omega 6}$ and 18:1$^{\Delta 11}$ were 2-fold higher in the pgd1 mutant than in the wild-type parental strain (FIG. 5A). This was also seen in the total composition of all TAG acyl groups (FIG. 4D). Interestingly, 18:4 and 18:3$^{\omega 6}$ are mostly found in the extraplastidic lipids DGTS (FIG. 11A) and PtdEtn (FIG. 11B). Vaccenic acid (18:1$^{\Delta 11}$) is produced through elongation of 16:149, at least in plants (Nguyen et al. 2010), and is presumed to be extraplastidic. In view of an approximate 50% reduction of TAG in the pgd1 mutant, the 2-fold relative increase in these three fatty acids suggests that the supply of TAG precursors from extraplastidic lipid turnover is not affected.

Precursor Fluxes from Plastid Lipids to TAG are Reduced in pgd1.

Figure 6:
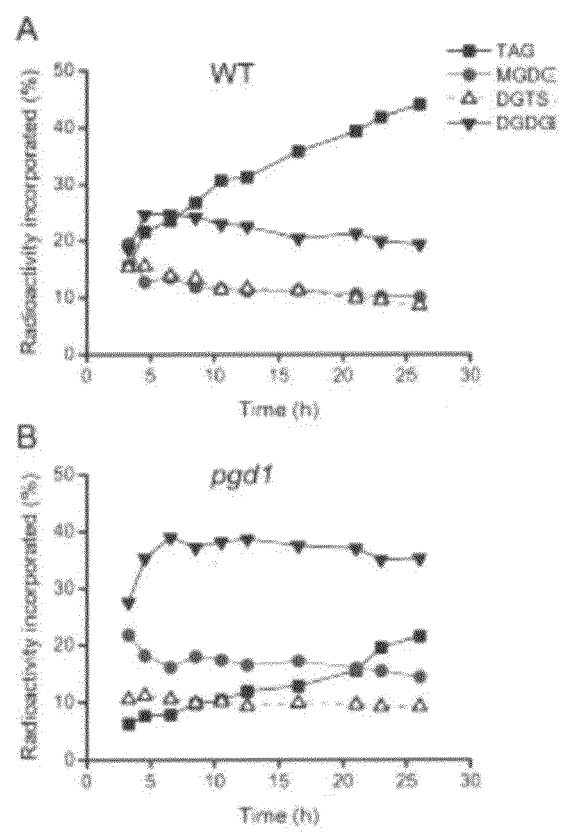
FIG. 6. In vivo pulse-chase acetate labeling of lipids in the wild-type parental strain (WT) and the pgd1 mutant. Labeled acetate was added 12 h following transfer of cells to TAP-N medium. The length of the [$^{14}$C]-acetate labeling pulse was 200 min, after which the cells were transferred to TAP-N medium lacking labeled acetate. Cells were collected at the times indicated and lipid extracts were prepared and analyzed. The fraction of label in all analyzed lipids is given; lipids containing the bulk of the label and those most relevant for the discussion are shown in this figure. Fractions of label in other lipids are shown in FIG. 13. Lipid abbreviations are as defined for FIG. 4. The data are from one representative experiment of a series of independent experiments.
Figure 12A:
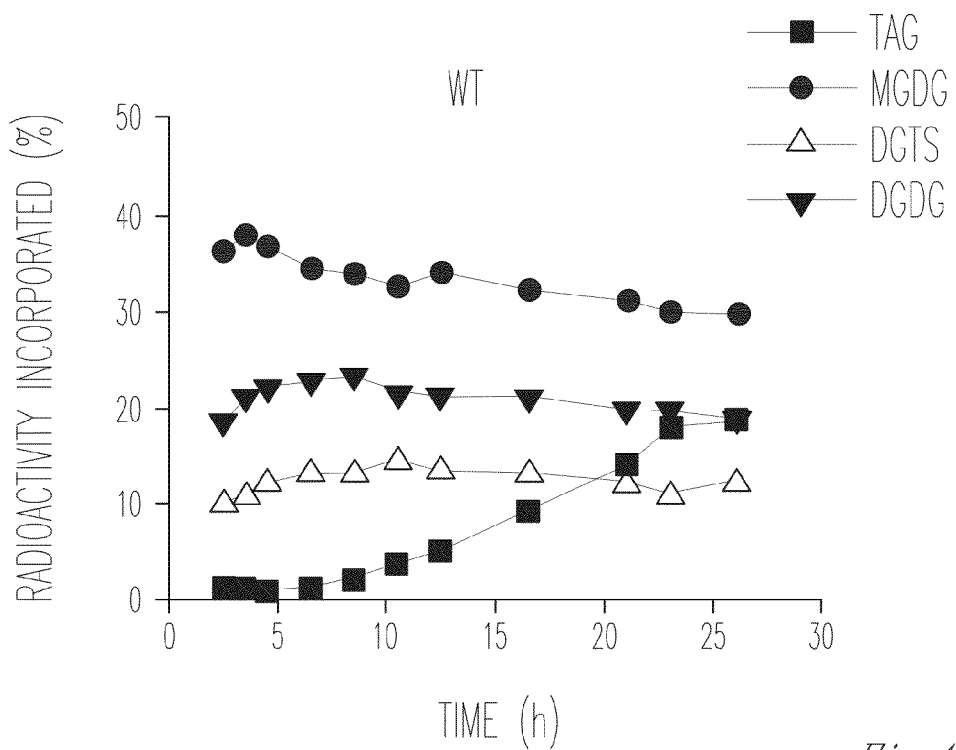
FIG. 12. In vivo pulse-chase acetate labeling of lipids in the wild-type parental strain (WT) and the pgd1 mutant before N deprivation. Labeled acetate was added prior to the transfer to TAP-N medium. The length of the [$^{14}$C]-acetate labeling pulse was 150 minutes after which the cells were transferred to TAP-N medium lacking labeled acetate. Cells were collected at the times indicated and lipid extracts were prepared and analyzed. The fraction of label in all analyzed lipids is given; only lipids containing the bulk of the label or those most relevant for the discussion are shown. Lipid abbreviations are as defined for FIG. 4. The given data are from one representative experiment of a series of independent experiments.
Figure 12B:
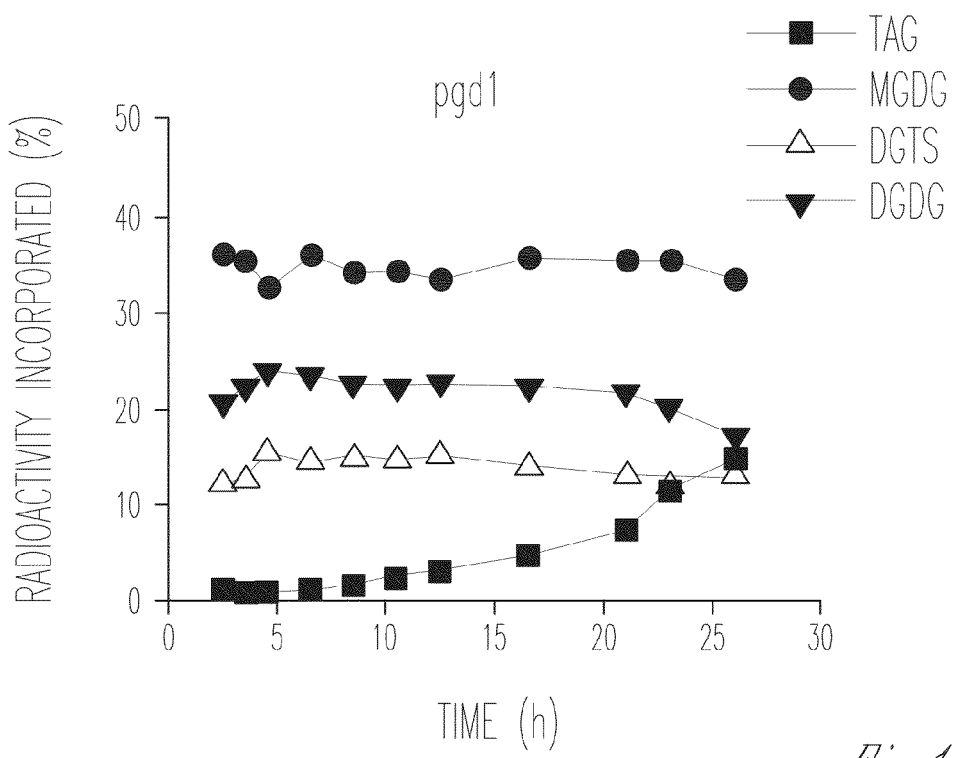
Figure 13A:
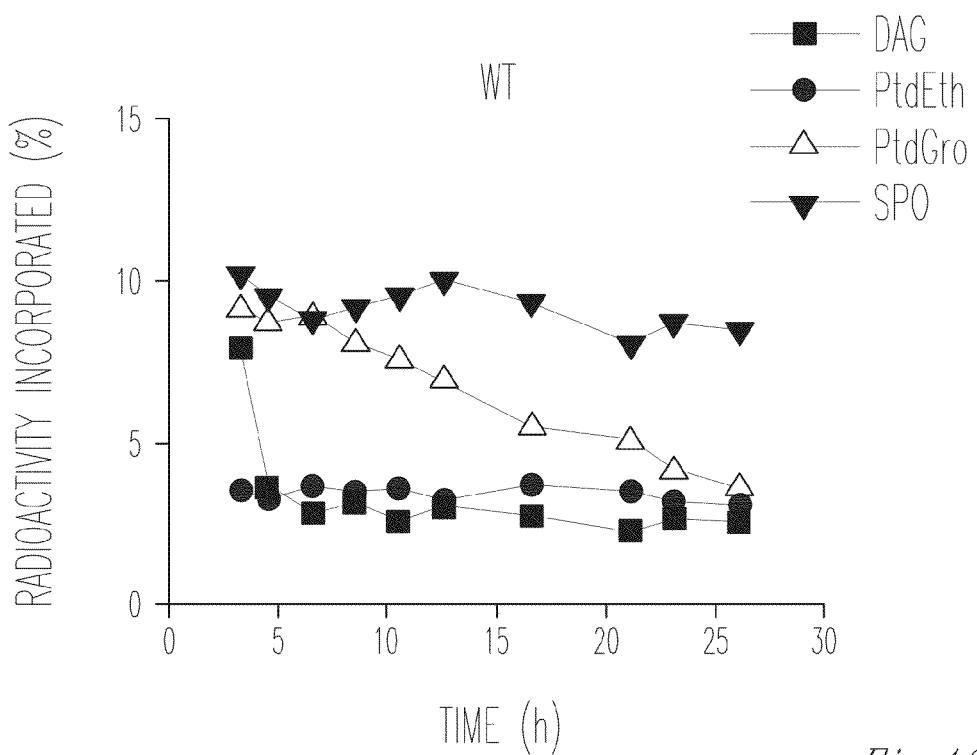
FIG. 13. In vivo pulse-chase acetate labeling of PtdEtn, PtdGro, SQDG and PtdIns in the wild-type parental strain (WT) and the pgd1 mutant. The data are from the same set of experiments as shown in FIG. 6. Lipid abbreviations are as described in FIG. 4. SQDG, PtdIns and TLC origin were scraped together as one fraction (SPO).
Figure 13B:
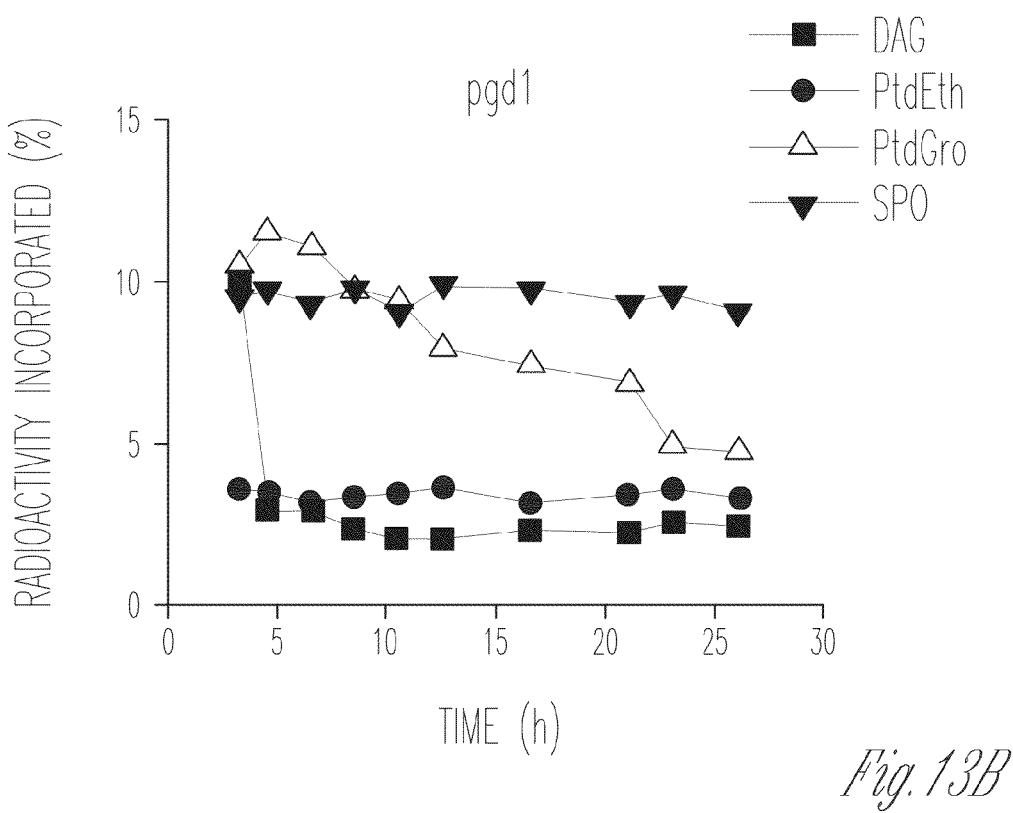

The analysis described above can only provide a static picture of lipid composition. However, the defect in a putative lipase-encoding gene in the pgd1 mutant suggested that lipid remodeling or turnover might play a role in TAG accumulation in *Chlamydomonas* following N deprivation. To observe possible changes in the dynamics of lipid metabolism in the pgd1 mutant, we employed pulse-chase labeling of membrane lipids using [$^{14}$C]-acetate which can be converted easily to precursors of fatty acid biosynthesis in plastids. The labeling pulse was provided either before (150 min pulse duration, FIG. 12) or during N deprivation (200 min pulse duration initiated 12 hours after the start of N deprivation, FIG. 6 and FIG. 13). Lipids were extracted as indicated and fractions of label incorporation into major lipids during the chase stage were calculated. The difference in the incorporation of label into TAG between the wild-type parental strain and pgd1 was more prominent when the labeling pulse was applied during N deprivation (FIG. 6) compared to its application prior to N deprivation (FIG. 12). This observation suggested that exchange of de novo synthesized acyl groups through the membrane lipid pool into TAGs during N deprivation might involve PGD1, rather than the conversion of preexisting membrane lipids formed under N-replete conditions to TAGs. When the pulse was applied following N deprivation, plastid lipids, especially galactoglycerolipids, were rapidly labeled (FIG. 6). Conditions were chosen such that the total label in the lipid extract during the chase phase remained approximately the same. In the wild-type parental strain, an increase of label in TAG was observed in parallel with a decrease of label in membrane lipids suggesting the incorporation of acyl or diacylglyceryl groups derived from membrane lipids into TAGs. After 25 hours of chase the label remaining in membrane lipids was lower than that in TAGs. This situation was reversed in the pgd1 mutant. In particular the fraction of label in the two galactoglycerolipids DGDG and MGDG remained much higher in pgd1. Because MGDG is its precursor, DGDG was labeled with some delay. In fact, it was the most highly labeled lipid in the pgd1 mutant extracts presumably because the transfer of labeled acyl or diacylglyceryl groups from MGDG into TAGs was disrupted in the mutant. When the pulse was applied prior to N deprivation (FIG. 12), MGDG was the most highly labeled lipid reflecting the fact that it is also the most abundant lipid under N-replete conditions, when TAG biosynthesis is repressed. Apparently, following N deprivation, de novo synthesized acyl groups in the plastid are incorporated first into plastid membrane lipids, in particular MGDG, prior to becoming incorporated into TAGs, and the incorporation of acyl groups into TAG seems to require PGD1. Thus MGDG serves as precursor for a fraction of acyl or diacylglycerol groups, those containing oleic acid (see FIG. 4), incorporated into TAGs following N deprivation. This process is disrupted in the mutant and more MGDG is converted to DGDG instead of TAG. While PtdGro was rapidly turned over, the rates of turnover remained approximately the same in the pgd1 mutant and the wild type (FIG. 13). Based on these data we concluded that PGD1 might be a galactoglycerolipid lipase prompting us to tentatively name the gene Plastid Galactoglycerolipid Degradation 1 (PGD1).

PGD1 Hydrolyzes Acyl Groups of MGDG with a Preference for the Sn-1 Position.

Figure 7:
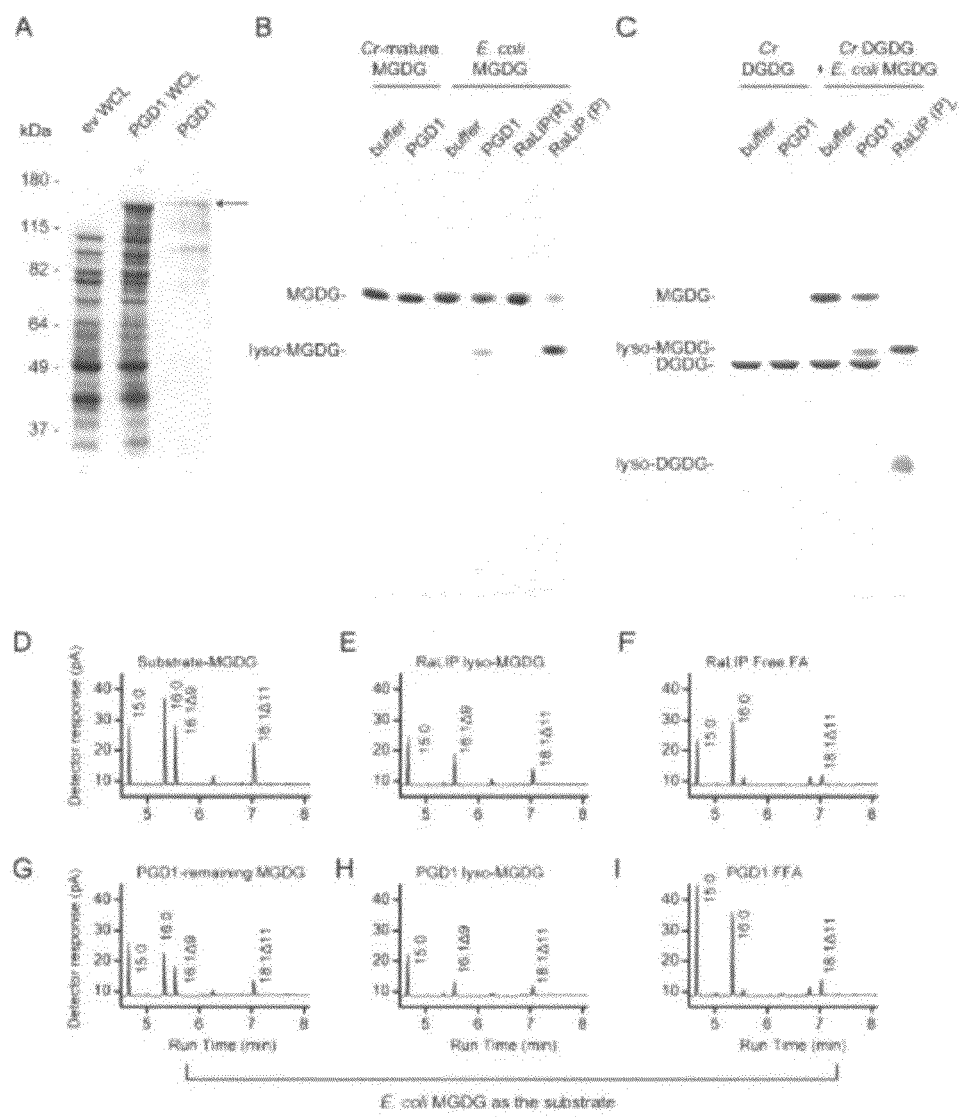
FIG. 7. Activity of the recombinant PGD1 protein on MGDG and DGDG. (A) SDS-PAGE of purified PGD1 protein and whole cell lysates (WCL) from *E. coli* cells expressing the PGD1 open reading frame and the empty vector control. Protein loading was 6 μg per lane for whole cell lysates. Purified PGD1 protein loaded was 1 μg (Quantified as in Methods; possibly biased by components in refolding buffer). Proteins were stained by Coomassie Brilliant Blue. The arrow indicates the PGD1 protein. (B) A thin-layer chromatogram of polar lipids from the lipase assay mixtures to which either mature MGDG extracted from *Chlamydomonas* (Cr), or MGDG extracted from the *E. coli* strain over-expressing cucumber MGDG synthase were added as substrates. (C) A thin-layer chromatogram of polar lipids from the lipase assay mixtures to which either DGDG extracted from *Chlamydomonas* alone or mixed in with *E. coli* derived MGDG at a 1:1 molar ratio were added as substrates. Glycolipids were visualized with α-naphtol reagent. Reaction products obtained with refolded PGD 1 protein, blank refolding buffer and *Rhizopus arrhizus* lipase dissolved in protein refolding buffer (RaLip-R) or PBS (RaLip-P) were analyzed. (D)-(I) Gas liquid chromatograms of methyl esters derived from a buffer control reaction containing *E. coli*-derived MGDG (D) or different fractions after lipase reaction with *E. coli*-derived MGDG as discussed in the text. As an internal standard, 15:0 was used.
Figure 14A:
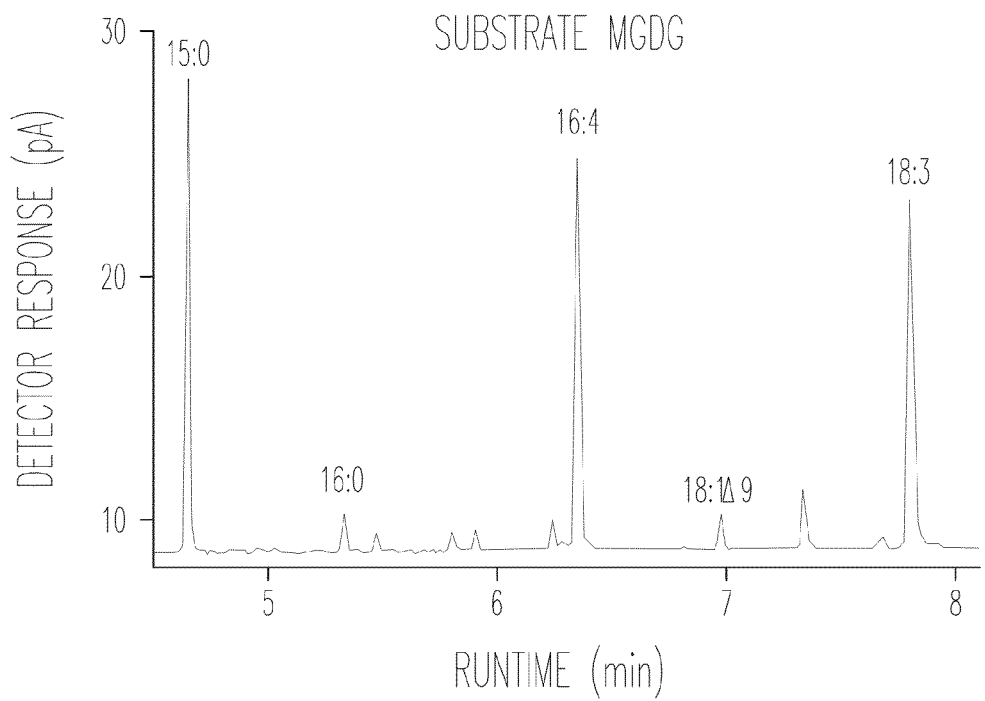
FIG. 14 Hydrolysis of *Chlamydomonas*-derived MGDG by PGD1. Gas liquid chromatograms of methyl esters derived from different fractions after lipase reaction are shown as discussed in detail in the text. As internal standard 15:0 was used. (A) Substrate *Chlamydomonas* MGDG; (B) remaining MGDG after PGD1 hydrolysis; (C) and (D) lyso-MGDG and free fatty acids generated from PGD1 hydrolysis, respectively. \
Figure 14B:
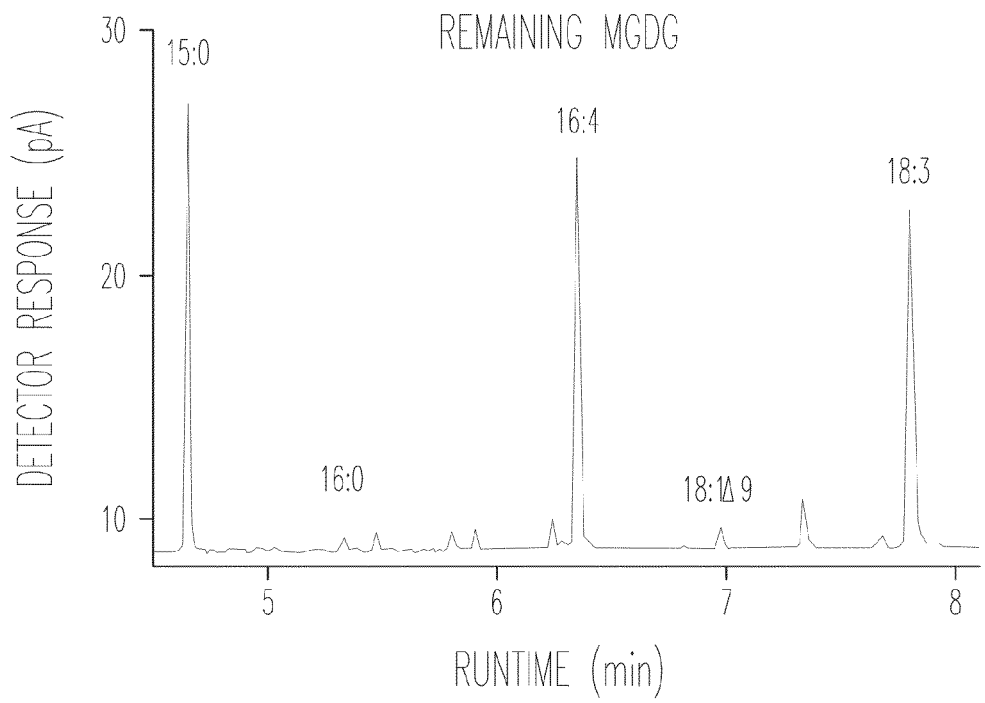
Figure 14C:
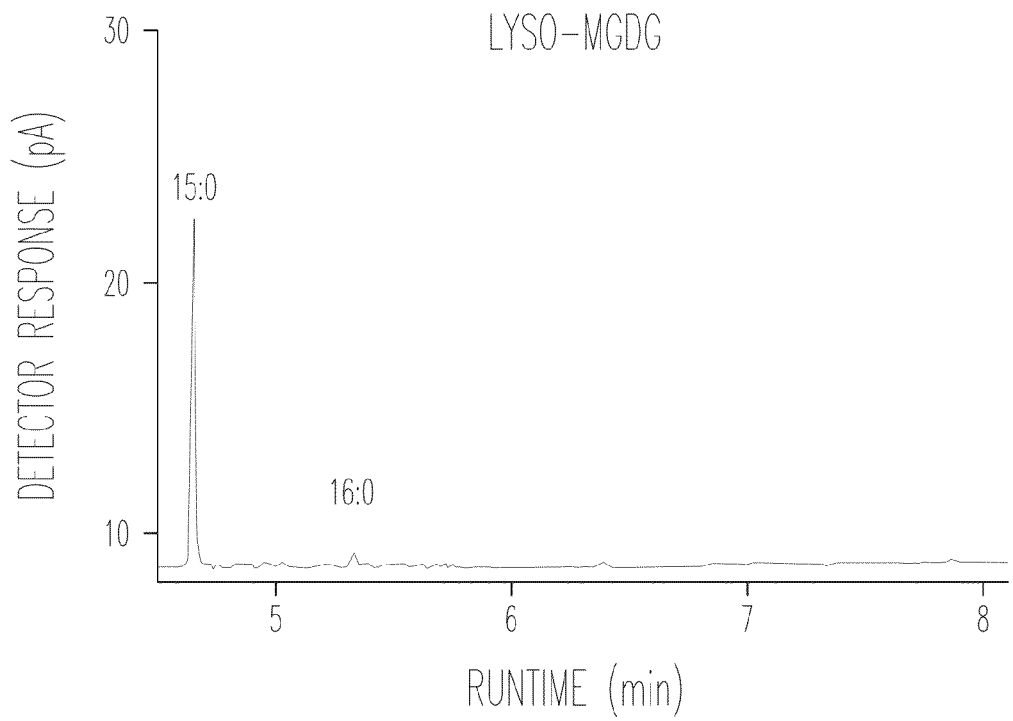
Figure 14D:
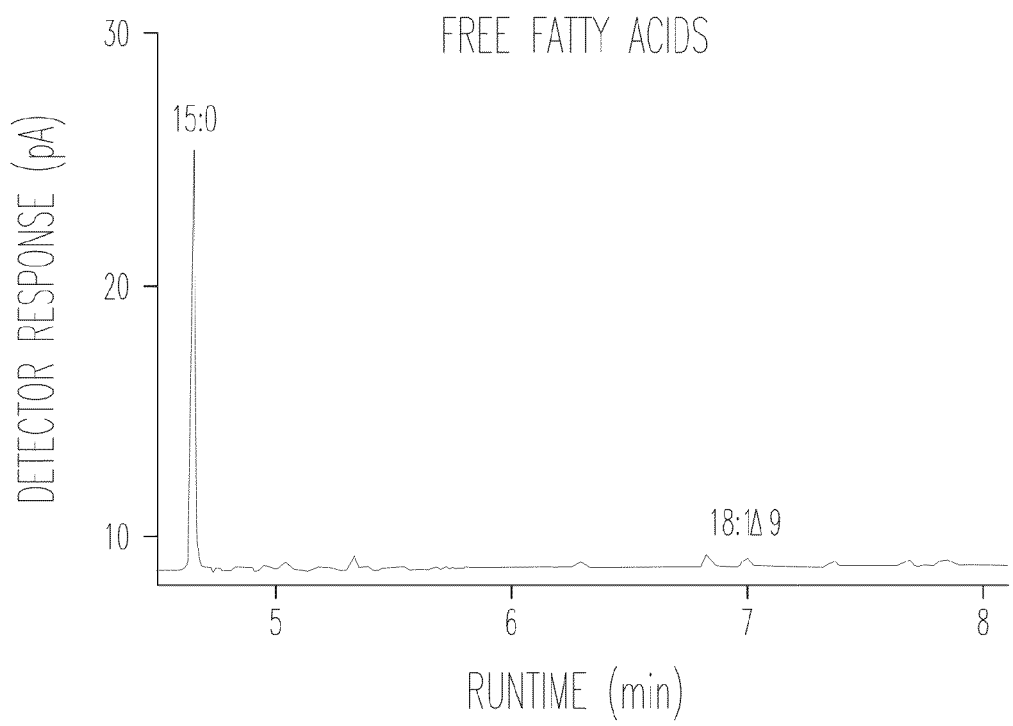

To more directly determine the biochemical activity of PGD1, we produced the recombinant protein in *E. coli*. The recombinant protein was affinity-purified from denatured inclusion bodies (FIG. 7A), renatured, and offered various substrate lipids in a lipase activity assay. To control for spontaneous lipid hydrolysis or lyso-lipid contamination we assayed the protein refolding buffer without proteins. As a positive control we assayed *Rhizopus* lipase. We employed MGDGs of different molecular composition as substrates to determine the enzyme's preference. "Mature" MGDG was isolated from *Chlamydomonas* cells, which predominantly contains molecular species 18:3/16:4 (sn-1 I sn-2). Using this substrate, the lyso-MGDG product that was generated was rather faint (FIG. 7B). By analyzing the different fractions, we found that in the remaining MGDG after PGD1 hydrolysis, the 16:0 and 18:1$^{\Delta 9}$ acyl groups selectively disappeared while the major acyl groups 16:4 and 18:3 remained (FIGS. 14A and 14B). This suggested that PGD1 prefers to hydrolyze de novo synthesized MGDG (18:1$^{\Delta 9}$/16:0) and the reaction stops when 18:1$^{\Delta 9}$/16:0 is depleted in the assay mixture. Hypothesizing that PGD1 only hydrolyzes de novo-formed MGDG to release 18:1$^{\Delta 9}$ for further TAG biosynthesis, reduction of 18:1$^{\Delta 9}$ in TAG of the pgd1 mutant can be explained. The lyso-MGDG obtained using MGDG purified from *Chlamydomonas* exclusively contained 16:0 (FIG. 14C), suggesting that PGD1 prefers the sn-1 position. However, the low amount of free fatty acids generated (FIG. 14D) made it difficult to draw a firm conclusion, considering that there may be lipids or fatty acids co-purified with the PGD1 protein.

To confirm that PGD1 prefers less desaturated molecular species, MGDG synthesized in *E. coli* by the activity of recombinant cucumber MGDG synthase (Shimojima et al. 1997) was used. In the buffer control lane, presumably no hydrolysis occurred as no generation of lyso-MGDG was seen (FIG. 7B). This *E. coli*-derived MGDG band representing the substrate was isolated and shown to contain a combination of 18:1$^{\Delta 11}$, 16:0 or 16:1$^{\Delta 9}$ acyl groups (FIG. 7D), which is similar to the newly assembled MGDG in *Chlamydomonas*. As indicated in FIG. 7B by the intensity of the lyso-MGDG band, PGD1 was more active on the MGDG species produced in *E. coli* using the cucumber MGDG synthase than the mature, mostly unsaturated MGDG from *Chlamydomonas*.

To obtain more information on the substrate preference of PGD1, we compared the acyl composition of the MGDG substrate, lyso-MGDG and free fatty acid products that remained after incubation with the corresponding fractions obtained from *Rhizopus* lipase hydrolysis. *Rhizopus* lipase was inhibited by the buffer used for PGD1 refolding (FIG. 7B). To generate lyso-lipid (including lyso-MGDG) standard, PBS instead of protein refolding buffer was used to dissolve *Rhizopus* lipase for all the reactions mentioned below. The *E. coli*-derived MGDG contains 16:0, 16:1$^{\Delta 9}$ and 18:1$^{\Delta 11}$ (FIG. 7D, untreated sample) with 16:0 and 18:1$^{\Delta 11}$ present in the sn-1 (FIG. 7F), and 16:1$^{\Delta 9}$ and 18:1$^{\Delta 11}$ in the sn-2 position (FIG. 7E), as determined by *Rhizopus* lipase digestion. After PGD1 hydrolysis, some of the substrate MGDG remained (FIG. 7B). However, all the three major fatty acids were decreased to a similar extent (FIG. 7G). Thus, the remaining MGDG was due to limited enzyme activity instead of the preference between different molecular species within *E. coli*-derived MGDG. Lyso-MGDG (FIG. 7H) and free fatty acids (FIG. 7I) generated by PGD 1 resembled the corresponding fractions following *Rhizopus* lipase digestion in fatty acid compositions, indicating that PGD1 prefers acyl groups at the sn-1 position similar to *Rhizopus* lipase.

Figure 15A:
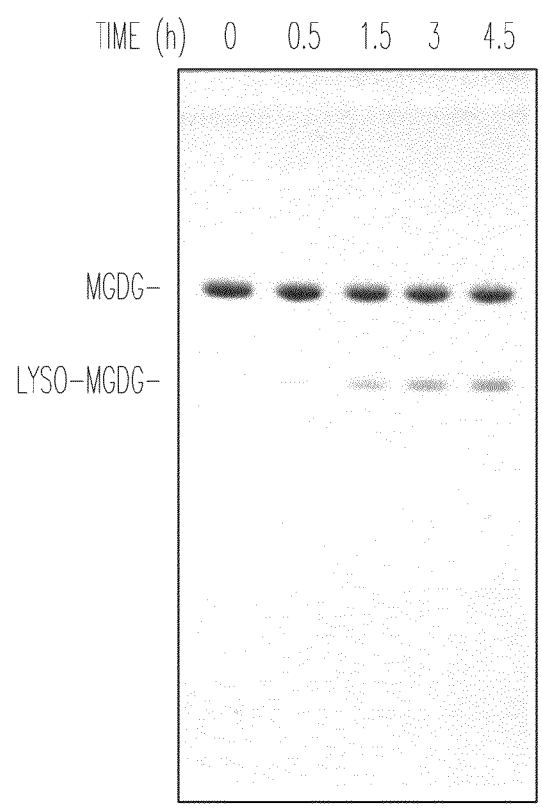
FIG. 15. Quantitative hydrolysis of *E. coli* derived MGDG by PGD1. (A) A thin-layer chromatogram of polar lipids from the PGD1 assay mixtures to which MGDG extracted from the *E. coli* strain over-expressing cucumber MGDG synthase was added as substrate. Glycolipids were visualized with α-naphtol reagent. One aliquot of the same volume was extracted and loaded to the TLC for each time point. (B) Dependence of MGDG hydrolysis on MGDG concentration. Reaction velocity was quantified as the amount of lyso-MGDG generated per min per mg purified PGD1 protein. A representative result is shown for each panel.
Figure 15B:
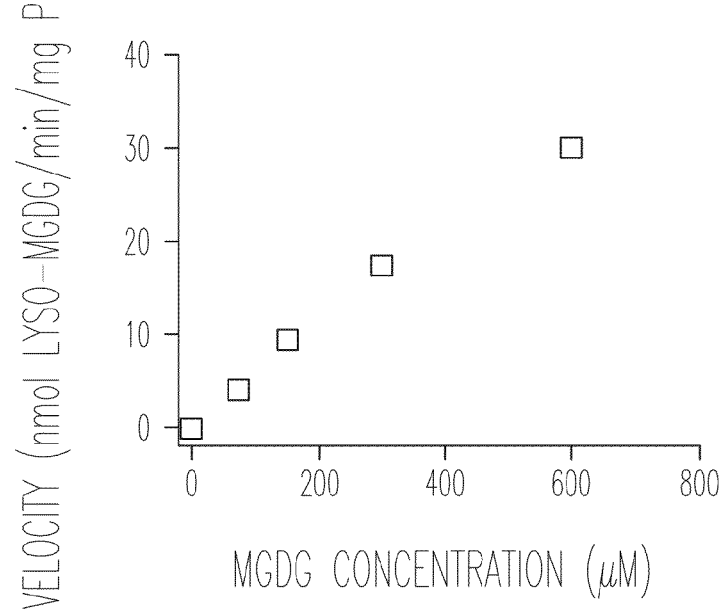

We also explored the kinetics of PGD1 mediated hydrolysis of *E. coli*-derived MGDG. Lyso-MGDG was detectable in 30 minutes and continuously increased within 4.5 hours of incubation (FIG. 15A). At 4.5 hours, the bulk of MGDG substrate still remained and we chose a 3 hours incubation time to test the relationship between reaction velocity and substrate MGDG availability. It should be noted that MGDG is not soluble and, therefore, classical enzyme kinetics is not directly applicable in this case. It should also be cautioned that the purified PGD1 enzyme went through a denaturation process, and the lipase activity may not be completely regained during refolding for all molecules present. Lyso-MGDG instead of free fatty acids was quantified because free fatty acids can be derived either from MGDG or lyso-MGDG. The hydrolysis of MGDG was linear in reaction velocity up to an apparent MGDG concentration of 300 µM (FIG. 15B).

PGD1 does not Act on DGDG.

During the labeling experiment shown in FIG. 6, labeling of DGDG increased to a greater extent in the pdg1 mutant than did MGDG, suggesting that DGDG might be a possible substrate of PGD 1. To test this possibility, DGDG extracted from *Chlamydomonas* was used as a substrate in the PGD1 assay. However, no formation of lyso-DGDG was detected by sugar-specific staining (FIG. 7C). When *E. coli*-derived MGDG and *Chlamydomonas* derived-DGDG were offered in equal amounts, only lyso-MGDG was formed, showing that PGD1 used MGDG but not DGDG in this competition experiment, which might reflect the in vivo situation in which both lipids are present in the same membrane. While a single MGDG molecular species 18:3/16:4 predominates in *Chlamydomonas* (FIG. 11C), DGDG is represented by a greater variety of molecular species with mostly 16:0 at the sn-2 position, and considerable amounts of 18:1$^{\Delta 9}$, 18:2 and 18:3 acyl groups present at the sn-1 position of the glycerol moiety (Giroud et al. 1988) (FIG. 11D). Apparently, none of these DGDG molecular species is hydrolyzed by PGD1 under the conditions used. In addition, we tested PGD1 activity on other major membrane lipids prepared from *Chlamydomonas* extracts. PGD1-dependent generation of lyso-DGTS and lyso-PtdEtn were detectable by iodine staining, but at much lower levels than those generated by *Rhizopus* lipase (FIGS. 16A and 16B). Lyso-SQDG hydrolysis was not detectable by sugar-specific staining (FIG. 16D). Repeated trials of PtdGro hydrolysis by *Rhizopus* lipase failed to yield an obvious lyso-PtdGro band (FIG. 16C), which is expected to run slower than PtdGro on TLC plates. This might be due to the fact that the sn-2 position of PtdGro is composed of 16:0 and 16:1$^{\Delta 3}$ only (Giroud et al. 1988) while iodine stains lipids by binding to double bonds. Nevertheless, a major decrease in the lipid substrate after PGD1 hydrolysis was visible for *E. coli* MGDG (FIG. 7B) but not PtdGro nor DGTS, PtdEtn and SQDG. At this time, synthetic molecular species are not available for lipids such as MGDG and DGTS. Thus, it was not possible to compare lipids with exactly the same acyl compositions but different head groups.

The Pgd1 Mutant Loses Viability Following N Deprivation.

Figure 8:
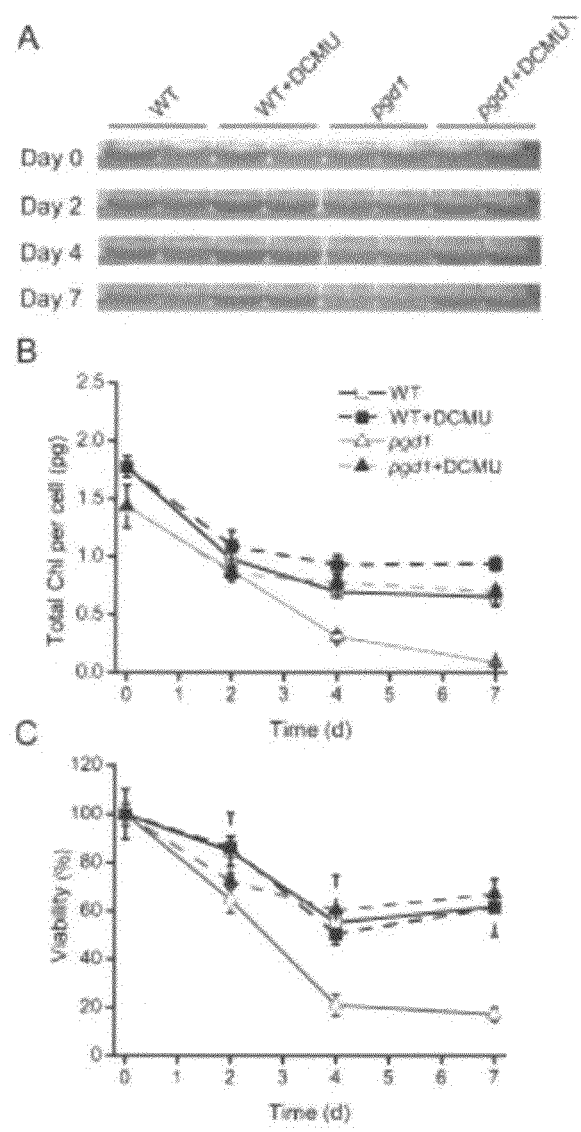
FIG. 8. Biochemical and physiological characterization of wild-type parental strain (WT) and the pgd1 mutant following N deprivation. (A) Appearance of cultures grown in TAP-N for the number of days indicated. The electron transport chain inhibitor DCMU dissolved in dimethyl sulfoxide was present at a final concentration of 2 μM as indicated. Two representative cultures per line are shown. (B) Time course of total cellular chlorophyll (Chl) content. (C) Time course of cell viability relative to day 0, the start of N deprivation following transfer to TAP-N medium. (D) Time course of cellular thiobarbituric acid reactive substances (TBARS) content. (E) TAG accumulation presented as ratio of fatty acids (FA) in TAGs over total fatty acids in the lipid extracts after 2 d of N deprivation. For all quantitative data, three replicates were averaged with SD indicated by the error bars.
Figure 8:
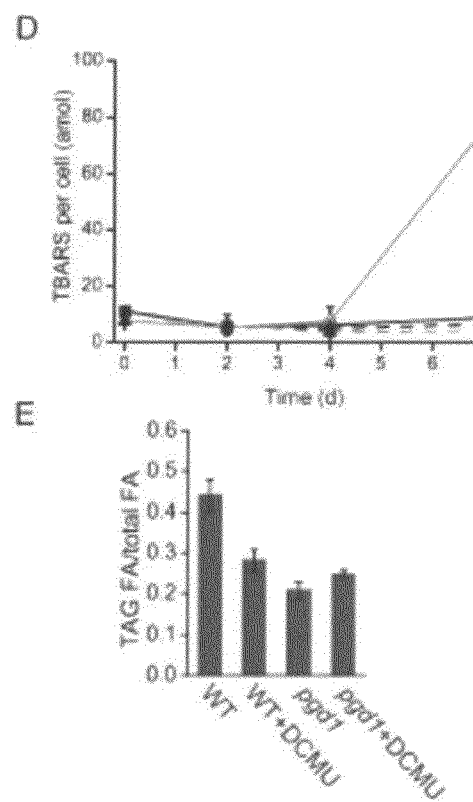

In contrast to the wild-type parental strain, pgd1 mutant liquid cultures and colonies on agar solidified medium became chlorotic 5-9 days following N deprivation (FIGS. 1C and 8A). We took advantage of this observation during the complementation analysis described above. The increasing chlorosis correlated well with the decrease in the chlorophyll content (FIG. 8B), as well as the decline in the viability of pgd1 following N deprivation (FIG. 8C). Following N deprivation *Chlamydomonas* typically ceases cell growth after approximately one cell cycle (James et al. 2011, Work et al. 2010). However, these cells continue to capture light with their photosynthetic light harvesting complexes. If electron acceptors become limiting due to the cessation of growth under these conditions, photosynthetic electron transport chain components may become over-reduced. Indeed, it has been hypothesized that enhanced fatty acid synthesis and sequestration of acyl groups in TAG provide an electron sink, because acyl groups are among the most reduced carbon compounds that algae can produce (Hu et al. 2008). A potential consequence of TAG deficiency is the increase in the NADPH/NADP$^+$ ratio. This is because NADPH is a major reductant in fatty acid synthesis. With decreasing availability of NADP$^+$, molecular oxygen may become an alternative electron acceptor for photosystem I. Thus when photosynthetic electron transport exceeds the capacity of the NADP$^+$ pool to accept electrons, in pgd1 due to decreased TAG synthesis, superoxide may be generated and further converted to $H_2O_2$ and hydroxyl radicals (Mehler 1951). Overproduction of these highly cytotoxic reactive oxygen species (ROS) may lead to cell death. To begin to test this hypothesis, we took advantage of the herbicide 3-(3,4-dichlorophenyl)-1,1-dimethylurea (DCMU), which specifically inhibits photosynthetic electron transfer at the acceptor side of PS II (Trebst et al. 1970). DCMU treatment is well known to decrease the generation of superoxide and other reactive oxygen species from PSI (Davies et al. 1996, Robert et al. 2009, Wen et al. 2008). When DCMU was added to N-deprived cultures, chlorosis and viability loss were suppressed (FIGS. 8A, B, and C). To further verify this hypothesis, we analyzed thiobarbituric acid reactive substances (TBARS), a product of reactive oxygen species (Baroli et al. 2003), and observed a burst of TBARS in the pgd1 mutant, which was also reverted by DCMU (FIG. 8D). As expected, DCMU did not rescue the pgd1 TAG phenotype, but did decrease TAG levels of the wild-type parental strain (FIG. 8E) because of the decrease in electrons provided for NADPH generation.

Discussion

Figure 9:
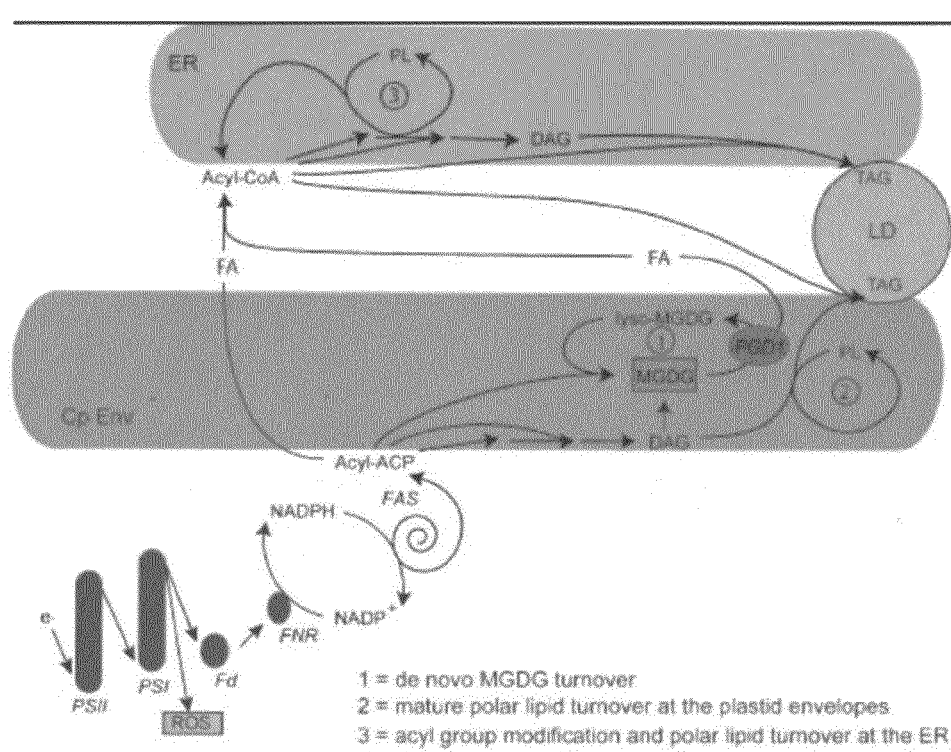
FIG. 9. Hypothesis placing PGD1 into the context of overall cellular lipid metabolism explaining its role in TAG biosynthesis. For simplicity a single lipid droplet (LD) is shown forming at the endoplasmic reticulum (ER) or the chloroplast envelope (Cp Env). Thylakoid membranes harboring the two photosystems have been omitted. Three lipid turnover processes discussed in the text are indicated by numbers: 1. Turnover of newly synthesized MGDG; 2. turnover of mature MGDG and other thylakoid lipids at the plastid envelopes; 3 acyl group modification and lipid turnover at the ER. Enzymes, protein complexes and processes are italicized: FAS, fatty acid synthase complex; Fd, ferredoxin; FNR, ferredoxin: NADP+ reductase; PSI and II, Photosystem I and II. Substrates and products: DAG, diacylglycerol; e-, electron; FA, fatty acid; MGDG, monogalactosyldiacylglycerol; PL, polar lipids; TAG, triacylglycerol; ROS, reactive oxygen species. Not all intermediates or reactions involved are shown.

The primary phenotype through which the pgd1 mutant was identified, is a reduction in the accumulation of TAGs following N deprivation (FIG. 1). Because the affected gene, PGD1, encodes a galactoglycerolipid lipase with preference for the sn-1 position of the respective glyceryl backbone (FIG. 7), we had to reconsider how TAGs are synthesized in *Chlamydomonas*. A mechanistic model that accommodates our current findings on the pgd1 mutant and the PGD 1 protein, and that places PGD1 into the context of overall cellular lipid metabolism is shown in FIG. 9. Because the pgd1 mutant still accumulates considerable amounts of TAGs, additional pathways not involving PGD1 are contributing to TAG accumulation in N-deprived cells. For the purpose of simplification, FIG. 9 shows a single lipid droplet receiving TAG assembled at the ER or the plastid envelopes. The process can be divided into two conceptual phases that will be discussed separately: First, the photosynthetic generation of reductant for fatty acid biosynthesis and second, the incorporation of acyl groups into TAGs, which we will discuss first.

An MGDG Deacylation/Acylation Cycle Involved in TAG Biosynthesis of *Chlamydomonas*.

FIG. 9 summarizes our current working hypothesis of PGD1 function in TAG metabolism. We have placed the galactoglycerolipids, in particular MGDG, at the center of the plastid envelope pathway as our pulse-chase experiment (FIG. 6) suggested that acyl groups or entire DAG moieties move through the membrane lipid fraction of the chloroplast prior to incorporation into TAGs. While the labeling of galactoglycerolipids in the pgd1 mutant was increased, the relative amounts of the membrane lipid classes did not change in the mutant. Apparently, the pool size of MGDG and other membrane lipids is strictly controlled to maintain functional photosynthetic membranes.

The importance of galactoglycerolipids in TAG metabolism in *Chlamydomonas* may arise from the fact that this alga lacks PtdCho (Giroud et al. 1988). PtdCho is one of the most rapidly labeled and metabolized membrane lipids in seed plants and acyl exchange involving PtdCho has been suggested to play a role in the export of fatty acids relevant for extraplastidic membrane lipid biosynthesis including that of TAGs (Bates et al. 2007, Bates et al. 2009). *Chlamydomonas* membranes contain the betaine lipid DGTS which has been widely assumed to play at least some of the roles of PtdCho in *Chlamydomonas* due to similarities in structure and biophysical properties of the two lipids (Sato and Murata 1991). However, our labeling and lipid analysis data showed no differences for DGTS between the parental strain and the pgd1 mutant and suggested it is not involved, at least in the aspect of TAG biosynthesis that is affected in the pgd1 mutant. Although DGTS and PtdEtn molecular species isolated from *Chlamydomonas* were hydrolyzed by recombinant PGD 1 to a limited extent (FIGS. 16A and 16B), DGTS and PtdEtn showed the same change in molecular species composition in the mutant, i.e., the reduction of oleic acid containing species (FIG. 4 and FIG. 11), as was seen also for TAGs. It should be noted that DGTS and PtdEtn are extraplastidic membrane lipids. Oleate ($18:1^{\Delta 9}$) and palmitate ($16:0$) typically are the de novo synthesized acyl groups incorporated into the glyceryl backbone. Thus the reduction of oleate in TAG in pgd1 suggests that the TAG affected in this mutant is derived from glyceryl moieties containing these de novo synthesized acyl groups. Pulse-chase labeling data obtained when labeled acetate was added prior to N deprivation showed few differences between the mutant and the parental strain (FIG. 12). However, stark differences were observed, when the pulse was given following N deprivation (FIG. 6) suggesting that the fraction of TAG requiring PGD1 activity indeed involves de novo fatty acid biosynthesis.

As DGTS and PtdEtn in the pgd1 mutant are likely downstream products of PGD1 activity, just like TAG as discussed above, it seems probable that a plastid lipid serves as the true substrate for PGD1 and that PGD1 may be involved in cycling newly synthesized fatty acids through the plastid polar lipid pool. DGDG is not likely a major substrate for PGD1 in cells as it is also not a substrate for PGD1 in vitro, even though it is highly labeled during pulse-chase experiments in the pgd1 mutant (FIG. 6). The delay in labeling of DGDG as compared to MGDG is consistent with biosynthesis of DGDG by galactosylation of MGDG. Thus if cycling of acyl groups into TAG through the MGDG pool is reduced in pgd1, the reduced flux from MGDG to TAG allows for greater availability of MGDG for DGDG biosynthesis explaining increased labeling of this lipid in the mutant.

In vitro lipase assays suggested that PGD1 prefers MGDG over DGDG, with a preference for MGDG molecular species with fewer double bonds over 18:3/16:4 species, and a preference for acyl groups at the sn-1 position over sn-2. To explain these observations, we propose an acyl-editing cycle (FIG. 9, process 1) involving MGDG assembled from de novo synthesized fatty acids ($18:1^{\Delta 9}/16:0$). One function of such a cycle involving a transient MGDG pool might be the transfer of fatty acids synthesized in the plastid through the plastid envelope membranes effectively accomplishing a net export of $18:1^{\Delta 9}$ acyl groups. As $18:1^{\Delta 9}$ is a major fatty acid in TAG (FIG. 4D), but not in DGTS or PtdEtn (FIGS. 11A and 11B), TAG is most affected of the extraplastidic lipids in the pgd1 mutant. Interestingly, in the pgd1 mutant MGDG did not accumulate $18:1^{\Delta 9}$ (FIG. 11C), but apparently continued to become desaturated to its mature 18:3/16:4 molecular species. Alternatively, it seems likely that MGDG assembly from newly synthesized acyl groups is feedback inhibited, adjusting the flow through the pathway to the demands of the cell. Thus, the total amount of fatty acids in the pgd1 mutant is lower than in the wild-type parental strain (FIG. 4C) and the relative amount of $18:1^{\Delta 9}$ in the total lipid extracts is reduced (FIG. 4D).

Figure 11C:
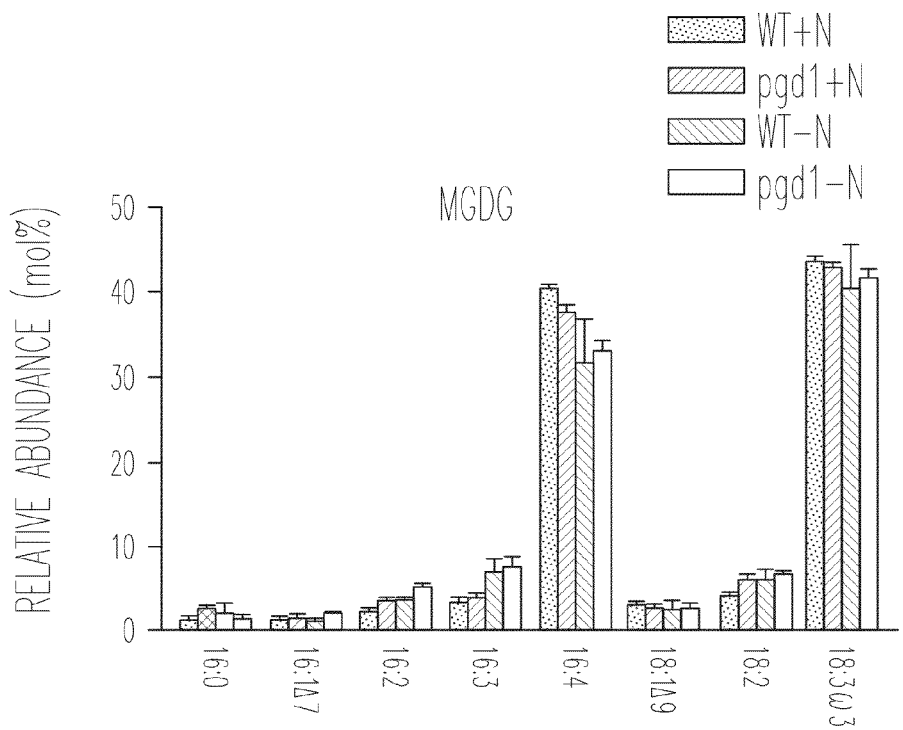
Figure 11D:
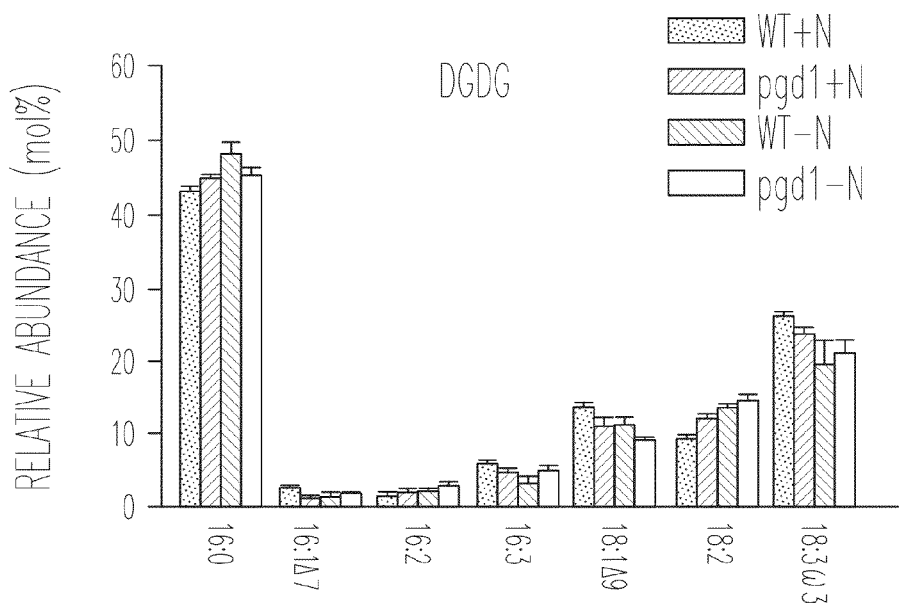
Figure 11E:
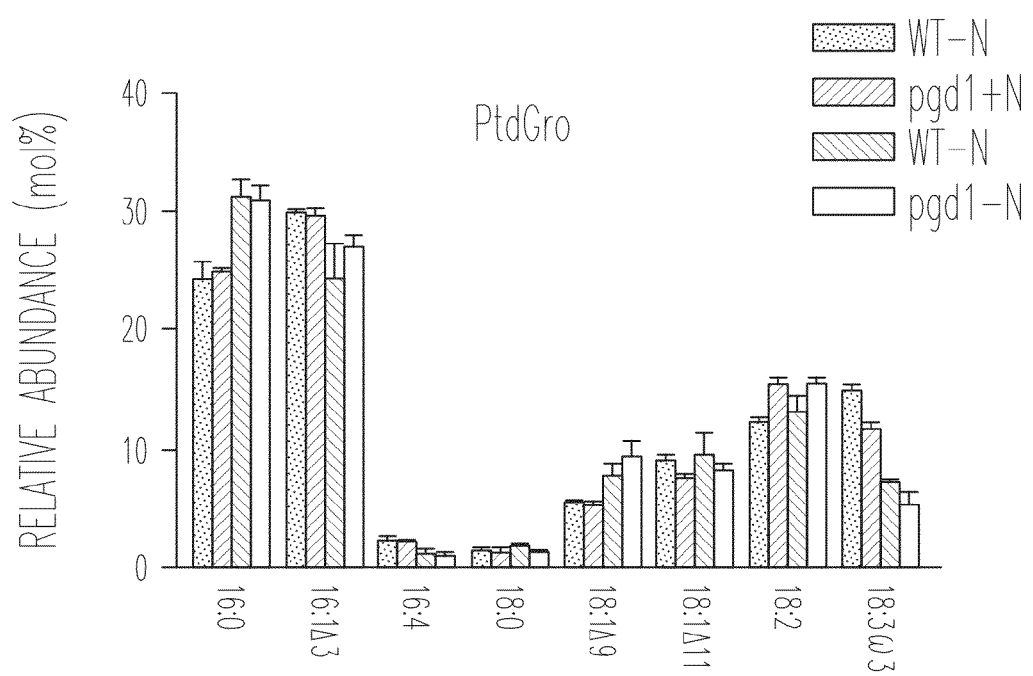

Mature MGDG found in thylakoid membranes is predominantly composed of the 18:3/16:4 species (FIG. 11C). Perhaps the presence of the unusual 16:4 acyl group, or other highly unsaturated acyl groups, protects MGDG from degradation by PGD1 because it is a necessary building block of the photosynthetic membrane, while allowing cycling of de novo synthesized acyl groups through the MGDG pool. This process is not perfect as 18:3 and 16:4 acyl groups were present in TAGs of the wild-type parental strain or the pgd1 mutant indicating some turnover of mature MGDG (FIG. 9, process 2). It is likely that following severe N deprivation, photosynthetic membranes containing mature MGDG species are degraded to some extent, perhaps involving lipases different from PGD1, and that these acyl or diacylglycerol moieties find their way into the TAG fraction. But the bulk of the membrane has to be maintained for a rapid recovery when nitrogen is re-supplied. Thus, the resistance of mature *Chlamydomonas* MGDG to PGD1-catalyzed hydrolysis supports the hypothesis of de novo synthesized acyl group cycling through a specific MGDG subpool. For this hypothesis to be valid, an acyl-ACP:lyso-MGDG acyltransferase activity is required for acylation of lyso-MGDG. Such an enzyme activity with a preference for the sn-1 position has been described for a cyanobacterium (Chen et al. 1988). We assume that *Chlamydomonas* has an ortholog, although the identity of the gene is not yet known.

One possible shortcoming of the proposed hypothesis is that no chloroplast transit peptide was predicted for PGD1 suggesting it to be extraplastidic. However, a cytosolic location would give PGD1 access to MGDG in the outer leaflet of the outer membrane, where this lipid has been shown to be present (Joyard et al. 1991). Analogously, the outer envelope protein, SFR2, of *Arabidopsis* (Moellering et al. 2010) acts on MGDG, suggesting that PGD1 has access to MGDG molecules in the outer envelope, even if it is not inside the plastid. We attempted to resolve this issue, but subcellular localization of PGD1 using GFP fusion constructs was unsuccessful. Alternative localization approaches such as immunolocalization of PGD1 will have to await the availability of antibodies.

How does Oleate Availability Affect TAG Biosynthesis?

The fatty acid composition of TAG of the pgd1 mutant (FIG. 4D and FIG. 5) lacks $18:1^{\Delta 9}$ and has a higher relative abundance of $18:1^{\Delta 11}$, $18:3^{\omega 6}$ and 18:4 acyl groups. To explain these observations, we considered the different sources for acyl groups that might be present in TAGs: 1. de novo synthesis (FIG. 9, process 1), for which $18:1^{\Delta 9}$ is the diagnostic fatty acid most increased following N deprivation (FIG. 4D); 2. Plastid membrane lipid degradation (FIG. 9, process 2) indicated by the presence of 16:4 and $18:3^{\omega 3}$ in TAGs derived from mature MGDG; and 3. extraplastidic membrane lipid modification and turnover (FIG. 9; process 3) characterized by the presence of $18:1^{\Delta 11}$, $18:3^{\omega 6}$ and 18:4 acyl groups in TAG. Fatty acids such as 16:0 can be derived from multiple processes and, therefore, are not diagnostic. The DAG backbone for most TAG species originates from the chloroplast pathway since the sn-2 position of TAGs of *Chlamydomonas* contains up to 80% 16-carbon fatty acids (FIG. 5) (Fan et al. 2011). We suggest that the plastid DAG pool primarily contributes to TAG biosynthesis. Plastid DAG can derive from both, de novo assembly and plastid membrane lipid degradation (FIG. 9, process 2). Turnover of de novo synthesized MGDG (FIG. 9, process 1) will contribute to the cytosolic acyl-CoA pool which provides acyl groups for the sn-3 position in TAGs. Similarly, lipid modification and turnover at the ER (FIG. 9, process 3) likely provide acyl-CoA substrate for the diacylglycerol acyltransferase (DGAT). The absence of PGD1 impairs the export of $18:1^{\Delta 9}$ with two consequences: 1. decrease of $18:1^{\Delta 9}$-CoA as substrate for TAG biosynthesis (FIG. 4D); and 2. decrease of $18:1^{\Delta 9}$ in the DAG backbones of DGTS and PtdEtn as shown in FIGS. 11A and 11B.

The relative amounts of fatty acids from extraplastidic membrane lipid turnover ($18:1^{\Delta 11}$, $18:3^{\omega 6}$ and 18:4) were doubled in TAG of the pgd1 mutant (FIG. 4D and FIG. 5). Considering the approximately 2-fold decrease in TAG content in the pgd1 mutant, this can be explained by the fact that extraplastidic membrane lipid turnover (FIG. 9, process 3) was not affected by the pgd1 mutation, while the total TAG amount was decreased 2-fold.

In contrast, the relative amounts of fatty acids provided by mature plastid membrane lipid turnover (16:4 and $18:3^{\omega 3}$) remained the same or only slightly increased (FIG. 4D and FIG. 5). Therefore, the absolute amounts of these two fatty acids in TAGs were decreased.

TAG Accumulation Protects Cells from Oxidative Damage.

While the accumulation of TAG by microalgae following nutrient deprivation has been repeatedly documented over many years, experimental exploration of the physiological role of this process has been scarce. The availability of the pgd/mutant with reduced oil content now provides an excellent opportunity to explore the function of TAG accumulation in microalgae. One can postulate that TAG is synthesized following N deprivation to store excess carbon when amino acid synthesis becomes impaired, an important but possibly not essential role for TAG accumulation, because photosynthate could presumably also be partitioned into increasing amounts of carbohydrates. However, the major loss in viability of pgd1 (FIG. 8C) suggests that TAG accumulation is essential for cells to survive following N deprivation. This observation provides direct experimental verification for recent suggestions that TAG might serve as an outlet to sequester excess electrons moving through the photosynthetic electron transport chain (Hu et al. 2008), thereby preventing the reduction of molecular oxygen and generation of ROS, which are cytotoxic. The connection between photosynthetic electron transport and TAG metabolism is shown in FIG. 9. In the wild-type parental strain, photosynthetic electron flow supplies the reducing equivalents in the form of NADPH for fatty acid synthesis. If electron transport is blocked with DCMU, the reduced electron flow into the NADPH pool would limit TAG biosynthesis resulting in lower levels of TAG (FIG. 8E) as was recently also observed by others (Fan et al. 2012). On the other hand if TAG biosynthesis is compromised as in pgd1, molecular oxygen probably serves as alternative electron acceptor leading to the formation of excess ROS and ultimately cell death. DCMU treatment of pgd1 relieves the production of ROS by decreasing the electron flow to molecular oxygen.

The assay employed to detect thiobarbituric acid reactive substances (TBARS) is commonly used to measure the consequences of oxidative stress in *Chlamydomonas* (Baroli et al. 2003, Fischer et al. 2007). As products of lipid peroxidation, TBARS are easier to detect than ROS themselves which are short-lived (Shulaev and Oliver 2006). We observed a strong accumulation of TBARS in the pgd1 mutant on day 7 of N deprivation (FIG. 8D). However, this effect was preceded by the loss of ability to form colonies indicating a loss in cell viability (FIG. 8C). Similarly, Baroli et al. tested the ability to form colonies and TBARS accumulation in a *Chlamydomonas* mutant sensitive to high light and observed a similar lag in TBARS formation (Baroli et al. 2004). It is likely that lower amounts of ROS can cause loss of colony forming ability, while the formation and accumulation of detectable levels of TBARS requires more time. However, we cannot exclude the alternate explanation that cell death itself is the cause of TBARS accumulation in the pgd1 mutant.

If the proposed hypothesis that TAG biosynthesis mitigates ROS formation at PSI following N deprivation is correct, we expect to identify more mutants deficient in TAG accumulation that lose viability following N deprivation. In fact, the essentiality of TAG accumulation opens new opportunities for additional forward genetic screens of mutants compromised in genes required for TAG biosynthesis and its regulation, or even photosynthetic electron transport.

CONCLUSIONS

The isolation of the pgd1 mutant led to the discovery of a galactolipid lipase that plays a role in TAG accumulation following N deprivation in *Chlamydomonas*. This finding was not predicted based on our current knowledge of lipid metabolism in seed plants. However, *Chlamydomonas* lacks PtdCho, which is the polar lipid in plants on which the modification of acyl groups followed by acyl exchange happens. Thus, one might wonder whether the TAG assembly pathway presented here is specific to *Chlamydomonas*. A cursory check suggests that there are possible orthologs of PGD1 in plants and other algae and that the hypothesis outlined in FIG. 9 may, therefore, also have some relevance to TAG biosynthesis in plants and other algae, at least under certain growth conditions and perhaps with modifications.

The pgd1 mutant also provides the means to experimentally demonstrate a long postulated role of TAG accumulation following nutrient deprivation in microalgae. Apparently, TAG accumulation relieves the reducing pressure on the electron transport chain under nutrient stress conditions when cells stop growing but still photosynthesize, and possibly alleviates the production of harmful ROS that can result in cell damage. Ultimately a better understanding of the assembly pathways for TAG and the physiological consequences of TAG accumulation will help shape our thinking of how to engineer improved algal feedstock for fuel, feed, and industrial chemicals.

An amino acid sequence for a PGD1 protein from *Chlamydomonas* includes, e.g., SEQ ID NO:1:

```
>PGD1_Protein_1117aa
MSQLLSHFVRVPTFASPDQVLREARDKERELQNARAPTDVSGFLAPVGVWELKHLRKLSSLTSLTYY

MHLVTPRRLQLMHGLDLVVTSRACDVRPYEHNRTAEECGADGDGMAVSFAEARQVYAELKRGTGGAS

GSGSNGAAAAPVAVAAGVSNIVALPRELPFVPLPGGATEGGEAGAEAAAGAAAAAAAAAGEGTGPGA

QGQGAGGLQLPLASTEAIGRMLRSPAEVVSAKLAEAALAASAAAAASPLGAAAESFYAGLASLPIPL

AGGLVGANNKAANTLLAPPNGAAASSSGGGGGSGGAAAASEVVGSSRGAQGADPADPGAPNTSGKAT

AASIAAMATAELRSRRLGGTGPAKTGGSGAASSGSSSGGIGAGGMAPVTAGGMRLSPAATAFSAPPA

ATVSSLASTDAGTALVPVASSSAASLTFSSSSAYSCPSEWFVVDDPASATRIFVIQGSDTLDHWKLN

LTFDPVVFEEPALGVKVHRGVYEAALVLYERFLPLVYEHLEASPFSKVTFTGHSIGGSMATLLMLMY

RNRGVLPPHSIATVYTFGAPAVFCQQQQPAVADASSACCNGSSSNGSSTPASGSSSPRSGSPGSASA

SSLPAGSGSGAGGMSLWALGLSGFGMGGASLAGGGSTSAPSSTAGLASVDGGAVAAGGGGSGFNSSG

LGFMSVEDPQAVSMPPGAAQAPSPASAPAPTAGPGHNSHSSHSKAGPAAAKSCACGVDGLLTRLGLA

PHVVRNVVMARDVVPRAFACDYSLVADILKGWGPAFREHCCLNRHGRKHLYYFVGRMCILQPDAWHS

FVGGDPEHPMLPPGPELYALAEPEDAAAARAHYPALSDLPILNAVTSNGHTRGSGGNGANAAVNAAV

NASGPSAAASGGGGGSQQPTAAAAVPSTANFGTALVASAAQRERDARGGGSRLQPRSVVEAVWEIMD

NPHPLETLADPGAYLASGSISRYHNPEHYTKALGRLTHLKRLAERRQHPHGQAQQKQAQPQAGEGGI

RSMFAGRNIRSFGGGVRSGSGSGSAGRRGLLHQQAASNGTAADAVLASGAAGAAAAAWGSAPQLADL

VSGNGGRASAGYEGGVWDSSDGLDLHLSDFMGASAVGAADPHACR
``` which is encoded by

```
PGD1_gDNA_6661 bp
                                                     (SEQ ID NO: 25)
CGTGAATGGCAAAACAATAGCAACAATGCAAGCGTACACCGGGCAAACCAAGCTTCGG

CCTGGGCGCGGGACAGGGAGTGCCGCTCCCACCGAGCCCAGGACTCGCACCTGTGTAGT

TACAAGAGTGCTAGCGCCACCTGAAGCGCCAGGAAGGAGGCCCCGTAGCGCCTCGTCTC

TGACGCAAGATGGGCAAGCGTCGCCCGCACCTTCAACGCCAACGACAGCAGCTTCTGTG

TGGTCGAGCACCACTAGCTATATGAGCCAGCTATTGTCGCACTTTGTGAGGGTTCCGAC

GTTTGCGTCGCCAGACCAGGTGAGCTCAGCGGTCGGAGATGCTGACGTCGCTCGGCGCA

CGCCTGGCTCGACGAGCTGACGGTGCACGCGGAGCTGGCGTGGCCAAGTTCTAAACCCG

CGCAATCCCGGCGTTATGGCAATGCGACAACGCAGGTCCTGCGTGAGGCGAGGGACAA

GGAGCGCGAGCTGCAGAACGCGAGGGCGCCCACGGATGTCAGCGGATTTCTTGCGCCC

GTTGGCGTTTGGGAGCTGAAGCACCTGCGCAAGCTGTCGTCCCTTACCAGCCTTACCTAC

TACATGCACCTGGTGACGGTGAGTGCGCGTGTTGGAGAGTTGGGGCGCGTGCGTGCGTG

CTCGCTAGCCGCCGCGTGGCGCGTAAGCGTGGCGCGCGAGCGTTAGCCAGGGTTAGCCT

CGCGGGTGTTCAGACCTGCAGCCGCCGCAGCTGCGGTGGGTAAGGGCCAGTTGGCTCTG

GAGCGGGGCAGCGGTGTTGCGCGGAGCCGCGGAGGGTTCGAGAAGGACCGCCGGGCAG

GTCCGCCGTAACGCACGCAGAGGGGGTAGCTGCCGAAGGTTGTTGGGCGCAGTGGAGG
```

-continued

```
AGTGGTTTCCCGGTACTCGGTAACGCACGTTGCCCAGACCCCGCCATCAAACCAGGACT
TGCCTGACAGCATCCGCCAGGGCCTGCCGGCGTCTGCCGTGCCGTGCTGCTGTGCTCGCT
CCGTCCTATTTAGCATTTCCTTTCGCCCTTCCTTCCCTGCCTCCTGAACCCCCCTGCCCCT
GTGCCGACCCCCGCACTACCTACCTCGCTCCCCTCCCACAGCCCCGGCGGCTGCAGCTG
ATGCACGGGCTGGACCTGGTGGTGACCAGCCGCGCCTGCGACGTGCGGCCGTACGAGCA
CAACCGCACCGCCGAGGAGTGCGGTGCCGACGGCGACGGCATGGCCGTCTCGTTCGCCG
AGGCGCGCCAGGTGTATGCCGAGCTGAAGCGCGGCACGGGCGGCGCCAGCGGCAGCGG
TAGCAACGGGGCGGCGGCGCCGGTGGCGGTGGCGGCGGGCGTGTCCAACATCGTG
GCGCTGCCGCGCGAGCTGCCGTTCGTGCCGCTTCCCGGCGGCGCGACGGAGGGTGGCGA
GGCGGGAGCGGAGGCCGCCGCCGGGGCGGCGGCAGCAGCCGCAGCCGCAGCTGGGGA
AGGCACCGGGCCGGGGGCCCAGGGGCAGGGGCAGGGGGCCTACAGCTGCCGTTGGCC
TCGACCGAGGCCATCGGCCGCATGCTGCGCAGCCCGGCGGAGGTGGTGTCGGCAAAGCT
TGCTGAGGCGGCCCTGGCGGCCTCGGCCGCCGCCGCCGCCAGCCCGCTCGGCGCCGCCG
CCGAGAGCTTTTACGCTGGGCTGGCCTCGCTGCCCATCCCGCTGGCCGGCGGCCTGGTG
GGCGCCAACAACAAGGCCGCCAACACACTGCTGGCGCCGCCGAACGGGGCGGCGGCCA
GCAGCAGTGGCGGCGGTGGTGGTAGCGGTGGCGCGGCGGCAGCGTCTGAGGTTGTGGG
CTCGTCGCGGGGCGCCCAGGGAGCGGACCCTGCGGACCCCGGCGCACCCAACACCAGC
GGCAAGGCCACTGCCGCCTCCATCGCGGCCATGGCAACTGCCGAGCTGCGCTCCCGCCG
CCTGGGCGGCACCGGTCCTGCCAAGACGGGGGGCAGCGGCGCCGCCAGCAGCGGCAGC
AGCAGCGGCGGTATTGGTGCGGGTGGCATGGCGCCAGTAACGGCTGGCGGCATGCGTTT
GTCACCCGCCGCCACCGCCTTCTCCGCCCCTCCCGCTGCCACCGTCTCCTCCCTGGCCTC
CACGGACGCCGGGACTGCGCTGGTGCCGGTGGCTTCATCCTCGGCGGCTTCCCTCACCTT
CTCCTCCAGCTCTGCCTACTCCTGCCCCTCAGAATGGTTTGTGGTGGACGACCCTGCCTC
GGCCACACGCATCTTCGTCATCCAGGTAGGAACCGTGGGAACCTTTAAGGAGTTGAGGT
GTGCGCCTAGAAAGTAAGGAAATGCGGGTAGGTGAATGCATGCAAGAAGACAGCGTTC
TGATACTACGGCAAACCCTCACAAGCGGTACTCGCGCCGCCTCCACAACAGGGCTCGGA
CACGCTGGACCACTGGAAGCTGAACCTGACGTTCGACCCGGTGGTGTTTGAGGAGCCGG
CCCTGGGCGTCAAGGTGCACCGCGGCGTGTACGAGGCGGCGCTGGTGCTGTACGAGCGC
TTCCTGCCGCTGGTGTACGAACACCTGGAGGCGTCGCCCTTCTCCAAGGTCACCTTCACG
GTGAGGGGTTGGAGGGGTGGGTGGAGAGGTGGCTTTCAGTTATCTCGCACGAGGACTGG
AAGTACCAAGCCAGGGGTAAGCGGGGTGGGCGGGAGCGGGGCAGACTGGAGAGGAGT
TCCAAGTGGACCGGGCACTCTACGGCACCTGTGCCTGTGCCTGACACCGCACCTGTGCT
GCCTCCATGCCGTCCGCCCCCCGACCCTCAGGGCCATTCCATCGGTGGCTCCATGGCCA
CGCTGCTGATGCTCATGTACCGCAACCGGGGCGTGCTGCCGCCGCACTCCATCGCCACC
GTCTACACCTTTGGCGCGCCCGCCGTGTTCTGCCAGCAGCAGCAACCGGCCGTAGCCGA
CGCCTCTTCGGCCTGCTGCAACGGCAGTAGCAGCAACGGCAGTAGCACGCCCGCCAGCG
GCAGCTCCAGCCCGAGGAGCGGCAGCCCCGGCTCAGCCTCGGCCTCGTCGCTGCCGGCC
GGCAGTGGCAGCGGTGCCGGCGGCATGTCGCTGTGGGCGCTGGGCCTGAGCGGCTTTGG
CATGGGCGGCGCCAGTCTGGCCGGCGGCGGCAGCACCAGCGCCCCTAGCAGTACCGCC
GGCCTGGCGAGTGTGGACGGCGGCGCCGTGGCGGCTGGCGGCGGCGGCAGCGGCTTCA
```

```
-continued
ACTCATCAGGGCTGGGCTTCATGAGCGTCGAGGTGCGGCCAGGGTTGGTCTGGGAGGGA

CGGGCTGGCTGCAAGGCGGCTACTGAGGGACGGACACGGGCTGTGTGTTCTGGCATGTC

AAGCACTTTCGCCGCTCGTAACCTATCTGCAAAACTCACTGTGTGTGTCGTGGTGTGCCA

CGCAGGACCCCCAGGCGGTCTCGATGCCGCCGGGCGCCGCCCAGGCGCCCTCGCCCGCG

TCCGCGCCGGCGCCCACCGCCGGCCCCGGCCACAACAGCCACAGCAGCCACAGCAAGG

CCGGCCCCGCCGCCGCCAAGAGCTGCGCCTGCGGTGTTGACGGGCTGCTGACGCGGCTG

GGGCTGGCGCCGCACGTGGTGCGCAACGTGGTGATGGCGCGGGACGTGGTGCCGCGCG

CCTTCGCGTGCGACTACAGCCTGGTGGCGGACATCCTCAAGGGCTGGGGGCCGGCCTTC

CGGGAGCACTGCTGCCTCAACAGGTGGGAGCAGGGGGGCGTGTGGCGGGCGTGCTGC

AGAGTGCTCGGGGCGGGTGGGGCGGGTGGCGCGGGGGGGACGCAGGCTGCAGCTGGGG

CTGTGCTTGGGCCGGACACGGGGCAACCATGGCCCGCGGTCAGGGCGCGGGTGCTGTAG

ATGGTGCGGTGGGTTGCGTGACCTGTGGCTCAGTTGCTGGCACGACTGACACGACGCCG

GGCGGCCCTCCGCGCAGGCACGGCCGCAAGCACCTGTACTACTTCGTGGGGCGCATGTG

CATCCTGCAGCCGGACGCCTGGCACAGCTTCGTGGGCGGCGACCCGGAGCACCCCATGC

TGCCGCCCGGCCCCGAGCTGTACGCGCTGGCGGAGCCCGAGGACGCCGCCGCTGCCCGC

GCCCACTACCCCGCCCTGTCCGACCTGCCCATCCTCAACGCCGTCACCAGCAATGGCCA

CACCCGCGGCAGCGGCGGCAACGGCGCCAACGCCGCCGTCAACGCCGCCGTCAACGCC

TCCGGCCCCAGCGCCGCCGCCTCCGGCGGCGGCGGCGGCTCGCAGCAGCCGACCGCGGC

GGCTGCTGTGCCGTCCACCGCCAACTTCGGCACGGCGCTGGTGGCGTCGGCGGCGCAGC

GGGAGCGCGACGCGCGCGGCGGCGGCTCTCGTCTGCAGCCGCGCAGTGTGGTGGAGGC

GGTGTGGGAGATCATGGACAACCCGCACCCTCTGGAGACACTGGCGGACCCGGGCGCCT

ACCTGGCCTCCGGCAGCATCTCCCGCTACCACAACCCGGAGCACTACACCAAGGCGCTG

GGCCGCCTGACGCACCTGAAGCGGCTGGCGGAGCGGCGGCAGCACCCGCACGGCCAGG

CGCAGCAGAAGCAGGCGCAGCCGCAGGCCGGCGAGGGCGGCATCCGCAGCATGTTCGC

GGGGCGCAACATCCGCAGCTTTGGCGGCGGTGTGCGCAGCGGCAGCGGCAGTGGCAGC

GCCGGCCGGCGGGGGCTGCTGCACCAGCAGGCGGCCTCCAACGGCACCGCGGCTGACG

CGGTGCTGGCCAGTGGCGCCGCCGGCGCGGCCGCCGCGGCCTGGGGCAGCGCGCCGCA

GCTGGCGGACCTGGTGAGCGGCAACGGCGGCCGCGCGAGTGCGGGCTACGAGGGCGGC

GTGTGGGACAGCAGTGACGGGCTGGACCTGCACCTCAGCGACTTCATGGGCGCCTCCGC

GGTGGGCGCCGCCGACCCACACGCCTGCCGGTGAGGCGGCGGCGACAGCGGCTGGGTG

TGGGCTGGATGCAGGTGACAGGCAAGGCGCAGTCAGAGGAGGCAGAAGCGGCAGAGG

CGGCAGAGGCGACGGAAGCGGCAAGTTGCAGCGTGCAGGAGCTGGAGTAGAGCCGCTG

TGCAGTGCGATCAGATGCAGCAGAGACGTGGAGCTTCAGCGCTTAGCGGGTGCGGCATG

AGCGCCTGAGCGCCTGAGCACGGGTGGACGCCGAGGAGGTCCGGAAGGGCGTTGCAC

GGGGTGAACGTGGCCAGGGGTCAGCCTTATTACGGTGCGTAATGGTTGGGGTCTGCGAC

TCGGTTTGCAACTGCGTATGCATATACCAATGGTGGTGGCGCGTCGCGAGCCGCTCTGC

GGGCTGCCGCAATATGTGCGGCGGCCGCAACACGGGCACATCAGCGCATTATACTATTC

CCTTACTGAAGGGCAGCGGAGTGAGCTGTGGACGGCATGGGTATAGGTGTCGGCGCCGC

CGGGGCCTCTGACCCGCCACGCCTGCGCCGGGCCAGGGGCTGCACAGACAGGCTAAGG

ATCGATCTAGCAGACCGTCAAGGTCATTGCCTTGTTGATTGGTATGCTCTGTACTACTAT

GTATTCCGGCTTTCGAGTGCCGGGCAGTGACTGCGGCCAAGCAGAACTGCCCGTGACCT
```

-continued

```
CCTCCGGGTTAGGCAGCCAGGGGCCTGCGCCTCTGCGCGTGGGGAGCAGTGCCGGGCAG

CCCGGGCACAAATGAGAGCGAGTGTGCCTCTTCTATTAGCCATGTGCCAAATGTTCTTA

ACTGTTATCCAAAAGTGCTGTGTGCGATTTCATGTCTGCTGGTTTGTGCGTACATAGGGA

CCCACAGATCCCCTTCCTCCCATGCGCCGCATGCTGCCGCTGCCACAATTTGTGCCGGCG

CTGCGTGTGTGGGGGGAACCGGGGTTGCGTGACGTGCGTGTGAAGAGTGTGCATGTGTC

CCGCGGTGTCGCGGCATTTGCTGTAGTTGTGCTGTTGGGTGCTAGGAGCGGGGCGAGAG

TGAAGAGAACCCTTCATGTCAGGGCCCAGCGATCGTCTTGCTGGGGCACCTTGCGTGTG

CTGTGCTTTGCTATTCTATTCCTCTTGAGAGTAGCTGCGCTGCTCAGAGGCATGCAGTGT

GTAGAGTTGACGATCTGTTGCAGTGTTGCATAGAGCCACGCTGGAGCTGCAGTTAGTCC

AGAGGTGTCACGGTGCTTGCGGCGACGCGTCTGCCGCGGTACTCCTACGGCTCCGTGTT

GCACCGCGGCAGCCCAAGCGCCTCGGCAGCTGCAGCATAAGGCGTTTGAGCGGGTAGG

TCCATGTGTCTCTGTCCTATTCATCGCGGTAGCTGATCCAGTAGCTGGTAGGCGGTGCGC

TTCGGTGTAGGTTGAACTAGCAGATTTCCCGGGCAATGCGTGTGGCAGCCCAAGCTGAA

CAGGGCAGGTGGTGGCTGGGACGATGCTCCCGCGCAGGAACGATGCTCCCGCGCACCTC

ACACTCATGCTCAAGGTTGACGCCCCGATTGGGGATTTTTGTGCAGGTGTTAAAGCTATG

CCCCGTACTTGGGGTGTGTTCGCCGTGTGGCGTGAAGGCGTGAAGTTACTCCTTGAATTT

GAGACATAGACAGGTGGTGCAGCGCGTGAAGCGCGTGTCAAGGCTGCGCGCAGCCCAT

GTAAGGTCCGAGATGC
```

Where the mRNA transcript has a DNA sequence of

```
>PGD1_transcript_5302 bp
                                                            (SEQ ID NO: 26)
CGTGAATGGCAAAACAATAGCAACAATGCAAGCGTACACCGGGCAAACCAAGCTTCGG

CCTGGGCGCGGGACAGGGAGTGCCGCTCCCACCGAGCCCAGGACTCGCACCTGTGTAGT

TACAAGAGTGCTAGCGCCACCTGAAGCGCCAGGAAGGAGGCCCCGTAGCGCCTCGTCTC

TGACGCAAGATGGGCAAGCGTCGCCCGCACCTTCAACGCCAACGACAGCAGCTTCTGTG

TGGTCGAGCACCACTAGCTATATGAGCCAGCTATTGTCGCACTTTGTGAGGGTTCCGAC

GTTTGCGTCGCCAGACCAGGTCCTGCGTGAGGCGAGGGACAAGGAGCGCGAGCTGCAG

AACGCGAGGGCGCCCACGGATGTCAGCGGATTTCTTGCGCCCGTTGGCGTTTGGGAGCT

GAAGCACCTGCGCAAGCTGTCGTCCCTTACCAGCCTTACCTACTACATGCACCTGGTGAC

GCCCCGGCGGCTGCAGCTGATGCACGGGCTGGACCTGGTGGTGACCAGCCGCGCCTGCG

ACGTGCGGCCGTACGAGCACAACCGCACCGCCGAGGAGTGCGGTGCCGACGGCGACGG

CATGGCCGTCTCGTTCGCCGAGGCGCGCCAGGTGTATGCCGAGCTGAAGCGCGGCACGG

GCGGCGCCAGCGGCAGCGGTAGCAACGGGGCGGCGGCGGCGCCGGTGGCGGTGGCGGC

GGGCGTGTCCAACATCGTGGCGCTGCCGCGCGAGCTGCCGTTCGTGCCGCTTCCCGGCG

GCGCGACGGAGGGTGGCGAGGCGGGAGCGGAGGCCGCCGCCGGGGCGGCGGCAGCAG

CCGCAGCCGCAGCTGGGGAAGGCACCGGGCCGGGGGCCCAGGGGCAGGGGCAGGGG

GCCTACAGCTGCCGTTGGCCTCGACCGAGGCCATCGGCCGCATGCTGCGCAGCCCGGCG

GAGGTGGTGTCGGCAAAGCTTGCTGAGGCGGCCCTGGCGGCCTCGGCCGCCGCCGCCGC

CAGCCCGCTCGGCGCCGCCGCCGAGAGCTTTTACGCTGGGCTGGCCTCGCTGCCCATCC

CGCTGGCCGGCGGCCTGGTGGGCGCCAACAACAAGGCCGCCAACACACTGCTGGCGCC
```

-continued

```
GCCGAACGGGGCGGCGGCCAGCAGCAGTGGCGGCGGTGGTGGTAGCGGTGGCGCGGCG
GCAGCGTCTGAGGTTGTGGGCTCGTCGCGGGCGCCCAGGGAGCGGACCCTGCGGACCC
CGGCGCACCCAACACCAGCGGCAAGGCCACTGCCGCCTCCATCGCGGCCATGGCAACTG
CCGAGCTGCGCTCCCGCCGCCTGGGCGGCACCGGTCCTGCCAAGACGGGGGGCAGCGG
CGCCGCCAGCAGCGGCAGCAGCAGCGGCGGTATTGGTGCGGGTGGCATGGCGCCAGTA
ACGGCTGGCGGCATGCGTTTGTCACCCGCCGCCACCGCCTTCTCCGCCCCTCCCGCTGCC
ACCGTCTCCTCCCTGGCCTCCACGGACGCCGGGACTGCGCTGGTGCCGGTGGCTTCATCC
TCGGCGGCTTCCCTCACCTTCTCCTCCAGCTCTGCCTACTCCTGCCCCTCAGAATGGTTTG
TGGTGGACGACCCTGCCTCGGCCACACGCATCTTCGTCATCCAGGGCTCGGACACGCTG
GACCACTGGAAGCTGAACCTGACGTTCGACCCGGTGGTGTTTGAGGAGCCGGCCCTGGG
CGTCAAGGTGCACCGCGGCGTGTACGAGGCGGCGCTGGTGCTGTACGAGCGCTTCCTGC
CGCTGGTGTACGAACACCTGGAGGCGTCGCCCTTCTCCAAGGTCACCTTCACGGGCCAT
TCCATCGGTGGCTCCATGGCCACGCTGCTGATGCTCATGTACCGCAACCGGGGCGTGCT
GCCGCCGCACTCCATCGCCACCGTCTACACCTTTGGCGCGCCCGCCGTGTTCTGCCAGCA
GCAGCAACCGGCCGTAGCCGACGCCTCTTCGGCCTGCTGCAACGGCAGTAGCAGCAACG
GCAGTAGCACGCCCGCCAGCGGCAGCTCCAGCCCGAGGAGCGGCAGCCCCGGCTCAGC
CTCGGCCTCGTCGCTGCCGGCCGGCAGTGGCAGCGGTGCCGGCGGCATGTCGCTGTGGG
CGCTGGGCCTGAGCGGCTTTGGCATGGGCGGCGCCAGTCTGGCCGGCGGCGGCAGCACC
AGCGCCCCTAGCAGTACCGCCGGCCTGGCGAGTGTGGACGGCGGCGCCGTGGCGGCTG
GCGGCGGCGGCAGCGGCTTCAACTCATCAGGGCTGGGCTTCATGAGCGTCGAGGACCCC
CAGGCGGTCTCGATGCCGCCGGGCGCCGCCCAGGCGCCCTCGCCCGCGTCCGCGCCGGC
GCCCACCGCCGGCCCCGGCCACAACAGCCACAGCAGCCACAGCAAGGCCGGCCCCGCC
GCCGCCAAGAGCTGCGCCTGCGGTGTTGACGGGCTGCTGACGCGGCTGGGGCTGGCGCC
GCACGTGGTGCGCAACGTGGTGATGGCGCGGGACGTGGTGCCGCGCGCCTTCGCGTGCG
ACTACAGCCTGGTGGCGGACATCCTCAAGGGCTGGGGGCCGGCCTTCCGGGAGCACTGC
TGCCTCAACAGGCACGGCCGCAAGCACCTGTACTACTTCGTGGGGCGCATGTGCATCCT
GCAGCCGGACGCCTGGCACAGCTTCGTGGGCGGCGACCCGGAGCACCCCATGCTGCCGC
CCGGCCCCGAGCTGTACGCGCTGGCGGAGCCCGAGGACGCCGCCGCTGCCCGCGCCCAC
TACCCCGCCCTGTCCGACCTGCCCATCCTCAACGCCGTCACCAGCAATGGCCACACCCG
CGGCAGCGGCGGCAACGGCGCCAACGCCGCCGTCAACGCCGCCGTCAACGCCTCCGGC
CCCAGCGCCGCCGCCTCCGGCGGCGGCGGCGGCTCGCAGCAGCCGACCGCGGCGGCTG
CTGTGCCGTCCACCGCCAACTTCGGCACGGCGCTGGTGGCGTCGGCGGCGCAGCGGGAG
CGCGACGCGCGCGGCGGCGGCTCTCGTCTGCAGCCGCGCAGTGTGGTGGAGGCGGTGTG
GGAGATCATGGACAACCCGCACCCTCTGGAGACACTGGCGGACCCGGGCGCCTACCTGG
CCTCCGGCAGCATCTCCCGCTACCACAACCCGGAGCACTACACCAAGGCGCTGGGCCGC
CTGACGCACCTGAAGCGGCTGGCGGAGCGGCGGCAGCACCCGCACGGCCAGGCGCAGC
AGAAGCAGGCGCAGCCGCAGGCCGGCGAGGGCGGCATCCGCAGCATGTTCGCGGGGCG
CAACATCCGCAGCTTTGGCGGCGGTGTGCGCAGCGGCAGCGGCAGTGGCAGCGCCGGC
CGGCGGGGGCTGCTGCACCAGCAGGCGGCCTCCAACGGCACCGCGGCTGACGCGGTGC
TGGCCAGTGGCGCCGCCGGCGCGGCCGCCGCGGCCTGGGCAGCGCGCCGCAGCTGGC
GGACCTGGTGAGCGGCAACGGCGGCCGCGCGAGTGCGGGCTACGAGGGCGGCGTGTGG
```

-continued

```
GACAGCAGTGACGGGCTGGACCTGCACCTCAGCGACTTCATGGGCGCCTCCGCGGTGGG
CGCCGCCGACCCACACGCCTGCCGGTGAGGCGGCGGCGACAGCGGCTGGGTGTGGGCT
GGATGCAGGTGACAGGCAAGGCGCAGTCAGAGGAGGCAGAAGCGGCAGAGGCGGCAG
AGGCGACGGAAGCGGCAAGTTGCAGCGTGCAGGAGCTGGAGTAGAGCCGCTGTGCAGT
GCGATCAGATGCAGCAGAGACGTGGAGCTTCAGCGCTTAGCGGGTGCGGCATGAGCGC
CTGAGCGCCTGAGCACGGGTGGACGCCGAGGAGGTCCGGAAGGGCGTTGCACGGGGT
GAACGTGGCCAGGGGTCAGCCTTATTACGGTGCGTAATGGTTGGGGTCTGCGACTCGGT
TTGCAACTGCGTATGCATATACCAATGGTGGTGGCGCGTCGCGAGCCGCTCTGCGGGCT
GCCGCAATATGTGCGGCGGCCGCAACACGGGCACATCAGCGCATTATACTATTCCCTTA
CTGAAGGGCAGCGGAGTGAGCTGTGGACGGCATGGGTATAGGTGTCGGCGCCGCCGGG
GCCTCTGACCCGCCACGCCTGCGCCGGGCCAGGGGCTGCACAGACAGGCTAAGGATCG
ATCTAGCAGACCGTCAAGGTCATTGCCTTGTTGATTGGTATGCTCTGTACTACTATGTAT
TCCGGCTTTCGAGTGCCGGGCAGTGACTGCGGCCAAGCAGAACTGCCCGTGACCTCCTC
CGGGTTAGGCAGCCAGGGGCCTGCGCCTCTGCGCGTGGGGAGCAGTGCCGGGCAGCCC
GGGCACAAATGAGAGCGAGTGTGCCTCTTCTATTAGCCATGTGCCAAATGTTCTTAACT
GTTATCCAAAAGTGCTGTGTGCGATTTCATGTCTGCTGGTTTGTGCGTACATAGGGACCC
ACAGATCCCCTTCCTCCCATGCGCCGCATGCTGCCGCTGCCACAATTTGTGCCGGCGCTG
CGTGTGTGGGGGGAACCGGGGTTGCGTGACGTGCGTGTGAAGAGTGTGCATGTGTCCCG
CGGTGTCGCGGCATTTGCTGTAGTTGTGCTGTTGGGTGCTAGGAGCGGGGCGAGAGTGA
AGAGAACCCTTCATGTCAGGGCCCAGCGATCGTCTTGCTGGGGCACCTTGCGTGTGCTG
TGCTTTGCTATTCTATTCCTCTTGAGAGTAGCTGCGCTGCTCAGAGGCATGCAGTGTGTA
GAGTTGACGATCTGTTGCAGTGTTGCATAGAGCCACGCTGGAGCTGCAGTTAGTCCAGA
GGTGTCACGGTGCTTGCGGCGACGCGTCTGCCGCGGTACTCCTACGGCTCCGTGTTGCAC
CGCGGCAGCCCAAGCGCCTCGGCAGCTGCAGCATAAGGCGTTTGAGCGGGTAGGTCCAT
GTGTCTCTGTCCTATTCATCGCGGTAGCTGATCCAGTAGCTGGTAGGCGGTGCGCTTCGG
TGTAGGTTGAACTAGCAGATTTCCCGGGCAATGCGTGTGGCAGCCCAAGCTGAACAGGG
CAGGTGGTGGCTGGGACGATGCTCCCGCGCAGGAACGATGCTCCCGCGCACCTCACACT
CATGCTCAAGGTTGACGCCCCGATTGGGGATTTTTGTGCAGGTGTTAAAGCTATGCCCCG
TACTTGGGGTGTGTTCGCCGTGTGGCGTGAAGGCGTGAAGTTACTCCTTGAATTTGAGAC
ATAGACAGGTGGTGCAGCGCGTGAAGCGCGTGTCAAGGCTGCGCGCAGCCCATGTAAG
GTCCGAGATGC
```

With the following coding sequence

```
>PGD1_CDC_3354 bp
                                                       (SEQ ID NO: 27)
ATGAGCCAGCTATTGTCGCACTTTGTGAGGGTTCCGACGTTTGCGTCGCCAGACCAGGTC
CTGCGTGAGGCGAGGGACAAGGAGCGCGAGCTGCAGAACGCGAGGGCGCCCACGGATG
TCAGCGGATTTCTTGCGCCCGTTGGCGTTTGGGAGCTGAAGCACCTGCGCAAGCTGTCGT
CCCTTACCAGCCTTACCTACTACATGCACCTGGTGACGCCCCGGCGGCTGCAGCTGATGC
ACGGGCTGGACCTGGTGGTGACCAGCCGCGCCTGCGACGTGCGGCCGTACGAGCACAA
CCGCACCGCCGAGGAGTGCGGTGCCGACGGCGACGGCATGGCCGTCTCGTTCGCCGAGG
```

-continued

```
CGCGCCAGGTGTATGCCGAGCTGAAGCGCGGCACGGGCGGCGCCAGCGGCAGCGGTAG

CAACGGGGCGGCGGCGGCGCCGGTGGCGGTGGCGGCGGGCGTGTCCAACATCGTGGCG

CTGCCGCGCGAGCTGCCGTTCGTGCCGCTTCCCGGCGGCGCGACGGAGGGTGGCGAGGC

GGGAGCGGAGGCCGCCGCCGGGGCGGCGGCAGCAGCCGCAGCCGCAGCTGGGGAAGG

CACCGGGCCGGGGGCCCAGGGGCAGGGGGCAGGGGGCCTACAGCTGCCGTTGGCCTCG

ACCGAGGCCATCGGCCGCATGCTGCGCAGCCCGGCGGAGGTGGTGTCGGCAAAGCTTGC

TGAGGCGGCCCTGGCGGCCTCGGCCGCCGCCGCCGCCAGCCCGCTCGGCGCCGCCGCCG

AGAGCTTTTACGCTGGGCTGGCCTCGCTGCCCATCCCGCTGGCCGGCGGCCTGGTGGGC

GCCAACAACAAGGCCGCCAACACACTGCTGGCGCCGCCGAACGGGGCGGCGGCCAGCA

GCAGTGGCGGCGGTGGTGGTAGCGGTGGCGCGGCGGCAGCGTCTGAGGTTGTGGGCTC

GTCGCGGGGCGCCCAGGGAGCGGACCCTGCGGACCCCGGCGCACCCAACACCAGCGGC

AAGGCCACTGCCGCCTCCATCGCGGCCATGGCAACTGCCGAGCTGCGCTCCCGCCGCCT

GGGCGGCACCGGTCCTGCCAAGACGGGGGGCAGCGGCGCCGCCAGCAGCGGCAGCAGC

AGCGGCGGTATTGGTGCGGGTGGCATGGCGCCAGTAACGGCTGGCGGCATGCGTTTGTC

ACCCGCCGCCACCGCCTTCTCCGCCCCTCCCGCTGCCACCGTCTCCTCCCTGGCCTCCAC

GGACGCCGGGACTGCGCTGGTGCCGGTGGCTTCATCCTCGGCGGCTTCCCTCACCTTCTC

CTCCAGCTCTGCCTACTCCTGCCCCTCAGAATGGTTTGTGGTGGACGACCCTGCCTCGGC

CACACGCATCTTCGTCATCCAGGGCTCGGACACGCTGGACCACTGGAAGCTGAACCTGA

CGTTCGACCCGGTGGTGTTTGAGGAGCCGGCCCTGGGCGTCAAGGTGCACCGCGGCGTG

TACGAGGCGGCGCTGGTGCTGTACGAGCGCTTCCTGCCGCTGGTGTACGAACACCTGGA

GGCGTCGCCCTTCTCCAAGGTCACCTTCACGGGCCATTCCATCGGTGGCTCCATGGCCAC

GCTGCTGATGCTCATGTACCGCAACCGGGGCGTGCTGCCGCCGCACTCCATCGCCACCG

TCTACACCTTTGGCGCGCCCGCCGTGTTCTGCCAGCAGCAGCAACCGGCCGTAGCCGAC

GCCTCTTCGGCCTGCTGCAACGGCAGTAGCAGCAACGGCAGTAGCACGCCCGCCAGCGG

CAGCTCCAGCCCGAGGAGCGGCAGCCCCGGCTCAGCCTCGGCCTCGTCGCTGCCGGCCG

GCAGTGGCAGCGGTGCCGGCGGCATGTCGCTGTGGGCGCTGGGCCTGAGCGGCTTTGGC

ATGGGCGGCGCCAGTCTGGCCGGCGGCGGCAGCACCAGCGCCCCTAGCAGTACCGCCG

GCCTGGCGAGTGTGGACGGCGGCGCCGTGGCGGCTGGCGGCGGCGGCAGCGGCTTCAA

CTCATCAGGGCTGGGCTTCATGAGCGTCGAGGACCCCCAGGCGGTCTCGATGCCGCCGG

GCGCCGCCCAGGCGCCCTCGCCCGCGTCCGCGCCGGCGCCCACCGCCGGCCCCGGCCAC

AACAGCCACAGCAGCCACAGCAAGGCCGGCCCCGCCGCCGCCAAGAGCTGCGCCTGCG

GTGTTGACGGGCTGCTGACGCGGCTGGGGCTGGCGCCGCACGTGGTGCGCAACGTGGTG

ATGGCGCGGGACGTGGTGCCGCGCGCCTTCGCGTGCGACTACAGCCTGGTGGCGGACAT

CCTCAAGGGCTGGGGGCCGGCCTTCCGGGAGCACTGCTGCCTCAACAGGCACGGCCGCA

AGCACCTGTACTACTTCGTGGGGCGCATGTGCATCCTGCAGCCGGACGCCTGGCACAGC

TTCGTGGGCGGCGACCCGGAGCACCCCATGCTGCCGCCCGGCCCCGAGCTGTACGCGCT

GGCGGAGCCCGAGGACGCCGCCGCTGCCCGCGCCCACTACCCCGCCCTGTCCGACCTGC

CCATCCTCAACGCCGTCACCAGCAATGGCCACACCCCGCGGCAGCGGCGGCAACGGCGCC

AACGCCGCCGTCAACGCCGCCGTCAACGCCTCCGGCCCCAGCGCCGCCGCCTCCGGCGG
```

-continued

```
CGGCGGCGGCTCGCAGCAGCCGACCGCGGCGGCTGCTGTGCCGTCCACCGCCAACTTCG
GCACGGCGCTGGTGGCGTCGGCGGCGCAGCGGGAGCGCGACGCGCGCGGCGGCGGCTC
TCGTCTGCAGCCGCGCAGTGTGGTGGAGGCGGTGTGGGAGATCATGGACAACCCGCACC
CTCTGGAGACACTGGCGGACCCGGGCGCCTACCTGGCCTCCGGCAGCATCTCCCGCTAC
CACAACCCGGAGCACTACACCAAGGCGCTGGGCCGCCTGACGCACCTGAAGCGGCTGG
CGGAGCGGCGGCAGCACCCGCACGGCCAGGCGCAGCAGAAGCAGGCGCAGCCGCAGGC
CGGCGAGGGCGGCATCCGCAGCATGTTCGCGGGGCGCAACATCCGCAGCTTTGGCGGCG
GTGTGCGCAGCGGCAGCGGCAGTGGCAGCGCCGGCCGGCGGGGCTGCTGCACCAGCA
GGCGGCCTCCAACGGCACCGCGGCTGACGCGGTGCTGGCCAGTGGCGCCGCCGGCGCG
GCCGCCGCGGCCTGGGGCAGCGCGCCGCAGCTGGCGGACCTGGTGAGCGGCAACGGCG
GCCGCGCGAGTGCGGGCTACGAGGGCGGCGTGTGGGACAGCAGTGACGGGCTGGACCT
GCACCTCAGCGACTTCATGGGCGCCTCCGCGGTGGGCGCCGCCGACCCACACGCCTGCC
GGTGA
```

See also Accession No. EDP03131 having SEQ ID NO:2:

```
  1 msqllshfvr vptfaspdqv lreardkere lqnaraptdv sgflapvgvw elkhlrklss
 61 ltsltyymhl vtprrlqlmh gldlvvtsra cdvrpyehnr taeecgadgd gmavsfaear
121 qgadpadpga pntsgkataa siaamatael rsrrlggtew fvvddpasat rifviqgsdt
181 ldhwklnitf dpvvfeepal gvkvhrgvye aalvlyerfl plvyehleas pfskvtftgh
241 siggsmatll mlmyrnrgvl pphsiatvyt fgapavfcqq qqpascacgv dglltrlgla
301 phvvrnvvma rdvvprafac dyslvadilk gwgpafrehc clnrhgrkhl yyfvgrmcil
361 qpdawhsfvg gdpehpmlpp gpelyalaep edaaaarahy palsdlpiln avveavweim
421 dnphpletla dpgaylasgs isryhnpehy tkalgrlthl krlaerrqhp hgqaqqkqaq
481 pqageggirs mfagrnirsf gggvrsgsgs gsagrrgllh qqaasngtaa davlasgaag
541 aaaaawgsap qladlvsgng grasagyegg vwdssdgldl hlsdfmgasa vgaadphacr
``` or XP_001693105 having SEQ ID NO: 3:

```
  1 msqllshfvr vptfaspdqv lreardkere lqnaraptdv sgflapvgvw elkhlrklss
 61 ltsltyymhl vtprrlqlmh gldlvvtsra cdvrpyehnr taeecgadgd gmavsfaear
121 qgadpadpga pntsgkataa siaamatael rsrrlggtew fvvddpasat rifviqgsdt
181 ldhwklnltf dpvvfeepal gvkvhrgvye aalvlyerfl plvyehleas pfskvtftgh
241 siggsmatll mlmyrnrgvl pphsiatvyt fgapavfcqq qqpascacgv dglltrlgla
301 phvvrnvvma rdvvprafac dyslvadilk gwgpafrehc clnrhgrkhl yyfvgrmcil
361 qpdawhsfvg gdpehpmlpp gpelyalaep edaaaarahy palsdlpiln avveavweim
421 dnphpletla dpgaylasgs isryhnpehy tkalgrlthl krlaerrqhp hgqaqqkqaq
481 pqageggirs mfagrnirsf gggvrsgsgs gsagrrgllh qqaasngtaa davlasgaag
541 aaaaawgsap qladlvsgng grasagyegg vwdssdgldl hlsdfmgasa vgaadphacr
```

Exemplary homologs to SEQ ID NOs. 1-3 include but are not limited to those having Accession Nos. EIE241331, XP_002957248, XP_001766893.1, XP_02876633.1, XP_01757678.1, NP_101727.2, EEC71102, CBI369301, or XP_0033535965, the disclosures of which are incorporated by reference herein.

REFERENCES

Aslanidis, C. and de Jong, P. J. (1990) Ligation-independent cloning of PCR products (LIC-PCR). Nucleic Acids Res. 18:6069-6074.

Baroli, I., Do, A. D., Yamane, T., and Niyogi, K. K. (2003) Zeaxanthin accumulation in the absence of a functional xanthophyll cycle protects *Chlamydomonas reinhardtii* from photooxidative stress. Plant Cell 15:992-1008.

Baroli, I., Gutman, B. L., Ledford, H. K., Shin, J. W., Chin, B. L., Havaux, M., and Niyogi, K. K. (2004) Photo-oxidative stress in a xanthophyll-deficient mutant of *Chlamydomonas*. J. Biol. Chem. 279:6337-6344.

Bates, P. D., Durrett, T. P., Ohlrogge, J. B., and Pollard, M. (2009) Analysis of acyl fluxes through multiple pathways of triacylglycerol synthesis in developing soybean embryos. Plant Physiol. 150:55-72.

Bates, P. D., Ohlrogge, J. B., and Pollard, M. (2007) Incorporation of newly synthesized fatty acids into cytosolic glycerolipids in pea leaves occurs via acyl editing. J. Biol. Chem. 282:31206-31216.

Benning, C. (2009) Mechanisms of lipid transport involved in organelle biogenesis in plant cells. Annu Rev. Cell Dev. Biol. 25:71-91.

Benning, C., Huang, Z. H., and Gage, D. A. (1995) Accumulation of a novel glycolipid and a betaine lipid in cells of *Rhodobacter sphaeroides* grown under phosphate limitation. Arch. Biochem. Biophys. 317:103-111.

Berthold, P., Schmitt, R., and Mages, W. (2002) An engineered *Streptomyces hygroscopicus* aph 7" gene mediates dominant resistance against hygromycin B in *Chlamydomonas reinhardtii*. Protist 153:401-412.

Browse, J., Warwick, N., Somerville, C. R., and Slack, C. R. (1986) Fluxes through the prokaryotic and eukaryotic pathways of lipid synthesis in the '16:3' plant *Arabidopsis thaliana*. Biochem. J. 235:25-31.

Castruita, M., Casero, D., Karpowicz, S. J., Kropat, J., Vieler, A., Hsieh, S. I., Yan, W. H., Cokus, S., Loo, J. A., Benning, C., Pellegrini, M., and Merchant, S. S. (2011) Systems biology approach in *Chlamydomonas* reveals connections between copper nutrition and multiple metabolic steps. Plant Cell 23:1273-1292.

Chang, C. W., Moseley, J. L., Wykoff, D., and Grossman, A. R. (2005) The LPB 1 gene is important for acclimation of *Chlamydomonas* reinhardtii to phosphorus and sulfur deprivation. Plant Physiol. 138:319-329.

Chen, H. H., Wickrema, A., and Jaworski, J. G. (1988) Acyl-acyl-carrier protein: lysomonogalactosyldiacylglycerol acyltransferase from the cyanobacterium *Anabaena variabilis*. Biochim. Biophys. Acta 963:493-500.

Chen, W., Sommerfeld, M., and Hu, Q. A. (2011) Microwave-assisted Nile red method for in vivo quantification of neutral lipids in microalgae. Biores. Technol. 102:135-141.

Davies, J. P., Yildiz, F. H., and Grossman, A. (1996) Sac1, a putative regulator that is critical for survival of *Chlamydomonas reinhardtii* during sulfur deprivation. EMBO J. 15:2150-2159.

Durrett, T. P., Benning, C., and Ohlrogge, J. (2008) Plant triacylglycerols as feedstocks for the production of biofuels. Plant J. 54:593-607.

Fan, J., Yan, C., Andre, C., Shanklin, J., Schwender, J., and Xu, C. (2012) Oil accumulation is controlled by carbon precursor supply for fatty acid synthesis in *Chlamydomonas* reinhardtii. Plant Cell Physiol. 53:1380-1390.

Fan, J. L., Andre, C., and Xu, C. C. (2011) A chloroplast pathway for the de novo biosynthesis of triacylglycerol in *Chlamydomonas reinhardtii*. FEBS Lett. 585:1985-1991.

Fernandez, E., Schnell, R., Ranum, L. P. W., Hussey, S. C., Silflow, C. D., and Lefebvre, P. A. (1989) Isolation and characterization of the nitrate reductase structural gene of *Chlamydomonas reinhardtii*. Proc. Natl. Acad. Sci. U.S.A. 86:6449-6453.

Fischer, B. B., Krieger-Liszkay, A., Hideg, E., Snyrychova, I., Wiesendanger, M., and Eggen, R. I. (2007) Role of singlet oxygen in chloroplast to nucleus retrograde signaling in *Chlamydomonas reinhardtii*. FEBS Lett. 581:5555-5560.

Fischer, W., Heinz, E., and Zeus, M. (1973) The suitability of lipase from *Rhizopus arrhizus* delemar for analysis of fatty acid distribution in dihexosyl diglycerides, phospholipids and plant sulfolipids. Hoppe Seylers. Z. Physiol. Chem. 354:1115-1123.

Giroud, C. and Eichenberger, W. (1989) Lipids of *Chlamydomonas reinhardtii*—Incorporation of [C-14] acetate, [C-14] palmitate and [C-14] oleate into different lipids and evidence for lipid-linked desaturation of fatty acids. Plant Cell Physiol. 30:121-128.

Giroud, C., Gerber, A., and Eichenberger, W. (1988) Lipids of *Chlamydomonas reinhardtii*—Analysis of molecular species and intracellular site(s) of biosynthesis. Plant Cell Physiol. 29:587-595.

Goodson, C., Roth, R., Wang, Z. T., and Goodenough, U. (2011) Structural correlates of cytoplasmic and chloroplast lipid body synthesis in *Chlamydomonas reinhardtii* and stimulation of lipid body production with acetate boost. Eukaryot. Cell 10:1592-1606.

Grossman, A. R., Harris, E. E., Hauser, C., Lefebvre, P. A., Martinez, D., Rokhsar, D., Shrager, J., Silflow, C. D., Stern, D., Vallon, O., and Zhang, Z. D. (2003) *Chlamydomonas reinhardtii* at the crossroads of genomics. Eukaryot. Cell 2:1137-1150.

Harris, E. H. (1989) *Chlamydomonas* Sourcebook. New York: Academic Press.

Heinz, E. and Roughan, G. (1983) Similarities and differences in lipid metabolism of chloroplasts isolated from 18:3 and 16:3 plants. Plant Physiol. 72:273-279.

Hu, Q., Sommerfeld, M., Jarvis, E., Ghirardi, M., Posewitz, M., Seibert, M., and Darzins, A. (2008) Microalgal triacylglycerols as feedstocks for biofuel production: perspectives and advances. Plant J. 54:621-639.

James, G. O., Hocart, C. H., Hillier, W., Chen, H. C., Kordbacheh, F., Price, G. D., and Djordjevic, M. A. (2011) Fatty acid profiling of *Chlamydomonas reinhardtii* under nitrogen deprivation. Biores. Technol. 102:3343-3351.

Joyard, J., Block, M. A., and Douce, R. (1991) Molecular aspects of plastid envelope biochemistry. Eur. J. Biochem. 199:489-509.

Kimura, K., Yamaoka, M., and Kamisaka, Y. (2004) Rapid estimation of lipids in oleaginous fungi and yeasts using Nile red fluorescence. J. Microbiol. Meth. 56:331-338.

Kindle, K. L. (1990) High-frequency nuclear transformation of *Chlamydomonas reinhardtii*. Proc. Natl. Acad. Sci. U.S.A. 87:1228-1232.

Kunst, L., Browse, J., and Somerville, C. (1988) Altered regulation of lipid biosynthesis in a mutant of *Arabidopsis* deficient in chloroplast glycerol-3-phosphate acyltransferase activity. Proc. Natl. Acad. Sci. U.S.A. 85:4143-4147.

Li, X., Benning, C., and Kuo, M. H. (2012) Rapid triacylglycerol turnover in *Chlamydomonas reinhardtii* requires a lipase with broad substrate specificity. Eukaryot. Cell:Epub ahead of print.

Liu, B. and Benning, C. (2012) Lipid metabolism in microalgae distinguishes itself. Curr. Opin. Biotechnol.:Epub. ahead of print.

Livak, K. J. and Schmittgen, T. D. (2001) Analysis of relative gene expression data using real-time quantitative PCR and the 2(T)(-Delta Delta C) method. Methods 25:402-408.

Lu, B. and Benning, C. (2009) A 25-amino acid sequence of the *Arabidopsis* TGD2 protein is sufficient for specific binding of phosphatidic acid. J. Biol. Chem. 284:17420-17427.

Lu, Y., Savage, L. J., Ajjawi, I., Imre, K. M., Yoder, D. W., Benning, C., Dellapenna, D., Ohlrogge, J. B., Osteryoung, K. W., Weber, A. P., Wilkerson, C. G., and Last, R. L. (2008) New connections across pathways and cellular processes: industrialized mutant screening reveals novel associations between diverse phenotypes in *Arabidopsis*. Plant Physiol. 146:1482-1500.

Luo, J., Xu, X., Hall, H., Hyland, E. M., Boeke, J. D., Hazbun, T., and Kuo, M. H. (2010) Histone h3 exerts a key function in mitotic checkpoint control. Mol. Cell. Biol. 30:537-549.

Ma, H., Kunes, S., Schatz, P. J., and Botstein, D. (1987) Plasmid construction by homologous recombination in yeast. Gene 58:201-216.

Mehler, A. H. (1951) Studies on reactions of illuminated chloroplasts. 2. Stimulation and inhibition of the reaction with molecular oxygen. Arch. Biochem. Biophys. 34:339-351.

Merchant et al. (2007) The *Chlamydomonas* genome reveals the evolution of key animal and plant functions. Science 318:245-251.

Miller, R., Wu, G., Deshpande, R. R., Vieler, A., Gaertner, K., Li, X., Moellering, E. R., Zauner, S., Cornish, A., Liu, B., Bullard, B., Sears, B. B., Kuo, M. H., Hegg, E. L., Shachar-Hill, Y., Shiu, S. H., and Benning, C. (2010) Changes in transcript abundance in *Chlamydomonas reinhardtii* following nitrogen-deprivation predict diversion of metabolism. Plant Physiol. 154:1737-1752.

Moellering, E. R. and Benning, C. (2010) RNA interference silencing of a major lipid droplet protein affects lipid droplet size in *Chlamydomonas reinhardtii*. Eukaryot. Cell 9:97-106.

Moellering, E. R., Muthan, B., and Benning, C. (2010) Freezing tolerance in plants requires lipid remodeling at the outer chloroplast membrane. Science 330:226-228.

Newman, S. M., Boynton, J. E., Gillham, N. W., Randolphanderson, B. L., Johnson, A. M., and Harris, E. H. (1990) Transformation of chloroplast ribosomal-RNA genes in *Chlamydomonas*—Molecular and genetic characterization of integration events. Genetics 126:875-888.

Nguyen, H. T., Mishra, G., Whittle, E., Pidkowich, M. S., Bevan, S. A., Merlo, A. O., Walsh, T. A., and Shanklin, J. (2010) Metabolic engineering of seeds can achieve levels of omega-7 fatty acids comparable with the highest levels found in natural plant sources. Plant Physiol 154:1897-1904.

Ohlrogge, J. B., Kuhn, D. N., and Stumpf, P. K. (1979) Subcellular localization of acyl carrier protein in leaf protoplasts of *Spinacia oleracea*. Proc. Natl. Acad. Sci. U.S.A. 76:1194-1198.

Riekhof, W. R., Sears, B. B., and Benning, C. (2005) Annotation of genes involved in glycerolipid biosynthesis in *Chlamydomonas reinhardtii*: Discovery of the betaine lipid synthase BTA1 (Cr). Eukaryot. Cell 4:242-252.

Robert, G., Melchiorre, M., Trippi, V., and Lascano, H. R. (2009) Apoplastic superoxide level in wheat protoplast under photooxidative stress is regulated by chloroplast ROS generation: Effects on the antioxidant system. Plant Science 177:168-174.

Rossak, M., Schafer, A., Xu, N., Gage, D. A., and Benning, C. (1997) Accumulation of sulfoquinovosyl-1-O-dihydroxyacetone in a sulfolipid-deficient mutant of *Rhodobacter sphaeroides* inactivated in sqdC. Arch. Biochem. Biophys. 340:219-230.

Roughan, P. G. and Slack, C. R. (1982) Cellular organization of glycerolipid metabolism. Annu Rev. Plant Physiol. Plant Mol. Biol. 33:97-132.

Rousseeuw, P. J. and Croux, C. (1993) Alternatives to the median absolute deviation. Am. Stat. Assoc. 88:1273-1283.

Sato, N. and Murata, N. (1991) Transition of lipid phase in aqueous dispersions of diacylglyceryltrimethylhomoserine. Biochim. Biophys. Acta 1082:108-111.

Shimojima, M., Ohta, H., Iwamatsu, A., Masuda, T., Shioi, Y., and Takamiya, K. (1997) Cloning of the gene for monogalactosyldiacylglycerol synthase and its evolutionary origin. Proc. Natl. Acad. Sci. U.S.A 94:333-337.

Shulaev, V. and Oliver, D. J. (2006) Metabolic and proteomic markers for oxidative stress. New tools for reactive oxygen species research. Plant Physiol. 141:367-372.

Siebertz, H. P. and Heinz, E. (1977) Labelling experiments on the origin of hexa- and octadectrienoic acids in galactolipids from leaves. Z. Naturforsch. 32c:193-205.

Tan, G. H., Gao, Y., Shi, M., Zhang, X. Y., He, S. P., Cheng, Z. L., and An, C. C. (2005) SiteFinding-PCR: A simple and efficient PCR method for chromosome walking Nucleic Acids Res. 33:e122.

Trebst, A., Harth, E., and Draber, W. (1970) On a new Inhibitor of photosynthetic electron transport in isolated chloroplasts. Z. Naturforsch. B 25:1157-1159.

Wang, Z. T., Ullrich, N., Joo, S., Waffenschmidt, S., and Goodenough, U. (2009) Algal lipid bodies: Stress induction, purification, and biochemical characterization in wild-type and starchless *Chlamydomonas reinhardtii*. Eukaryot. Cell 8:1856-1868.

Wen, F., Xing, D., and Zhang, L. (2008) Hydrogen peroxide is involved in high blue light-induced chloroplast avoidance movements in *Arabidopsis*. J. Exp. Bot. 59:2891-2901.

Weyer, K. M., Bush, D. R., Darzins, A., and Willson, B. D. (2010) Theoretical maximum algal oil production. Bioenergy Res. 3:204-213.

Work, V. H., Radakovits, R., Jinkerson, R. E., Meuser, J. E., Elliott, L. G., Vinyard, D. J., Laurens, L. M. L., Dismukes, G. C., and Posewitz, M. C. (2010) Increased lipid accumulation in the *Chlamydomonas* reinhardtii sta7-10 starchless isoamylase mutant and increased carbohydrate synthesis in complemented strains. Eukaryot. Cell 9:1251-1261.

Xu, C., Fan, J., Riekhof, W., Froehlich, J. E., and Benning, C. (2003) A permease-like protein involved in ER to thylakoid lipid transfer in *Arabidopsis*. EMBO J. 22:2370-2379

Zieger, R. and Egle, K. (1965) Zur quantitativen Analyse der Chloroplasten pigmente. I. Kritische Üperbrüfung der spektralphotometrischen Chlorophyllbestimmung. Beitr. Biol. Pflanz. 41:11-37.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A recombinant cell comprising a vector having a heterologous promoter operably linked to a nucleotide sequence encoding a polypeptide which is a galactoglycerolipid lipase having at least 95% amino acid sequence identity to a polypeptide having SEQ ID NO: 1.

2. The recombinant cell of claim 1 which is an algal cell, a bacterial cell or a plant cell.

3. The recombinant cell of claim 1 which is *E. coli*.

4. The recombinant cell of claim 1 which is a corn, cannola canola, palm, soybean, peanut, or walnut cell.

5. The recombinant cell of claim 1 which is a red, green or brown alga.

6. The recombinant cell of claim 1 which is a *Chlamydomonas*, *Nannochloropsis*, Phaeophyceae or *Phytophthora infestans* cell.

7. The recombinant cell of claim 2 which is an *Archaeplastida, Rhizaria, Excavata, Chromista,* or *Alveolata* cell.

8. The recombinant cell of claim 1 which is a green algae, Rhodophyta (red algae), Glaucophyta, Chlorarachniophytes, Euglenids, Bacillariophyceae (Diatoms), Axodine, Bolidomonas, Eustigmatophyceae, Phaeophyceae (brown algae), Chrysophyceae (golden algae), Raphidophyceae, Synurophyceae, Xanthophyceae (yellow-green algae), Cryptophyta, Dinoflagellates or Haptophyta cell.

9. A method to produce triacylglycerol (TAG) comprising:
providing the recombinant cell of claim 1; and
culturing the cell under conditions that produce oil having TAG.

10. The method of claim 9 further comprising isolating TAG.

11. The method of claim 9 wherein the cell is a plant cell in a plant.

12. The method of claim 9 wherein the plant is a corn, cannola, palm, soybean, peanut, or walnut plant.

13. The method of claim 9 wherein the cell is a brown, red or green algal cell.

14. A method to increase oil production, comprising:
providing the recombinant cell of claim 1; and
culturing the cell under conditions that produce oil in an amount that is increased relative to a corresponding non-recombinant cell.

15. The method of claim 14 further comprising isolating the oil.

16. The method of claim 14 wherein the cell is a plant cell in a plant.

17. The method of claim 16 wherein the plant is a corn, cannola, palm, soybean, peanut, or walnut plant.

18. The method of claim 14 wherein the cell is a brown, red or green algal cell.

19. The method of claim 14 wherein the amount of monounsaturated fatty acids in the oil is increased.

20. A recombinant DNA construct comprising a heterologous promoter operably linked to a nucleotide sequence encoding a polypeptide which is a galactoglycerolipid lipase having at least 95% amino acid sequence identity to a polypeptide having SEQ ID NO:1.

21. The recombinant cell of claim 1 wherein the nucleotide sequence is at least 95% identical to SEQ ID NO:2.

* * * * *

SEQUENCE LISTING

<160> NUMBER OF SEQ ID NOS: 27

<210> SEQ ID NO 1
<211> LENGTH: 1117
<212> TYPE: PRT
<213> ORGANISM: Chlamydomonas reinhardtii

<400> SEQUENCE: 1

Met Ser Gln Leu Leu Ser His Phe Val Arg Val Pro Thr Phe Ala Ser
1               5                   10                  15

Pro Asp Gln Val Leu Arg Glu Ala Arg Asp Lys Glu Arg Glu Leu Gln
            20                  25                  30

Asn Ala Arg Ala Pro Thr Asp Val Ser Gly Phe Leu Ala Pro Val Gly
        35                  40                  45

Val Trp Glu Leu Lys His Leu Arg Lys Leu Ser Ser Leu Thr Ser Leu
50                  55                  60

Thr Tyr Tyr Met His Leu Val Thr Pro Arg Arg Leu Gln Leu Met His
65                  70                  75                  80

Gly Leu Asp Leu Val Val Thr Ser Arg Ala Cys Asp Val Arg Pro Tyr
                85                  90                  95

Glu His Asn Arg Thr Ala Glu Glu Cys Gly Ala Asp Gly Asp Gly Met
            100                 105                 110

Ala Val Ser Phe Ala Glu Ala Arg Gln Val Tyr Ala Glu Leu Lys Arg
        115                 120                 125

Gly Thr Gly Gly Ala Ser Gly Ser Gly Asn Gly Ala Ala Ala
        130                 135                 140

Pro Val Ala Val Ala Gly Val Ser Asn Ile Val Ala Leu Pro Arg
145                 150                 155                 160

Glu Leu Pro Phe Val Pro Leu Pro Gly Gly Ala Thr Glu Gly Gly Glu
                165                 170                 175

Ala Gly Ala Glu Ala Ala Ala Gly Ala Ala Ala Ala Ala Ala
        180                 185                 190

Ala Gly Glu Gly Thr Gly Pro Gly Ala Gln Gly Gln Gly Ala Gly Gly
        195                 200                 205

Leu Gln Leu Pro Leu Ala Ser Thr Glu Ala Ile Gly Arg Met Leu Arg
    210                 215                 220

Ser Pro Ala Glu Val Val Ser Ala Lys Leu Ala Glu Ala Ala Leu Ala
225                 230                 235                 240

Ala Ser Ala Ala Ala Ala Ser Pro Leu Gly Ala Ala Ala Glu Ser
                245                 250                 255

Phe Tyr Ala Gly Leu Ala Ser Leu Pro Ile Pro Leu Ala Gly Gly Leu
                260                 265                 270

Val Gly Ala Asn Asn Lys Ala Ala Asn Thr Leu Leu Ala Pro Pro Asn
            275                 280                 285

Gly Ala Ala Ala Ser Ser Ser Gly Gly Gly Gly Ser Gly Gly Ala
        290                 295                 300

Ala Ala Ala Ser Glu Val Val Gly Ser Ser Arg Gly Ala Gln Gly Ala
305                 310                 315                 320

Asp Pro Ala Asp Pro Gly Ala Pro Asn Thr Ser Gly Lys Ala Thr Ala
                325                 330                 335

Ala Ser Ile Ala Ala Met Ala Thr Ala Glu Leu Arg Ser Arg Arg Leu
            340                 345                 350

Gly Gly Thr Gly Pro Ala Lys Thr Gly Gly Ser Gly Ala Ala Ser Ser
        355                 360                 365

-continued

Gly Ser Ser Gly Gly Ile Gly Ala Gly Gly Met Ala Pro Val Thr
370                 375                 380

Ala Gly Gly Met Arg Leu Ser Pro Ala Ala Thr Ala Phe Ser Ala Pro
385                 390                 395                 400

Pro Ala Ala Thr Val Ser Ser Leu Ala Ser Thr Asp Ala Gly Thr Ala
        405                 410                 415

Leu Val Pro Val Ala Ser Ser Ala Ala Ser Leu Thr Phe Ser Ser
            420                 425                 430

Ser Ser Ala Tyr Ser Cys Pro Ser Glu Trp Phe Val Asp Asp Pro
        435                 440                 445

Ala Ser Ala Thr Arg Ile Phe Val Ile Gln Gly Ser Asp Thr Leu Asp
450                 455                 460

His Trp Lys Leu Asn Leu Thr Phe Asp Pro Val Val Phe Glu Glu Pro
465                 470                 475                 480

Ala Leu Gly Val Lys Val His Arg Gly Val Tyr Glu Ala Ala Leu Val
            485                 490                 495

Leu Tyr Glu Arg Phe Leu Pro Leu Val Tyr Glu His Leu Glu Ala Ser
            500                 505                 510

Pro Phe Ser Lys Val Thr Phe Thr Gly His Ser Ile Gly Gly Ser Met
        515                 520                 525

Ala Thr Leu Leu Met Leu Met Tyr Arg Asn Arg Gly Val Leu Pro Pro
530                 535                 540

His Ser Ile Ala Thr Val Tyr Thr Phe Gly Ala Pro Ala Val Phe Cys
545                 550                 555                 560

Gln Gln Gln Gln Pro Ala Val Ala Asp Ala Ser Ser Ala Cys Cys Asn
                565                 570                 575

Gly Ser Ser Ser Asn Gly Ser Ser Thr Pro Ala Ser Gly Ser Ser Ser
            580                 585                 590

Pro Arg Ser Gly Ser Pro Gly Ser Ala Ser Ala Ser Ser Leu Pro Ala
        595                 600                 605

Gly Ser Gly Ser Gly Ala Gly Gly Met Ser Leu Trp Ala Leu Gly Leu
    610                 615                 620

Ser Gly Phe Gly Met Gly Gly Ala Ser Leu Ala Gly Gly Gly Ser Thr
625                 630                 635                 640

Ser Ala Pro Ser Ser Thr Ala Gly Leu Ala Ser Val Asp Gly Gly Ala
            645                 650                 655

Val Ala Ala Gly Gly Gly Gly Ser Gly Phe Asn Ser Ser Gly Leu Gly
                660                 665                 670

Phe Met Ser Val Glu Asp Pro Gln Ala Val Ser Met Pro Pro Gly Ala
            675                 680                 685

Ala Gln Ala Pro Ser Pro Ala Ser Ala Pro Ala Pro Thr Ala Gly Pro
        690                 695                 700

Gly His Asn Ser His Ser Ser His Ser Lys Ala Gly Pro Ala Ala Ala
705                 710                 715                 720

Lys Ser Cys Ala Cys Gly Val Asp Gly Leu Leu Thr Arg Leu Gly Leu
                725                 730                 735

Ala Pro His Val Val Arg Asn Val Val Met Ala Arg Asp Val Val Pro
            740                 745                 750

Arg Ala Phe Ala Cys Asp Tyr Ser Leu Val Ala Asp Ile Leu Lys Gly
                755                 760                 765

Trp Gly Pro Ala Phe Arg Glu His Cys Cys Leu Asn Arg His Gly Arg
    770                 775                 780

Lys His Leu Tyr Tyr Phe Val Gly Arg Met Cys Ile Leu Gln Pro Asp

```
            785                 790                 795                 800
Ala Trp His Ser Phe Val Gly Gly Asp Pro Glu His Pro Met Leu Pro
                    805                 810                 815

Pro Gly Pro Glu Leu Tyr Ala Leu Ala Glu Pro Glu Asp Ala Ala Ala
                820                 825                 830

Ala Arg Ala His Tyr Pro Ala Leu Ser Asp Leu Pro Ile Leu Asn Ala
            835                 840                 845

Val Thr Ser Asn Gly His Thr Arg Gly Ser Gly Asn Gly Ala Asn
    850                 855                 860

Ala Ala Val Asn Ala Ala Val Asn Ala Ser Gly Pro Ser Ala Ala Ala
865                 870                 875                 880

Ser Gly Gly Gly Gly Ser Gln Gln Pro Thr Ala Ala Ala Val
                    885                 890                 895

Pro Ser Thr Ala Asn Phe Gly Thr Ala Leu Val Ala Ser Ala Ala Gln
                900                 905                 910

Arg Glu Arg Asp Ala Arg Gly Gly Gly Ser Arg Leu Gln Pro Arg Ser
            915                 920                 925

Val Val Glu Ala Val Trp Glu Ile Met Asp Asn Pro His Pro Leu Glu
    930                 935                 940

Thr Leu Ala Asp Pro Gly Ala Tyr Leu Ala Ser Gly Ser Ile Ser Arg
945                 950                 955                 960

Tyr His Asn Pro Glu His Tyr Thr Lys Ala Leu Gly Arg Leu Thr His
                965                 970                 975

Leu Lys Arg Leu Ala Glu Arg Gln His Pro His Gly Gln Ala Gln
            980                 985                 990

Gln Lys Gln Ala Gln Pro Gln Ala Gly Glu Gly Gly Ile Arg Ser Met
        995                 1000                1005

Phe Ala Gly Arg Asn Ile Arg Ser Phe Gly Gly Gly Val Arg Ser Gly
    1010                1015                1020

Ser Gly Ser Gly Ser Ala Gly Arg Arg Gly Leu Leu His Gln Gln Ala
1025                1030                1035                1040

Ala Ser Asn Gly Thr Ala Ala Asp Ala Val Leu Ala Ser Gly Ala Ala
                1045                1050                1055

Gly Ala Ala Ala Ala Ala Trp Gly Ser Ala Pro Gln Leu Ala Asp Leu
            1060                1065                1070

Val Ser Gly Asn Gly Gly Arg Ala Ser Ala Gly Tyr Glu Gly Gly Val
        1075                1080                1085

Trp Asp Ser Ser Asp Gly Leu Asp Leu His Leu Ser Asp Phe Met Gly
    1090                1095                1100

Ala Ser Ala Val Gly Ala Ala Asp Pro His Ala Cys Arg
1105                1110                1115

<210> SEQ ID NO 2
<211> LENGTH: 600
<212> TYPE: PRT
<213> ORGANISM: Chlamydomonas reinhardtii

<400> SEQUENCE: 2

Met Ser Gln Leu Leu Ser His Phe Val Arg Val Pro Thr Phe Ala Ser
1               5                   10                  15

Pro Asp Gln Val Leu Arg Glu Ala Arg Asp Lys Glu Arg Glu Leu Gln
                20                  25                  30

Asn Ala Arg Ala Pro Thr Asp Val Ser Gly Phe Leu Ala Pro Val Gly
            35                  40                  45
```

```
Val Trp Glu Leu Lys His Leu Arg Lys Leu Ser Ser Leu Thr Ser Leu
 50                  55                  60
Thr Tyr Tyr Met His Leu Val Thr Pro Arg Arg Leu Gln Leu Met His
 65                  70                  75                  80
Gly Leu Asp Leu Val Val Thr Ser Arg Ala Cys Asp Val Arg Pro Tyr
                     85                  90                  95
Glu His Asn Arg Thr Ala Glu Glu Cys Gly Ala Asp Gly Asp Gly Met
                100                 105                 110
Ala Val Ser Phe Ala Glu Ala Arg Gln Gly Ala Asp Pro Ala Asp Pro
            115                 120                 125
Gly Ala Pro Asn Thr Ser Gly Lys Ala Thr Ala Ser Ile Ala Ala
130                 135                 140
Met Ala Thr Ala Glu Leu Arg Ser Arg Arg Leu Gly Gly Thr Glu Trp
145                 150                 155                 160
Phe Val Val Asp Asp Pro Ala Ser Ala Thr Arg Ile Phe Val Ile Gln
                165                 170                 175
Gly Ser Asp Thr Leu Asp His Trp Lys Leu Asn Leu Thr Phe Asp Pro
                180                 185                 190
Val Val Phe Glu Glu Pro Ala Leu Gly Val Lys Val His Arg Gly Val
                195                 200                 205
Tyr Glu Ala Ala Leu Val Leu Tyr Glu Arg Phe Leu Pro Leu Val Tyr
210                 215                 220
Glu His Leu Glu Ala Ser Pro Phe Ser Lys Val Thr Phe Thr Gly His
225                 230                 235                 240
Ser Ile Gly Gly Ser Met Ala Thr Leu Leu Met Leu Tyr Arg Asn
                245                 250                 255
Arg Gly Val Leu Pro Pro His Ser Ile Ala Thr Val Tyr Thr Phe Gly
                260                 265                 270
Ala Pro Ala Val Phe Cys Gln Gln Gln Pro Ala Ser Cys Ala Cys
            275                 280                 285
Gly Val Asp Gly Leu Leu Thr Arg Leu Gly Leu Ala Pro His Val Val
            290                 295                 300
Arg Asn Val Val Met Ala Arg Asp Val Val Pro Arg Ala Phe Ala Cys
305                 310                 315                 320
Asp Tyr Ser Leu Val Ala Asp Ile Leu Lys Gly Trp Gly Pro Ala Phe
                325                 330                 335
Arg Glu His Cys Cys Leu Asn Arg His Gly Arg Lys His Leu Tyr Tyr
                340                 345                 350
Phe Val Gly Arg Met Cys Ile Leu Gln Pro Asp Ala Trp His Ser Phe
            355                 360                 365
Val Gly Gly Asp Pro Glu His Pro Met Leu Pro Pro Gly Pro Glu Leu
370                 375                 380
Tyr Ala Leu Ala Glu Pro Glu Asp Ala Ala Ala Arg Ala His Tyr
385                 390                 395                 400
Pro Ala Leu Ser Asp Leu Pro Ile Leu Asn Ala Val Glu Ala Val
                405                 410                 415
Trp Glu Ile Met Asp Asn Pro His Pro Leu Glu Thr Leu Ala Asp Pro
                420                 425                 430
Gly Ala Tyr Leu Ala Ser Gly Ser Ile Ser Arg Tyr His Asn Pro Glu
                435                 440                 445
His Tyr Thr Lys Ala Leu Gly Arg Leu Thr His Leu Lys Arg Leu Ala
        450                 455                 460
Glu Arg Arg Gln His Pro His Gly Gln Ala Gln Gln Lys Gln Ala Gln
```

```
            465                 470                 475                 480
Pro Gln Ala Gly Glu Gly Gly Ile Arg Ser Met Phe Ala Gly Arg Asn
                485                 490                 495

Ile Arg Ser Phe Gly Gly Gly Val Arg Ser Gly Ser Gly Ser Gly Ser
                500                 505                 510

Ala Gly Arg Arg Gly Leu Leu His Gln Gln Ala Ala Ser Asn Gly Thr
                515                 520                 525

Ala Ala Asp Ala Val Leu Ala Ser Gly Ala Ala Gly Ala Ala Ala Ala
                530                 535                 540

Ala Trp Gly Ser Ala Pro Gln Leu Ala Asp Leu Val Ser Gly Asn Gly
545                 550                 555                 560

Gly Arg Ala Ser Ala Gly Tyr Glu Gly Val Trp Asp Ser Ser Asp
                565                 570                 575

Gly Leu Asp Leu His Leu Ser Asp Phe Met Gly Ala Ser Ala Val Gly
                580                 585                 590

Ala Ala Asp Pro His Ala Cys Arg
                595                 600
```

<210> SEQ ID NO 3
<211> LENGTH: 600
<212> TYPE: PRT
<213> ORGANISM: Chlamydomonas reinhardtii

<400> SEQUENCE: 3

```
Met Ser Gln Leu Leu Ser His Phe Val Arg Val Pro Thr Phe Ala Ser
1               5                   10                  15

Pro Asp Gln Val Leu Arg Glu Ala Arg Asp Lys Glu Arg Glu Leu Gln
                20                  25                  30

Asn Ala Arg Ala Pro Thr Asp Val Ser Gly Phe Leu Ala Pro Val Gly
                35                  40                  45

Val Trp Glu Leu Lys His Leu Arg Lys Leu Ser Ser Leu Thr Ser Leu
                50                  55                  60

Thr Tyr Tyr Met His Leu Val Thr Pro Arg Arg Leu Gln Leu Met His
65              70                  75                  80

Gly Leu Asp Leu Val Val Thr Ser Arg Ala Cys Asp Val Arg Pro Tyr
                85                  90                  95

Glu His Asn Arg Thr Ala Glu Glu Cys Gly Ala Asp Gly Asp Gly Met
                100                 105                 110

Ala Val Ser Phe Ala Glu Ala Arg Gln Gly Ala Asp Pro Ala Asp Pro
                115                 120                 125

Gly Ala Pro Asn Thr Ser Gly Lys Ala Thr Ala Ala Ser Ile Ala Ala
                130                 135                 140

Met Ala Thr Ala Glu Leu Arg Ser Arg Leu Gly Gly Thr Glu Trp
145                 150                 155                 160

Phe Val Val Asp Asp Pro Ala Ser Ala Thr Arg Ile Phe Val Ile Gln
                165                 170                 175

Gly Ser Asp Thr Leu Asp His Trp Lys Leu Asn Leu Thr Phe Asp Pro
                180                 185                 190

Val Val Phe Glu Glu Pro Ala Leu Gly Val Lys Val His Arg Gly Val
                195                 200                 205

Tyr Glu Ala Ala Leu Val Leu Tyr Glu Arg Phe Leu Pro Leu Val Tyr
                210                 215                 220

Glu His Leu Glu Ala Ser Pro Phe Ser Lys Val Thr Phe Thr Gly His
225                 230                 235                 240
```

-continued

```
Ser Ile Gly Gly Ser Met Ala Thr Leu Leu Met Leu Met Tyr Arg Asn
                245                 250                 255

Arg Gly Val Leu Pro Pro His Ser Ile Ala Thr Val Tyr Thr Phe Gly
            260                 265                 270

Ala Pro Ala Val Phe Cys Gln Gln Gln Pro Ala Ser Cys Ala Cys
        275                 280                 285

Gly Val Asp Gly Leu Leu Thr Arg Leu Gly Leu Ala Pro His Val Val
    290                 295                 300

Arg Asn Val Val Met Ala Arg Asp Val Val Pro Arg Ala Phe Ala Cys
305                 310                 315                 320

Asp Tyr Ser Leu Val Ala Asp Ile Leu Lys Gly Trp Gly Pro Ala Phe
                325                 330                 335

Arg Glu His Cys Cys Leu Asn Arg His Gly Arg Lys His Leu Tyr Tyr
            340                 345                 350

Phe Val Gly Arg Met Cys Ile Leu Gln Pro Asp Ala Trp His Ser Phe
        355                 360                 365

Val Gly Gly Asp Pro Glu His Pro Met Leu Pro Pro Gly Pro Glu Leu
    370                 375                 380

Tyr Ala Leu Ala Glu Pro Glu Asp Ala Ala Ala Arg Ala His Tyr
385                 390                 395                 400

Pro Ala Leu Ser Asp Leu Pro Ile Leu Asn Ala Val Val Glu Ala Val
                405                 410                 415

Trp Glu Ile Met Asp Asn Pro His Pro Leu Glu Thr Leu Ala Asp Pro
            420                 425                 430

Gly Ala Tyr Leu Ala Ser Gly Ser Ile Ser Arg Tyr His Asn Pro Glu
        435                 440                 445

His Tyr Thr Lys Ala Leu Gly Arg Leu Thr His Leu Lys Arg Leu Ala
    450                 455                 460

Glu Arg Arg Gln His Pro His Gly Gln Ala Gln Gln Lys Gln Ala Gln
465                 470                 475                 480

Pro Gln Ala Gly Glu Gly Gly Ile Arg Ser Met Phe Ala Gly Arg Asn
                485                 490                 495

Ile Arg Ser Phe Gly Gly Gly Val Arg Ser Gly Ser Gly Ser Gly Ser
            500                 505                 510

Ala Gly Arg Arg Gly Leu Leu His Gln Gln Ala Ala Ser Asn Gly Thr
        515                 520                 525

Ala Ala Asp Ala Val Leu Ala Ser Gly Ala Ala Gly Ala Ala Ala Ala
    530                 535                 540

Ala Trp Gly Ser Ala Pro Gln Leu Ala Asp Leu Val Ser Gly Asn Gly
545                 550                 555                 560

Gly Arg Ala Ser Ala Gly Tyr Glu Gly Gly Val Trp Asp Ser Ser Asp
                565                 570                 575

Gly Leu Asp Leu His Leu Ser Asp Phe Met Gly Ala Ser Ala Val Gly
            580                 585                 590

Ala Ala Asp Pro His Ala Cys Arg
        595                 600
```

<210> SEQ ID NO 4
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 4

```
accaacatct tcgtggacct                                                   20

<210> SEQ ID NO 5
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 5
ctcctcgaac acctcgaagt                                                   20

<210> SEQ ID NO 6
<211> LENGTH: 61
<212> TYPE: DNA
<213> ORGANISM: Artificial Sequence
<220> FEATURE:
<223> OTHER INFORMATION: A synthetic oligonucleotide primer
<221> NAME/KEY: misc_feature
<222> LOCATION: (1)...(61)
<223> OTHER INFORMATION: n = A,T,C or G

<400> SEQUENCE: 6
cacgacacgc tactcaacac accacctcgc acagcgtcct caagcggccg cnnnnnngca       60
t                                                                       61

<210> SEQ ID NO 7
<211> LENGTH: 61
<212> TYPE: DNA
<213> ORGANISM: Artificial Sequence
<220> FEATURE:
<223> OTHER INFORMATION: A synthetic oligonucleotide primer
<221> NAME/KEY: misc_feature
<222> LOCATION: (1)...(61)
<223> OTHER INFORMATION: n = A,T,C or G

<400> SEQUENCE: 7
cacgacacgc tactcaacac accacctcgc acagcgtcct caagcggccg cnnnnnngca       60
g                                                                       61

<210> SEQ ID NO 8
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 8
cacgacacgc tactcaacac                                                   20

<210> SEQ ID NO 9
<211> LENGTH: 24
<212> TYPE: DNA
<213> ORGANISM: Artificial Sequence
<220> FEATURE:
<223> OTHER INFORMATION: A synthetic oligonucleotide primer

<400> SEQUENCE: 9
actcaacaca ccacctcgca cagc                                              24

<210> SEQ ID NO 10
<211> LENGTH: 20
<212> TYPE: DNA
<213> ORGANISM: Artificial Sequence
<220> FEATURE:
<223> OTHER INFORMATION: A synthetic oligonucleotide primer
```

<400> SEQUENCE: 10
actgctcgcc ttcaccttcc                                        20

<210> SEQ ID NO 11
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 11
ctggatctct ccggcttcac                                        20

<210> SEQ ID NO 12
<211> LENGTH: 19
<212> TYPE: DNA
<213> ORGANISM: Artificial Sequence
<220> FEATURE:
<223> OTHER INFORMATION: A synthetic oligonucleotide primer

<400> SEQUENCE: 12 atagggttc cgcgcacat                                          19

<210> SEQ ID NO 13
<211> LENGTH: 19
<212> TYPE: DNA
<213> ORGANISM: Artificial Sequence
<220> FEATURE:
<223> OTHER INFORMATION: A synthetic oligonucleotide primer

<400> SEQUENCE: 13
ccgaaaagtg ccacctgac                                         19

<210> SEQ ID NO 14
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 14
gtcatcccat ggaagcttgg                                        20

<210> SEQ ID NO 15
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 15
acatcgtgaa tggcaaaaca                                        20

<210> SEQ ID NO 16
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 16
attgcgcggg tttagaactt                                        20

<210> SEQ ID NO 17

```
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 17
agccagctat tgtcgcactt                                              20

<210> SEQ ID NO 18
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 18
caagaaatcc gctgacatcc                                              20

<210> SEQ ID NO 19
<211> LENGTH: 60
<212> TYPE: DNA
<213> ORGANISM: Artificial Sequence
<220> FEATURE:
<223> OTHER INFORMATION: A synthetic oligonucleotide primer

<400> SEQUENCE: 19
tatccatatg acgttccaga ttacgctgct cagtgcggcc gcatgagcca gctattgtcg  60

<210> SEQ ID NO 20
<211> LENGTH: 60
<212> TYPE: DNA
<213> ORGANISM: Artificial Sequence
<220> FEATURE:
<223> OTHER INFORMATION: A synthetic oligonucleotide primer

<400> SEQUENCE: 20
gaatttcgac ggtatcgggg ggatccacta gttctagcta gatcaccggc aggcgtgtgg  60

<210> SEQ ID NO 21
<211> LENGTH: 25
<212> TYPE: DNA
<213> ORGANISM: Artificial Sequence
<220> FEATURE:
<223> OTHER INFORMATION: A synthetic oligonucleotide primer

<400> SEQUENCE: 21
ggatccgatg agccagctat tgtcg                                        25

<210> SEQ ID NO 22
<211> LENGTH: 24
<212> TYPE: DNA
<213> ORGANISM: Artificial Sequence
<220> FEATURE:
<223> OTHER INFORMATION: A synthetic oligonucleotide primer

<400> SEQUENCE: 22
gtcgacccgg caggcgtgtg ggtc                                         24

<210> SEQ ID NO 23
<211> LENGTH: 31
<212> TYPE: DNA
<213> ORGANISM: Artificial Sequence
<220> FEATURE:
<223> OTHER INFORMATION: A synthetic oligonucleotide primer

<400> SEQUENCE: 23
```

```
aaagaggcgc gtcatgagcc agctattgtc g                              31
```

<210> SEQ ID NO 24
<211> LENGTH: 29
<212> TYPE: DNA
<213> ORGANISM: Artificial Sequence
<220> FEATURE:
<223> OTHER INFORMATION: A synthetic oligonucleotide primer

<400> SEQUENCE: 24

```
cggaaggcgc gtcaccggca ggcgtgtgg                                 29
```

<210> SEQ ID NO 25
<211> LENGTH: 6661
<212> TYPE: DNA
<213> ORGANISM: Chlamydomonas reinhardtii

<400> SEQUENCE: 25

```
cgtgaatggc aaacaatag caacaatgca agcgtacacc gggcaaacca agcttcggcc    60
tgggcgcggg acagggagtg ccgctcccac cgagcccagg actcgcacct gtgtagttac   120
aagagtgcta gcgccacctg aagcgccagg aaggaggccc cgtagcgcct cgtctctgac   180
gcaagatggg caagcgtcgc ccgcaccttc aacgccaacg acagcagctt ctgtgtggtc   240
gagcaccact agctatatga gccagctatt gtcgcacttt gtgagggttc cgacgtttgc   300
gtcgccagac caggtgagct cagcggtcgg agatgctgac gtcgctcggc gcacgcctgg   360
ctcgacgagc tgacggtgca cgcggagctg gcgtggccaa gttctaaacc cgcgcaatcc   420
cggcgttatg gcaatgcgac aacgcaggtc ctgcgtgagg cgagggacaa ggagcgcgag   480
ctgcagaacg cgagggcgcc cacggatgtc agcggatttc ttgcgcccgt ggcgtttgg    540
gagctgaagc acctgcgcaa gctgtcgtcc cttaccagcc ttacctacta catgcacctg   600
gtgacggtga gtgcgcgtgt tggagagttg gggcgcgtgc gtgcgtgctc gctagccgcc   660
gcgtggcgcg taagcgtggc gcgcgagcgt tagccagggt tagcctcgcg ggtgttcaga   720
cctgcagccg ccgcagctgc ggtgggtaag ggcagttgg ctctggagcg gggcagcggt    780
gttgcgcgga gccgcggagg gttcgagaag gaccgccggg caggtccgcc gtaacgcacg   840
cagaggggt agctgccgaa ggttgttggg cgcagtggag gagtggttc ccggtactcg     900
gtaacgcacg ttgcccagac cccgccatca aaccaggact tgcctgacag catccgccag   960
ggcctgccgg cgtctgccgt gccgtgctgc tgtgctcgct ccgtcctatt tagcatttcc  1020
tttcgcccctt ccttccctgc ctcctgaacc ccctgccc tgtgccgacc cccgcactac   1080
ctacctcgct cccctcccac agccccggcg gctgcagctg atgcacgggc tggacctggt  1140
ggtgaccagc cgcgcctgcg acgtgcggcc gtacgagcac aaccgcaccg ccgaggagtg  1200
cggtgccgac ggcgacggca tggccgtctc gttcgccgag gcgcgccagg tgtatgccga  1260
gctgaagcgc ggcacgggcg cgccagcgg cagcggtagc aacggggcgg cggcggcgcc   1320
ggtggcggtg gcggcgggcg tgtccaacat cgtggcgctg ccgcgcgagc tgccgttcgt  1380
gccgcttccc ggcggcgcga cggagggtgg cgaggcggga cggaggccg ccgccggggc   1440
ggcggcagca gccgcagccg cagctgggga aggcaccggg ccgggggccc aggggcaggg  1500
ggcagggggc ctacagctgc cgttggcctc gaccgaggcc atcggccgca tgctgcgcag  1560
cccgcggag gtggtgtcgg caaagcttgc tgaggcggcc ctggcggcct ggccgccgc    1620
cgccgccagc ccgctcggcg ccgccgccga gagcttttac gctgggctgg cctcgctgcc  1680
```

```
catcccgctg gccggcggcc tggtgggcgc caacaacaag gccgccaaca cactgctggc    1740
gccgccgaac ggggcggcgg ccagcagcag tggcggcggt ggtggtagcg gtggcgcggc    1800
ggcagcgtct gaggttgtgg gctcgtcgcg gggcgcccag ggagcggacc ctgcggaccc    1860
cggcgcaccc aacaccagcg gcaaggccac tgccgcctcc atcgcggcca tggcaactgc    1920
cgagctgcgc tcccgccgcc tgggcggcac cggtcctgcc aagacggggg gcagcggcgc    1980
cgccagcagc ggcagcagca gcggcggtat tggtgcgggt ggcatggcgc cagtaacggc    2040
tggcggcatg cgtttgtcac ccgccgccac cgccttctcc gcccctcccg ctgccaccgt    2100
ctcctccctg gcctccacgg acgccgggac tgcgctggtg ccggtggctt catcctcggc    2160
ggcttccctc accttctcct ccagctctgc ctactcctgc ccctcagaat ggtttgtggt    2220
ggacgaccct gcctcggcca cacgcatctt cgtcatccag gtaggaaccg tgggaacctt    2280
taaggagttg aggtgtgcgc ctagaaagta aggaaatgcg ggtaggtgaa tgcatgcaag    2340
aagacagcgt tctgatacta cggcaaaccc tcacaagcgg tactcgcgcc gcctccacaa    2400
cagggctcgg acacgctgga ccactggaag ctgaacctga cgttcgaccc ggtggtgttt    2460
gaggagccgg ccctgggcgt caaggtgcac cgcggcgtgt acgaggcggc gctggtgctg    2520
tacgagcgct tcctgccgct ggtgtacgaa cacctggagg cgtcgccctt ctccaaggtc    2580
accttcacgg tgaggggttg gaggggtggg tggagaggtg gctttcagtt atctcgcacg    2640
aggactggaa gtaccaagcc aggggtaagc ggggtgggcg ggagcggggc agactggaga    2700
ggagttccaa gtggaccggg cactctacgg cacctgtgcc tgtgcctgac accgcacctg    2760
tgctgcctcc atgccgtccg ccccccccgac cctcagggcc attccatcgg tggctccatg    2820
gccacgctgc tgatgctcat gtaccgcaac cggggcgtgc tgccgccgca ctccatcgcc    2880
accgtctaca ccttttggcgc gcccgccgtg ttctgccagc agcagcaacc ggccgtagcc    2940
gacgcctctt cggcctgctg caacggcagt agcagcaacg gcagtagcac gcccgccagc    3000
ggcagctcca gcccgaggag cggcagcccc ggctcagcct cggcctcgtc gctgccggcc    3060
ggcagtggca gcggtgccgg cggcatgtcg ctgtgggcgc tgggcctgag cggcttttggc    3120 atgggcggcg ccagtctggc cggcggcggc agcaccagcg cccctagcag taccgccggc    3180
ctggcgagtg tggacggcgg cgccgtggcg gctggcggcg gcggcagcgg cttcaactca    3240
tcagggctgg gcttcatgag cgtcgaggtg cggccagggt tggtctggga gggacgggct    3300
ggctgcaagg cggctactga gggacggaca cgggctgtgt gttctggcat gtcaagcact    3360
ttcgccgctc gtaacctatc tgcaaaactc actgtgtgtg tcgtggtgtg ccacgcagga    3420 ccccccaggcg gtctcgatgc cgccgggcgc cgcccaggcg ccctcgcccg cgtccgcgcc    3480
ggcgcccacc gccggccccg gccacaacag ccacagcagc cacagcaagg ccggccccgc    3540
cgccgccaag agctgcgcct gcggtgttga cgggctgctg acgcggctgg ggctggcgcc    3600
gcacgtggtg cgcaacgtgg tgatggcgcg ggacgtggtg ccgcgcgcct tcgcgtgcga    3660
ctacagcctg gtggcggaca tcctcaaggg ctggggggccg gccttccggg agcactgctg    3720
cctcaacagg tgggagcagg gggggcgtgt ggcgggcgtg ctgcagagtg ctcggggcgg    3780
gtggggcggg tggcgcgggg gggacgcagg ctgcagctgg ggctgtgctt gggccggaca    3840
cggggcaacc atggcccgcg gtcagggcgc gggtgctgta gatggtgcgg tgggttgcgt    3900
gacctgtggc tcagttgctg gcacgactga cacgacgccg ggcggccctc cgcgcaggca    3960
cggccgcaag cacctgtact acttcgtggg gcgcatgtgc atcctgcagc ggacgcctg    4020 gcacagcttc gtgggcggcg acccggagca ccccatgctg ccgcccggcc ccgagctgta    4080
```

```
cgcgctggcg gagcccgagg acgccgccgc tgcccgcgcc cactaccccg ccctgtccga   4140
cctgcccatc ctcaacgccg tcaccagcaa tggccacacc cgcggcagcg gcggcaacgg   4200
cgccaacgcc gccgtcaacg ccgccgtcaa cgcctccggc cccagcgccg ccgcctccgg   4260
cggcggcggc ggctcgcagc agccgaccgc ggcggctgct gtgccgtcca ccgccaactt   4320
cggcacggcg ctggtggcgt cggcggcgca gcgggagcgc gacgcgcgcg cggcggctc    4380 tcgtctgcag ccgcgcagtg tggtggaggc ggtgtgggag atcatggaca acccgcaccc   4440
tctggagaca ctggcggacc cgggcgccta cctggcctcc ggcagcatct cccgctacca   4500
caacccggag cactacacca aggcgctggg ccgcctgacg cacctgaagc ggctggcgga   4560
gcggcggcag cacccgcacg gccaggcgca gcagaagcag gcgcagccgc aggccggcga   4620
gggcggcatc cgcagcatgt tcgcggggcg caacatccgc agctttggcg gcggtgtgcg   4680
cagcggcagc ggcagtggca gcgccggccg gcggggctg ctgcaccagc aggcggcctc    4740
caacggcacc gcgctgacg cggtgctggc cagtggcgcc gccggcgcgg ccgccgcggc    4800
ctggggcagc gcgccgcagc tggcggacct ggtgagcggc aacggcggcc gcgcgagtgc   4860
gggctacgag ggcggcgtgt gggacagcag tgacgggctg gacctgcacc tcagcgactt   4920
catgggcgcc tccgcggtgg gcgccgccga cccacacgcc tgccggtgag gcggcggcga   4980
cagcggctgg gtgtgggctg gatgcaggtg acaggcaagg cgcagtcaga ggaggcagaa   5040
gcggcagagg cggcagaggc gacggaagcg gcaagttgca gcgtgcagga gctggagtag   5100
agccgctgtg cagtgcgatc agatgcagca gagacgtgga gcttcagcgc ttagcgggtg   5160
cggcatgagc gcctgagcgc ctgagcacgg ggtggacgcc gaggaggtcc ggaagggcgt   5220
tgcacggggt gaacgtggcc agggcgtcagc cttattacgg tgcgtaatgg ttggggtctg    5280
cgactcggtt tgcaactgcg tatgcatata ccaatggtgg tggcgcgtcg cgagccgctc   5340
tgcgggctgc cgcaatatgt gcggcggccg caacacgggc acatcagcgc attatactat   5400
tcccttactg aagggcagcg gagtgagctg tggacggcat gggtataggt gtcggcgccg    5460
ccggggcctc tgacccgcca cgcctgcgcc gggccagggg ctgcacagac aggctaagga   5520
tcgatctagc agaccgtcaa ggtcattgcc ttgttgattg gtatgctctg tactactatg   5580
tattccggct ttcgagtgcc gggcagtgac tgcggccaag cagaactgcc cgtgacctcc   5640
tccgggttag gcagccaggg gcctgcgcct ctgcgcgtgg ggagcagtgc cgggcagccc   5700
gggcacaaat gagagcgagt gtgcctcttc tattagccat gtgccaaatg ttcttaactg   5760
ttatccaaaa gtgctgtgtg cgatttcatg tctgctggtt tgtgcgtaca tagggaccca   5820
cagatcccct tcctcccatg cgccgcatgc tgccgctgcc acaatttgtg ccggcgctgc   5880
gtgtgtgggg gaaccgggg ttgcgtgacg tgcgtgtgaa gagtgtgcat gtgtcccgcg    5940
gtgtcgcggc atttgctgta gttgtgctgt tgggtgctag gagcggggcg agagtgaaga   6000
gaacccttca tgtcagggcc cagcgatcgt cttgctgggg caccttgcgt gtgctgtgct   6060
ttgctattct attcctcttg agagtagctg cgctgctcag aggcatgcag tgtgtagagt   6120
tgacgatctg ttgcagtgtt gcatagagcc acgctggagc tgcagttagt ccagaggtgt   6180
cacggtgctt gcggcgacgc gtctgccgcg gtactcctac ggctccgtgt tgcaccgcgg   6240
cagcccaagc gcctcggcag ctgcagcata aggcgtttga gcgggtaggt ccatgtgtct   6300
ctgtcctatt catcgcggta gctgatccag tagctggtag gcggtgcgct tcggtgtagg   6360
ttgaactagc agatttcccg ggcaatgcgt gtggcagccc aagctgaaca gggcaggtgg   6420
```

```
tggctgggac gatgctcccg cgcaggaacg atgctcccgc gcacctcaca ctcatgctca    6480
aggttgacgc cccgattggg gattttttgtg caggtgttaa agctatgccc cgtacttggg    6540
gtgtgttcgc cgtgtggcgt gaaggcgtga agttactcct tgaatttgag acatagacag    6600
gtggtgcagc gcgtgaagcg cgtgtcaagg ctgcgcgcag cccatgtaag gtccgagatg    6660
c                                                                     6661

<210> SEQ ID NO 26
<211> LENGTH: 5302
<212> TYPE: DNA
<213> ORGANISM: Chlamydomonas reinhardtii

<400> SEQUENCE: 26
cgtgaatggc aaaacaatag caacaatgca agcgtacacc gggcaaacca agcttcggcc      60
tgggcgcggg acagggagtg ccgctcccac cgagcccagg actcgcacct gtgtagttac     120
aagagtgcta gcgccacctg aagcgccagg aaggaggccc cgtagcgcct cgtctctgac     180
gcaagatggg caagcgtcgc ccgcaccttc aacgccaacg acagcagctt ctgtgtggtc     240
gagcaccact agctatatga gccagctatt gtcgcacttt gtgagggttc cgacgtttgc     300
gtcgccagac caggtcctgc gtgaggcgag ggacaaggag cgcgagctgc agaacgcgag     360
ggcgcccacg gatgtcagcg gatttcttgc gcccgttggc gtttgggagc tgaagcacct     420
gcgcaagctg tcgtccctta ccagccttac ctactacatg cacctggtga cgccccggcg     480
gctgcagctg atgcacgggc tggacctggt ggtgaccagc cgcgcctgcg acgtgcggcc     540
gtacgagcac aaccgcaccg ccgaggagtg cgtgccgac ggcgacggca tggccgtctc     600
gttcgccgag gcgcgccagg tgtatgccga gctgaagcgc ggcacgggcg cgccagcgg     660 cagcggtagc aacggggcgg cggcggcgcc ggtggcggtg gcggcgggcg tgtccaacat     720
cgtggcgctg ccgcgcgagc tgccgttcgt gccgcttccc ggcggcgcga cggagggtgg     780
cgaggcggga gcggaggccg ccgcccgggc ggcggcagca ccgcagccg cagctggga     840 aggcaccggg ccgggggccc aggggcaggg ggcaggggc ctacagctgc cgttggcctc     900
gaccgaggcc atcggccgca tgctgcgcag cccggcggag gtggtgtcgg caaagcttgc     960
tgaggcggcc ctggcggcct cggccgccgc cgccgccagc ccgctcggcg ccgccgccga    1020
gagcttttac gctgggctgg cctcgctgcc catcccgctg gccggcggcc tggtgggcgc    1080
caacaacaag gccgccaaca cactgctggc gccgccgaac ggggcggcgg ccagcagcag    1140
tggcggcggt ggtggtagcg gtggcgcggc ggcagcgtct gaggttgtgg gctcgtcgcg    1200
gggcgcccag ggagcggacc ctgcggaccc cggcgcaccc aacaccagcg gcaaggccac    1260
tgccgcctcc atcgcggcca tgcaactgcg cgagctgcgc tcccgccgcc tgggcggcac    1320
cggtcctgcc aagacggggg gcagcggcgc cgccagcagc ggcagcagca gcggcggtat    1380
tggtgcgggt ggcatggcgc cagtaacggc tggcggcatg cgtttgtcac ccgccgccac    1440
cgccttctcc gccctcccg ctgccaccgt ctcctccctg gcctccacgg acgccgggac    1500
tgcgctggtg ccggtggctt catcctcggc ggcttccctc accttctcct ccagctctgc    1560
ctactcctgc ccctcagaat ggtttgtggt ggacgaccct gcctcggcca cacgcatctt    1620
cgtcatccag ggctcggaca cgctggacca ctggaagctg aacctgacgt tcgacccggt    1680
ggtgtttgag gagccggccc tgggcgtcaa ggtgcaccgc ggcgtgtacg aggcggcgct    1740
ggtgctgtac gagcgcttcc tgccgctggt gtacgaacac ctggaggcgt cgccttctc    1800 caaggtcacc ttcacgggcc attccatcgg tggctccatg gccacgctgc tgatgctcat    1860
```

```
gtaccgcaac cggggcgtgc tgccgccgca ctccatcgcc accgtctaca cctttggcgc    1920
gcccgccgtg ttctgccagc agcagcaacc ggccgtagcc gacgcctctt cggcctgctg    1980
caacggcagt agcagcaacg gcagtagcac gcccgccagc ggcagctcca gcccgaggag    2040
cggcagcccc ggctcagcct cggcctcgtc gctgccggcc ggcagtggca gcggtgccgg    2100
cggcatgtcg ctgtgggcgc tgggcctgag cggctttggc atgggcggcg ccagtctggc    2160
cggcggcggc agcaccagcg cccctagcag taccgccggc ctggcgagtg tggacgcgcg    2220
cgccgtggcg gctggcggcg gcggcagcgg cttcaactca tcagggctgg gcttcatgag    2280
cgtcgaggac ccccaggcgg tctcgatgcc gccgggcgcc gcccaggcgc cctcgccccg    2340
gtccgcgccg gcgcccaccg ccggccccgg ccacaacagc cacagcagcc acagcaaggc    2400 cggcccccgcc gccgccaaga gctgcgcctg cggtgttgac gggctgctga cgcggctggg    2460
gctggcgccg cacgtggtgc gcaacgtggt gatggcgcgg gacgtggtgc gcgcgccctt    2520
cgcgtgcgac tacagcctgg tggcggacat cctcaagggc tgggggccgg ccttccggga    2580
gcactgctgc ctcaacaggc acggccgcaa gcacctgtac tacttcgtgg ggcgcatgtg    2640
catcctgcag ccggacgcct ggcacagctt cgtgggcggc gacccggagc accccatgct    2700
gccgcccggc cccgagctgt acgcgctggc ggagcccgag gacgccgccg ctgcccgcgc    2760
ccactacccc gccctgtccg acctgcccat cctcaacgcc gtcaccagca atggccacac    2820
ccgcggcagc ggcggcaacg gcgccaacgc cgccgtcaac gccgccgtca acgcctccgg    2880
ccccagcgcc gccgcctccg gcggcggcgg cggctcgcag cagccgaccg cggcggctgc    2940
tgtgccgtcc accgccaact tcggcacggc gctggtggcg tcggcggcgc agcgggagcg    3000
cgacgcgcgc ggcggcggct tcgtctgca gccgcgcagt gtggtggagg cggtgtggga    3060
gatcatggac aacccgcacc ctctggagac actggcggac ccgggcgcct acctggcctc    3120
cggcagcatc tcccgctacc acaacccgga gcactacacc aaggcgctgg gccgcctgac    3180
gcacctgaag cggctggcgg agcggcggca gcacccgcac ggccaggcgc agcagaagca    3240
ggcgcagccg caggcggcg agggcggcat ccgcagcatg ttcgcggggc gcaacatccg    3300
cagctttggc ggcggtgtgc gcagcggcag cggcagtggc agcgccggcc ggcggggct    3360 gctgcaccag caggcggcct ccaacggcac cgcggctgac gcggtgctgg ccagtggcgc    3420
cgccggcgcg gccgccgcgg cctggggcag cgcgccgcag ctggcggacc tggtgagcgg    3480
caacggcggc cgcgcgagtg cgggctacga gggcggcgtg tgggacagca gtgacgggct    3540
ggacctgcac ctcagcgact tcatgggcgc ctccgcggtg ggcgccgccg acccacacgc    3600
ctgccggtga ggcggcggcg acagcggctg ggtgtgggct ggatgcaggt gacaggcaag    3660
gcgcagtcag aggaggcaga agcggcagag cggcagagg cgacggaagc ggcaagttgc    3720
agcgtgcagg agctggagta gagccgctgt gcagtgcgat cagatgcagc agagacgtgg    3780
agcttcagcg cttagcgggt gcggcatgag cgcctgagcg cctgagcacg gggtggacgc    3840
cgaggaggtc cggaagggcg ttgcacgggg tgaacgtggc caggggtcag ccttattacg    3900
gtgcgtaatg gttggggtct gcgactcggt ttgcaactgc gtatgcatat accaatggtg    3960
gtggcgcgtc gcgagccgct ctgcgggctg ccgcaatatg gcggcggcc gcaacacggg    4020 cacatcagcg cattatacta ttcccttact gaagggcagc ggagtgagct gtggacggca    4080
tgggtatagg tgtcggcgcc gccggggcct ctgacccgcc acgcctgcgc cgggccaggg    4140
gctgcacaga caggctaagg atcgatctag cagaccgtca aggtcattgc cttgttgatt    4200
```

```
ggtatgctct gtactactat gtattccggc tttcgagtgc cgggcagtga ctgcggccaa    4260
gcagaactgc ccgtgacctc ctccgggtta ggcagccagg ggcctgcgcc tctgcgcgtg    4320
gggagcagtg ccgggcagcc cgggcacaaa tgagagcgag tgtgcctctt ctattagcca    4380
tgtgccaaat gttcttaact gttatccaaa agtgctgtgt gcgatttcat gtctgctggt    4440
ttgtgcgtac ataggaccc acagatcccc ttcctcccat gcgccgcatg ctgccgctgc    4500
cacaatttgt gccggcgctg cgtgtgtggg ggaaccggg gttgcgtgac gtgcgtgtga    4560
agagtgtgca tgtgtcccgc ggtgtcgcgg catttgctgt agttgtgctg ttgggtgcta    4620
ggagcggggc gagagtgaag agaacccttc atgtcagggc ccagcgatcg tcttgctggg    4680
gcaccttgcg tgtgctgtgc tttgctattc tattcctctt gagagtagct gcgctgctca    4740
gaggcatgca gtgtgtagag ttgacgatct gttgcagtgt tgcatagagc cacgctggag    4800
ctgcagttag tccagaggtg tcacggtgct tgcggcgacg cgtctgccgc ggtactccta    4860
cggctccgtg ttgcaccgcg gcagcccaag cgcctcggca gctgcagcat aaggcgtttg    4920
agcgggtagg tccatgtgtc tctgtcctat tcatcgcggt agctgatcca gtagctggta    4980
ggcggtgcgc ttcggtgtag gttgaactag cagatttccc gggcaatgcg tgtggcagcc    5040
caagctgaac agggcaggtg gtggctggga cgatgctccc gcgcaggaac gatgctcccg    5100
cgcacctcac actcatgctc aaggttgacg ccccgattgg ggattttgt gcaggtgtta    5160 aagctatgcc ccgtacttgg ggtgtgttcg ccgtgtggcg tgaaggcgtg aagttactcc    5220
ttgaatttga gacatagaca ggtggtgcag cgcgtgaagc gcgtgtcaag gctgcgcgca    5280
gcccatgtaa ggtccgagat gc                                             5302

<210> SEQ ID NO 27
<211> LENGTH: 3354
<212> TYPE: DNA
<213> ORGANISM: Chlamydomonas reinhardtii

<400> SEQUENCE: 27
atgagccagc tattgtcgca ctttgtgagg gttccgacgt ttgcgtcgcc agaccaggtc      60
ctgcgtgagg cgagggacaa ggagcgcgag ctgcagaacg cgagggcgcc cacggatgtc     120
agcggatttc ttgcgcccgt tggcgttttgg gagctgaagc acctgcgcaa gctgtcgtcc     180
cttaccagcc ttacctacta catgcacctg gtgacgcccc ggcggctgca gctgatgcac     240
gggctggacc tggtggtgac cagccgcgcc tgcgacgtgc ggccgtacga gcacaaccgc     300
accgccgagg agtgcggtgc cgacggcgac ggcatggccg tctcgttcgc cgaggcgcgc     360
caggtgtatg ccgagctgaa gcgcggcacg ggcggcgcca gcgcagcgg tagcaacggg     420 gcggcggcgg cgccggtggc ggtggcgcg gcgtgtcca acatcgtggc gctgccgcgc     480
gagctgccgt tcgtgccgct tcccggcggc gcgacggagg gtggcgaggc gggagcggag     540
gccgccgccg gggcggcggc agcagccgca gccgcagctg gggaaggcac cgggccgggg     600
gcccaggggc aggggcagg gggcctacag ctgccgttgg cctcgaccga ggccatcggc     660
cgcatgctgc gcagcccggc ggaggtggtg tcggcaaagc ttgctgaggc ggccctggcg     720
gcctcggccg ccgccgccgc cagcccgctc ggcgccgccg ccgagagctt ttacgctggg     780
ctggcctcgc tgcccatccc gctggccggc ggcctggtgg gcgccaacaa caaggccgcc     840
aacacactgc tggcgccgcc gaacggggcg gcggccagca gcagtggcgg cggtggtggt     900
agcggtggcg cggcggcagc gtctgaggtt gtgggctcgt cgcgggggcgc ccaggagcg    960 gaccctgcgg accccggcgc acccaacacc agcggcaagg ccactgccgc ctccatcgcg   1020
```

```
gccatggcaa ctgccgagct gcgctcccgc cgcctgggcg gcaccggtcc tgccaagacg    1080
gggggcagcg gcgccgccag cagcggcagc agcagcggcg gtattggtgc gggtggcatg    1140
gcgccagtaa cggctggcgg catgcgtttg tcacccgccg ccaccgcctt ctccgcccct    1200
cccgctgcca ccgtctcctc cctggcctcc acggacgccg ggactgcgct ggtgccggtg    1260
gcttcatcct cggcggcttc cctcaccttc tcctccagct ctgcctactc ctgcccctca    1320
gaatggtttg tggtggacga ccctgcctcg gccacacgca tcttcgtcat ccagggctcg    1380
gacacgctgg accactggaa gctgaacctg acgttcgacc cggtggtgtt tgaggagccg    1440
gccctgggcg tcaaggtgca ccgcggcgtg tacgaggcgg cgctggtgct gtacgagcgc    1500
ttcctgccgc tggtgtacga acacctggag gcgtcgccct tctccaaggt caccttcacg    1560
ggccattcca tcggtggctc catggccacg ctgctgatgc tcatgtaccg caacggggc    1620 gtgctgccgc cgcactccat cgccaccgtc tacacctttg gcgcgcccgc cgtgttctgc    1680
cagcagcagc aaccgccgt agccgacgcc tcttcggcct gctgcaacgg cagtagcagc    1740
aacggcagta gcacgcccgc cagcggcagc tccagcccga ggagcggcag ccccggctca    1800
gcctcggcct cgtcgctgcc ggccggcagt ggcagcggtg ccggcggcat gtcgctgtgg    1860
gcgctgggcc tgagcggctt tggcatgggc ggcgccagtc tggccggcgg cggcagcacc    1920
agcgccccta gcagtaccgc cggcctggcg agtgtggacg gcggcgccgt ggcggctggc    1980
ggcggcggca gcggcttcaa ctcatcaggg ctgggcttca tgagcgtcga ggaccccag    2040 gcggtctcga tgccgccggg cgccgcccag gcgccctcgc ccgcgtccgc gccggcgccc    2100
accgccggcc ccggccacaa cagccacagc agccacagca aggccggccc cgccgccgcc    2160
aagagctgcg cctgcggtgt tgacgggctg ctgacgcggc tggggctggc gccgcacgtg    2220
gtgcgcaacg tggtgatggc gcgggacgtg gtgccgcgcg ccttcgcgtg cgactacagc    2280
ctggtggcgg acatcctcaa gggctggggg ccggccttcc gggagcactg ctgcctcaac    2340
aggcacggcc gcaagcacct gtactacttc gtggggcgca tgtgcatcct gcagccggac    2400
gcctggcaca gcttcgtggg cggcgacccg gagcacccca tgctgccgcc cggccccgag    2460
ctgtacgcgc tggcggagcc cgaggacgcc gccgctgccc gcgcccacta ccccgccctg    2520
tccgacctgc ccatcctcaa cgccgtcacc agcaatggcc acaccgcgg cagcggcggc    2580 aacgcgcca acgccgccgt caacgccgcc gtcaacgcct ccggccccag cgccgccgcc    2640
tccggcggcg gcggcggctc gcagcagccg accgcggcgg ctgctgtgcc gtccaccgcc    2700
aacttcggca cggcgctggt ggcgtcggcg gcgcagcggg agcgcgacgc gcgcggcggc    2760
ggctctcgtc tgcagccgcg cagtgtggtg gaggcggtgt gggagatcat ggacaacccg    2820 cacccctctgg agacactggc ggacccgggc gcctacctgg cctccggcag catctcccgc    2880
taccacaacc cggagcacta caccaaggcg ctgggccgcc tgacgcacct gaagcggctg    2940
gcggagcggc ggcagcaccc gcacggccag gcgcagcaga agcaggcgca gccgcaggcc    3000
ggcgagggcg gcatccgcag catgttcgcg gggcgcaaca tccgcagctt tggcggcggt    3060
gtgcgcagcg gcagcggcag tggcagcgcc ggcggcgggg gctgctgca ccagcaggcg    3120 gcctccaacg gcaccgcggc tgacgcggtg ctggccagtg gcgccgccgg cgcggccgcc    3180
gcggcctggg gcagcgcgcc gcagctggcg gacctggtga gcggcaacgg cggccgcgcg    3240
agtgcgggct acgagggcgg cgtgtgggac agcagtgacg gctgaccct gcacctcagc    3300 gacttcatgg gcgcctccgc ggtgggcgcc gccgacccac acgcctgccg gtga         3354
```